United States Patent [19]

Green et al.

[11] Patent Number: 5,834,187
[45] Date of Patent: Nov. 10, 1998

[54] SEQUENCE AND ANALYSIS OF LKP PILIN STRUCTURAL GENES AND THE LKP PILI OPERON OF NONTYPABLE *HAEMOPHILUS INFLUENZAE*

[75] Inventors: Bruce A. Green, Pittsford, N.Y.; Charles C. Brinton, Jr., Export, Pa.

[73] Assignee: Bactex, Inc., Pittsburgh, Pa.

[21] Appl. No.: 473,750

[22] Filed: Jun. 7, 1995

Related U.S. Application Data

[63] Continuation-in-part of Ser. No. 277,231, Jul. 19, 1994.
[51] Int. Cl.$^6$ .............................. C12Q 1/68; C12Q 19/34; C07H 21/02; C07K 5/00
[52] U.S. Cl. .............................. 435/6; 435/91.2; 435/7.3; 435/70.21; 435/326; 435/332; 435/331; 435/287.2; 530/389.1; 530/867; 530/866; 530/388.1; 530/350; 424/130.1; 424/141.1; 424/242.1; 536/23.1; 536/24.3; 536/24.32; 536/24.33
[58] Field of Search .............................. 435/6, 91.2, 7.3, 435/7.1, 70.21, 326, 332, 331, 287.2; 536/23.1, 24.3–24.33, 26.5; 530/350, 388.1, 389.1, 867, 866; 424/242.1, 130.1, 141.1

[56] References Cited

U.S. PATENT DOCUMENTS

| | | | |
|---|---|---|---|
| 4,801,690 | 1/1989 | Brinton, Jr. et al. | 530/396 |
| 5,336,490 | 8/1994 | Brinton, Jr. et al. | 424/242.1 |
| 5,399,481 | 3/1995 | McMillan et al. | 435/7.1 |

FOREIGN PATENT DOCUMENTS

| | | |
|---|---|---|
| 93/19090 | 9/1993 | WIPO. |

OTHER PUBLICATIONS

Van Ham et al. Cell 73: 1187–1196, 1993.
Van Ham et al. EMBO J. 8: 3535–3540, 1989.
Langerman and Wright Molecular Microbiology 4: 221–230, Cited in SN 277231, 1990.
Sambrook et al. in Molecular Cloning: A Laboratory Manual, Cited in SN 277231, 1989.
Whitney and Farleym Infection and Immunity 61: 1559–1562, 1993.
Van Ham et al, Genbank Sequence Listing, Submitted May 16, 1994.
Watson, Wendy, J. et al., "Identification of a Gene Essential for Piliation in *Haemophilus influenzae* Type b with Homology to the Pilus Assembly Platform Genes of Gram–Negative Bacteria," *Infection and Immunity* 62(2):468–475 (1994).
van Ham, S. M. et al., "Phase Variation of *H. influenzae* Fimbriae: Transcriptional Control of Two Divergent Genes through a Variable Combined Promoter Region," *Cell* 73:1187–1196 (1993).
van Ham, S. M. et al., "Cloning and Expression in *Escherichia coli* of *Haemophilus influenzae* Fimbrial Genes Establishes Adherence to Oropharyngeal Epithelial Cells," *EMBO Journal* 8(11):3535–3540 (1989).

van Alphen, L. et al., "Blocking of Fimbria–Mediated Adherence of *Haemophilus influenzae* by Sialyl Gangliosides," *Infection and Immunity* 59(12):4473–4477 (1991).
Strom, M.S. et al., "A Single Bifunctional Enzyme, PilD, Catalyzes Cleavage and N–methylation of Proteins Belonging to the Type IV Pilin Family," *Proc. Natl. Acad. Sci. USA* 90:2404–2408 (1993).
St. Geme, J.W., III et al., "High–Molecular–Weight Proteins of Nontypable *Haemophilus influenzae* Mediate Attachment to Human Epithelial Cells," *Proc. Natl. Acad. Sci. USA* 90:2875–2879 (1993).
Sinha, N.D. et al., "Polymer Support Oligonucleotide Synthesis XVIII$^{1,2}$: Use of β–cyanoethyl–N,N–dialkylamino–/N–morpholino Phosphoramidite of Deoxynucleosides for the Synthesis of DNA Fragments Simplifying Deprotection and Isolation of the Final Product," *Nucleic Acids Research* 12(11):4539–4557 (1984).
Saiki, R.K. et al., "Primer–Directed Enzymatic Amplification of DNA With a Thermostable DNA Polymerase," *Science* 239:487–490 (1988).
Palmer, K. . and Munson, R.S., Jr. "Construction of Chimaeric Genes for Mapping a Surface–Exposed Epitope on the Pilus of Non–typable *Haemophilus influenzae* Strain M37," *Molecular Microbiology* 6(18):2583–2588 (1992).
Musher, D.M. et al., "Pneumonia and Acute Febrile Tracheobronchitis Due to *Haemophilus influenzae,*" *Annals of Internal Medicine* 99:444–450 (1983).
Miller, J.H. "Generalized Transduction; Use of P1 in Strain Construction," *Experiments in Molecular Genetics*, pp. 201–205 Cold Spring Harbor Laboratory, Cold Spring Harbor, NY (1972).
McCaman, M.T. et al., "Genetics and Regulation of Peptidase N in *Escherichia coli* K–12," *Journal of Bacteriology* 152(2):848–854 (1982).
Laemmli, U.K., "Cleavage of Structural Proteins During the Assembly of the Head of Bacteriophage T4," *Nature* 227:680–685 (1970).

(List continued on next page.)

*Primary Examiner*—W. Gary Jones
*Assistant Examiner*—Dianne Rees

[57] ABSTRACT

The invention relates to the isolation and cloning of the structural gene, hipP, for the NTHi pili serotype 5 and the LKP operon. The invention relates to DNA molecules capable of hybridizing to the DNA sequences of the *Haemophilus influenzae* genome related to the pili. The invention further relates to a DNA molecule which encodes a pili protein, particularly a tip adhesion protein. The DNA molecules of the invention can be used in a method for assaying a sample, such as a blood sample, for the presence of *Haemophilus influenzae* in the sample. Accordingly, the invention further relates to the use of the DNA molecules as a diagnostic. The invention also relates to a recombinant *Haemophilus influenzae* pili protein, such as a tip adhesion protein. The protein can be employed in a method for immunizing an animal, such as a human, as a therapeutic or diagnostic.

25 Claims, 14 Drawing Sheets

OTHER PUBLICATIONS

Karasic, R.B. et al., "Evaluation of Pilus Vaccines for Prevention of Experimental Ptitis Media Caused by Nontypable *Haemophilus influenzae,*" *Pediatr. Infect. Dis. J* 8(1):S062–S065 (1989).

Kar, S. et al., "Cloning and Expression in *Escherichia coli* of LKP Pilus Genes from a Nontypeable *Haemophilus influenzae* Strain," *Infection and Immunity* 58(4):903–908 (1990).

Gilsdorf, J.R., "Cloning, Expression, and Sequence Analysis of the *Haemophilus influenzae* Type b Strain M43p$^+$Pilin Gene," *Infection and Immunity* 58(4):1065–1072 (1990).

Forney, L.J. et al., "Comparison and Analysis of the Nucleotide Sequences of Pilin Genes from *Haemophilus influenzae* Type b Strains Eagan and M43," *Infection and Immunity* 59(6):1991–1996 (1991).

Coleman, T. et al., "Molecular Cloning, Expression, and Sequence of the Pilin Gene from Nontypeable *Haemophilus influenzae* M37," *Infection and Immunity* 59(5):1716–1722 (1991).

Chang, A.C.Y. and Cohen, S.N. "Construction and Characterization of Amplifiable Multicopy DNA Cloning Vehicles Derived from the P15A Cryptic Miniplasmid," *Journal of Bacteriology* 134(3):1141–1156 (1978).

Brinton, C.C., Jr. et al., "Design and Development of Pilus Vaccines for *Haemophilus influenzae* Diseases," *Pediatr. Infect. Dis. J.* 8(1):S54–S61 (1989).

Bluestone, C.D. and Klein, J.O., "Otitis Media With Effusion, Atelectasis, and Eustachian Tube Dysfunction," *Pediatric Otolaryngology* pp. 356–512 (1983) vol. # not applicable.

Haslam, D. et al., "The Amino–Terminal Domain of the P–Pilus Adhesion Determines Receptor Specificity," *Journal of Cellular Biochemistry Supplement 18A*:47, Abstract B112 (1994).

Langermann S. and Wright A., "Molecular Analysis of the *Haemophilus Influenzae* Type b Pilin Gene,", *Molecular Microbiology*, 4(3):221–230 (1990).

van Ham, S.M. et al., "The Fimbrial Gene Cluster of *Haemophilus Influenzae* Type b," *Molecular Microbiology*, 13(4): 673–684 (1994).

Lindberg, F. et al., "Gene Products Specifying Adhesion of Uropathogenic *Escherichia Coli* Are Minor Components of Pili," *Proc. Natl. Acad. Sci. USA*, 83:1891–1895 (1986).

Watson, W.J., et al., "Identification of a Gene Essential for Piliation in *Haemophilus Influenzae* Type b With Homology to the Pilus Assembly Platform Genes of Gram–Negative Bacteria," *Database EMBL/GenBank/DDBJ on STRAND, ID=HIIFC, AC=U02932* (1994).

Smith, A.L., "hif B of *H. Influenzae* is a Member of the Chaperone Family," *Database EMBL/GenBank/DDBJ on STRAND, ID=HIHIFB, AC=X66606* (1992).

VanHam, S.M., et al., "Cloning and Expression in *Escherichia Coli* of *Haemophilus Influenzae* Fimbral Genes Establishes Adherence to Oropharyn–Geal Epithelial Cells," *EMBO J.*, 8:3535–3540 (1989).

Green, B.A., et al., "Sequence of LKP Serotype 5 hifA Gene," *Database EMBL/GenBank/DDBJ on STRAND, ID=HII9795, AC=U19795* (1995).

```
                 10         20         30         40         50         60         70
                 *          *          *          *          *          *          *
LKP1 hifA    MEQFIMKKTT TGSLILLAFA TNAADPQVST ETSGKVTFFG KVVENTCKVK TDSKNMSVVL NDVGKNHijT LKP4 hifA            10         20         30         140        150        160        -
[646]        ........... ..L.L...... ........... G.-VQADIN.. ........EH..L.... ........S.S LKP5 hifA            10         20         130        40         50         60         701
[ 618 ]      ........... ..L.L...... G.VQAADPNP ..K......Y. ........ SGNRD.... ........A..SQ 80         90         100        110        120        130        140
                 *          *          *          *          *          *          *
LKP1 hifA    KKDTAMPTPP TINLENCSTT TTTNNKPVAT KVGAYFYSWK NADENNEYTL KNTKSGNDAA QNVNIQTFDA LKP4 hifA    70      180        190        100        110        120        130        -
[ 646 ]      .VN....... ..T.Q..DP. .ANGTANK.N ...L...... .V.KE.NF.. ..EQTTA.Y. T......LMES LKP5 hifA    80      901        100        100        110        120        130        -
[ 618 ]      .GY....... ..T,.G.NAN .G.--..K.N .G......V. ...N...KE.S... ..S.LT.T.K. D......I.QE 150        160        170        180        190        200        210
                 *          *          *          *          *          *          *
LKP1 hifA    NGTDAIRVVG NGTTDFTHSN TNDVATQQTV NKNHISGKAT INGENNVKLH YIARYYATAQ AEAGKVESSV LKP4 hifA140    150        160        170        H T        1901       2001       2101
[ 646 ]      ...K...S... KE.E..M.T. N.G..LN..P .NT......STQ LT.T.ELP.. F..Q....NK .T....Q...

LKP5 hifA140    150        160        1170       T          1180       190        200
[ 618 ]      ......G.AD KTID....K. NGSTNSDKP- T......SATA L.NQGDIA.. ....Q....GM .S...GPT..

*
LKP1 hifA    DFQIAYE*

LKP4 hifA
[ 646 ]      ........

LKP5 hifA210
[ 618 ]      ..P....
```

FIG 1

```
AAGCTTGCATGCCTGCAGGTCGACTCTAGAGGATCATTCCATTGTGTTTTATCTTTTAATAAACACCAAGGT
GAGGTAGAAATATTCAGTTCATCAAGCAAGGATTTTTGCGTAAAACGATCGGCTAATAATCCAAATACATGT
TGATTAACGAAGTTTTTATGATTGCTGAGTAATTCAGTCAAAGGCGTTTTTTCCCAGCGTTCAATTTCCGCC
GTGATGATCGCATTTTCAGGTAAGTCAAAAACTGGCGCATTGAAGGCTAAGGGTTCAACATAAATATCTAAA
GGTGCACCAGCGTAACCTAACATTCTGCCGAGTTGTCCGTTGCCGAGAACATAAACGGTTGGGTATAAGGTG
GAGTTTTGCATAATATTTCTCGTTAAATTTACGAAAAAACAACCGCACTTTAAAAGTGCGGTCAGATCTGAA
GATATTTTTATGTGCGTGGATCGGGATTGTCCAGTACAGCACGAGTTTGGCTTTCACGGAAAGATTGCAAGC
GTGAAAGCAATTCTGCATCCCAACCTGCTAGAATTTGGGCTGCTAACAACCCAGCATTTGCCGCGCCTGCAG
AGCCAATCGCTAATGTTCCGACTGGAATCCCTTTTGGCATTTGCACAATTGAATAAAGGCTATCCACACCAC
TTAACATAGAACTTTTTACTGGCACCCCAGCACTGGCACAAGTGTTTTGGCTGCGATCATACCAGGTAAAT
GTGCCGCACCGCCTGCACCAGCAATAATTACTTTATAGCCATTTTTTTGTGCATTTTCGGCAAATTCGAAAA
GTTTATCAGGCGTACGATGGGCAGAGACGACTTCCACATGATAAGGCACGTTTAATTCATCTAAAATCTGAG
TTGCCTCTTGCATAGTAGCCCAATCACTTTTTGACCCCATCACAACGGCAATTTGTGCAGTTTTTGACATGC
TATTTTCTCAATTTTCTAATTAAAAACGTGGTGTAGAATAGCATAGATTACATATATCGAGCAAACGTTTGC
TATTTATGTACGTATTAATGGGGATTATTTTATAATTATTTGATTTTTAAATTTTAGTAACTATACTTGATA
CCAAATTAATGGGCGATAGTTTATATGGGACGAACTGAAAAATTATTAGATAAGCTCGCACAATCAAAATCT
ACATTTAATTGGAATGAATTAGTTTCTTTGTTAGCTCAACAAGGTTATGAAAAGCGAGAAATGGCAGGTTCT
CGAGTGAGATTTTATAATAGAACACTCGAACATATGATTTTGTTACACAAGCCTCATCCTGAAAATTATATT
AAAGGCGGTGTTTTAAAGTCAGTGAAAGAATCATTAAAACAGGTAGGTATTCTATGAAGTTATTAAATTATA
AAGGTTATGTTGGCACGATTGAGGCGGATTTAGAAAACAATATATTATTTGGCAAACTTGCTTACATTCGTG
ATTTAGTGACTTACGAAGCAGAGTCATTATCTGAGTTAGAAAAAGAATTTCATCAATCTGTTGATTTATATT
TACAAGATTGTTTGGAATTAGGTAAAGAACCGAATAAGCCTTTTAAAGGTGTATTTAATGTACGAATTGGCG
AGGAATTGCATAGAGAAGCAACGATCATAGCTGGCGATCGTTCTCTTAATGCTTTTGTGACGGAAGCAATTA
AAGAAAAATTTTTCGTGAAAAACCAAGTTTAAGATAACAAAACGTATTTACATTTTTTTCATCACGTAGG
CTGGGCGTAAGCCCATGTAGAGACACATAAAAAAGATTTGTAGGCTAGGCGTAAGCTCACGTGGATACATAT
AAAAAAGATTTGTAGGGTGGGCGTAAGCCCACGCAGGATATAACAAACACGTGGGCTTAGATTGCATTACAT
TAGGAATTATTCGTAAGCAATTTGGAAATCAACTGAGGATTCTACTTTACCAGCTTCCGCTTGAGCTGTTGC
        ◄ GluTyrAlaIleGlnPheAspValSerSerGluValLysGlyAlaGluAlaGlnAlaThrAla
ATAGTATCTAGCGATATAGTGTAATTTCACATTGTTTTCACCGTTAATTGTAGCTTTTCCTGAAATATGATT
    ◄ TyrTyrArgAlaIleTyrHisLeuLysValAsnAsnGluGlyAsnIleThrAlaLysGlySerIleHisAsn
TTTATTCACAGTTTGTTGTGTTGCAACGTCATTTGTATTGCTATGCGTAAAATCTGTTGTTCCGTTGCCGAC
    ◄ LysAsnValThrGlnGlnThrAlaValAspAsnThrAsnSerHisThrPheAspThrThrGlyAsnGlyVal
AACTTCAATTGCATCTGTACCATTAGCATCAAAAAGCTGGATATTAACATTCTGTGCAGCATCATTTCCTGA
    ◄ ValGluIleAlaAspThrGlyAsnAlaAspPheLeuGlnIleAsnValAsnGlnAlaAlaAspAsnGlySer
TTTTGTATTTTTTAATGTATATTCATTATTTTCATCTGCATTTTTCCAAGAATAGAAATAAGCTCCAACTTT
    ◄ LysThrAsnLysLeuThrTyrGluAsnAsnGluAspAlaAsnLysTrpSerTyrPheTyrAlaGlyValLys
TGTTGCAACAGGCTTATTATTAGTAGTAGTAGTAGTAGAACAATTTTCTAAATTAATTGTAAATGGTGTTGG
    ◄ ThrAlaValProLysAsnAsnThrThrThrThrSerCysAsnGluLeuAsnIleThrPheProThrPro
```

Figure 2A

```
CATCGCTGTATCTTTTTTAGTTTTTAAATGATTTTTACCCACATCATTTAATACTACGCTCATATTTTTACT
◄ MetAlaThrAspLysLysThrLysLeuHisAsnLysGlyValAspAsnLeuValValSerMetAsnLysSer
ATCCGTTTTCACTTTACAAGTATTCTCAACAACCTTACCAAAGAAAGTAACTTTACCAGATGTTTCAGTACT
◄ AspThrLysValLysCysThrAsnGluValValLysGlyPhePheThrValLysGlySerThrGluThrSer
TACTTGAGGATCAGCAGCATTCGTTGCAAATGCCAATAAAATTAAGCTACCAAGAAGTGTTTTTTTCATAAT
◄ ValGlnProAspAlaAlaAsnThrAlaPheAlaLeuLeuIleLeuSerGlyLeuLeuThrLysLysMetIle
AAATTGCTCCATAAAGAGGTTTGTGCCTTATAAATAAGGCAATAAAGATTAATATAAACCGTTTATTAAAAT
◄ PheGlnGluMet
GCCAAAGGCTTAATAAACAGCAAACTTTGTTTTCCCAAAAAAAGTAAAAAACTCTTCCATTATATATATATA
TATATATAATTAAAGCCCTTTTTGAAAAATTTCATATTTTTTGAATTAATTCGCTGTAGGTTGGGTTTTTG
CCCACATGGAGACATATAAAAAAGATTTGTAGGGTGGGCGTAAGCCCACGCGGAACATCATCAAACAACTGT
AATGTTGTATTAGGCACGGTGGGCTTATGCCTCGCCTACGGGGAAATGAATAAGGATAAATATGGGCTTAGC
                                               ► MetAsnLysAspLysTyrGlyLeuSer
CCAGTTTATGGATTTAATTATGTTGAAATGGGGAAAACAATGTTTAAAAAAACACTTTTATTTTTTACCGCA
► ProValTyrGlyPheAsnTyrValGluMetGlyLysThrMetPheLysLysThrLeuLeuPhePheThrAla
CTATTTTTTGCCGCACTTTGTGCATTTTCAGCCAATGCAGATGTGATTATCACTGGCACCAGAGTGATTTAT
► LeuPhePheAlaAlaLeuCysAlaPheSerAlaAsnAlaAspValIleIleThrGlyThrArgValIleTyr
CCCGCTGGGCAAAAAAATGTTATCGTGAAGTTAGAAAACAATGATGATTCGGCAGCATTGGTGCAAGCCTGG
► ProAlaGlyGlnLysAsnValIleValLysLeuGluAsnAsnAspAspSerAlaAlaLeuValGlnAlaTrp
ATTGATAATGGCAATCCAAATGCCGATCCAAAATACACCAAAACCCCTTTTGTGATTACCCCGCCTGTTGCT
► IleAspAsnGlyAsnProAsnAlaAspProLysTyrThrLysThrProPheValIleThrProProValAla
CGAGTGGAAGCGAAATCAGGGCAAAGTTTGCGGATTACGTTCACAGGCAGCGAGCCTTTACCTGATGATCGC
► ArgValGluAlaLysSerGlyGlnSerLeuArgIleThrPheThrGlySerGluProLeuProAspAspArg
GAAAGCCTCTTTTATTTTAATTTGTTAGATATTCCGCCGAAACCTGATGCGGCATTTCTGGCAAAACACGGC
► GluSerLeuPheTyrPheAsnLeuLeuAspIleProProLysProAspAlaAlaPheLeuAlaLysHisGly
AGCTTTATGCAAATTGCCATTCGCTCACGTTTGAAGTTGTTTTATCGCCCTGCGAAACTCTCGATGGATTCT
► SerPheMetGlnIleAlaIleArgSerArgLeuLysLeuPheTyrArgProAlaLysLeuSerMetAspSer
CGTGATGCAATGAAAAAAGTAGTGTTTAAAGCCACACCTGAAGGGGTGTTGGTGGATAATCAAACCCCTTAT
► ArgAspAlaMetLysLysValValPheLysAlaThrProGluGlyValLeuValAspAsnGlnThrProTyr
TATATGAACTACATTGGTTTGTTACATCAAAATAAACCTGCGAAAAATGTCAAAATGGTTGCCCCTTTTTCT
► TyrMetAsnTyrIleGlyLeuLeuHisGlnAsnLysProAlaLysAsnValLysMetValAlaProPheSer
CAAGCGGTATTTGAAGCCAAAGGCGTGCGTTCTGGCGATAAATTGAAATGGGTATTGGTTAATGATTACGGT
► GlnAlaValPheGluAlaLysGlyValArgSerGlyAspLysLeuLysTrpValLeuValAsnAspTyrGly
GCCGACCAAGAAGGCGAAGCCATCGCTCAATAATAGCGAACTAGTGTAGGGTGGGCTTTAGACCACCGATTA
► AlaAspGlnGluGlyGluAlaIleAlaGln
ACCATAACAAAGGTGGGCTGAAGCCCACCCTACAACCACAAAGAACGATTAATCTGTGAAAACAAAAATTTT
TCCCTTAAATAAAATTGCGTTTGCTTGTTCACTGCTATTGGCAAATCCTTTAGCGTGGGCGGGAGATCAATT
TGATGCCTCTCTTTGGGGAGATGGTTCGGTGTTGGGCGTTGATTTTGCCCGATTTAATGTAAAAAATGCCGT
GTTACCAGGGCGTTATGAAGCTCAAATCTATGTGAAATTTGAAGAAAAGGCGTAAGCGATATTATTTTTGC
```

Figure 2B

```
TGATAATCCTGCCACAGGTCGGACAGAATTATGCTTTACGCCTAAACTTCAAGAAATGCTGGATTTGATGGA
                                                          ▸ MetLeuAspLeuMetAs
TGAAGCCATTGTGAAATCGCCCAATTCAGAAGATGACACTTGTGTCTTTGCTTCTGATGCTATTCCTAAAGG
▸ pGluAlaIleValLysSerProAsnSerGluAspAspThrCysValPheAlaSerAspAlaIleProLysGl
CACGTTTGAATATCAAAGCGGCGAAATGAAATTGAAACTTGAGCTCCCTCAAGCTCTCACTATTCGCCGACC
▸ yThrPheGluTyrGlnSerGlyGluMetLysLeuLysLeuGluLeuProGlnAlaLeuThrIleArgArgPr
AAGAGGCTATATTGCGCCATCTCGCTGGCAAACTGGCACCAATGCCGCTTTTGCAAATTACGATATCAACTA
▸ oArgGlyTyrIleAlaProSerArgTrpGlnThrGlyThrAsnAlaAlaPheAlaAsnTyrAspIleAsnTy
TTATCGTTCTGGTAATCCCGAAGTAAAATCCGAAAGTTTGTATGTGGGCTTGCGTAGTGGCGTAAATTTTGG
▸ rTyrArgSerGlyAsnProGluValLysSerGluSerLeuTyrValGlyLeuArgSerGlyValAsnPheGl
CAACTGGGCATTGCGTCATAGCGGCAGTTTTAGCCGTTTTGAAAACCAAAGTAGCTCGGGTTTTACTGATAA
▸ yAsnTrpAlaLeuArgHisSerGlySerPheSerArgPheGluAsnGlnSerSerSerGlyPheThrAspLy
GGGCAAAAATCATTACGAACGTGGCGATACCTATTTACAACGAGATTTCGCCCTGCTTCGTGGCAATGTCAC
▸ sGlyLysAsnHisTyrGluArgGlyAspThrTyrLeuGlnArgAspPheAlaLeuLeuArgGlyAsnValTh
TGTTGGGGATTTTTTCAGCACTGCCCGCATTGGCGAAAATTTTGGTATGCGTGGTTTGCGTATTGCCTCTGA
▸ rValGlyAspPhePheSerThrAlaArgIleGlyGluAsnPheGlyMetArgGlyLeuArgIleAlaSerAs
TGATAGAATGCTTGCCCCATCACAACGTGGTTTTGCCCCAGTGGTGCGTGGCGTGGCAAACACAAACGCCAA
▸ pAspArgMetLeuAlaProSerGlnArgGlyPheAlaProValValArgGlyValAlaAsnThrAsnAlaLy
AGTCAGCATCAAACAAAATGGCTATACGATTTATCAAATCACCGTTCCCGCAGGGCCTTTCGTGATTAACGA
▸ sValSerIleLysGlnAsnGlyTyrThrIleTyrGlnIleThrValProAlaGlyProPheValIleAsnAs
TTTGTATGCCAGCGGTTATAGCGGCGATTTAACGGTGGAAATCCAAGAAAGTGATGGTAAAGTGCGGTCATT
▸ pLeuTyrAlaSerGlyTyrSerGlyAspLeuThrValGluIleGlnGluSerAspGlyLysValArgSerPh
TATTGTGCCGTTTTCTAATCTTGCCCCGTTAATGCGTGTGGGGCATTTGCGTTATCAATTAGCTGGCGGACG
▸ eIleValProPheSerAsnLeuAlaProLeuMetArgValGlyHisLeuArgTyrGlnLeuAlaGlyGlyAr
TTATCGAATTGACAGCCGCACCTTTGATGAACGTGTGTTACAAGGCGTGTTGCAATATGGTTTAACTAATCA
▸ gTyrArgIleAspSerArgThrPheAspGluArgValLeuGlnGlyValLeuGlnTyrGlyLeuThrAsnHi
TCTCACGCTGAATTCAAGCCTGCTTTATACACGTCATTATCGTGCAGGGCTGTTTGGTTTTGGTTTAAATAC
▸ sLeuThrLeuAsnSerSerLeuLeuTyrThrArgHisTyrArgAlaGlyLeuPheGlyPheGlyLeuAsnTh

GCCGATTGGGGCGTTTTCTGCTGATGCCACTTGGTCGCACGCTGAATTTCCGCTAAAACATGTGAGCAAAAA
▸ rProIleGlyAlaPheSerAlaAspAlaThrTrpSerHisAlaGluPheProLeuLysHisValSerLysAs
CGGCTACAGCTTGCACGGCAGTTATAGTATTAACTTCAATGAAAGTGGCACCAATATCACGTTGGCAGCCTA
▸ nGlyTyrSerLeuHisGlySerTyrSerIleAsnPheAsnGluSerGlyThrAsnIleThrLeuAlaAlaTy
TCGCTATTCTTCACGGGATTTTTACACCTTAAGCGACACCATTGGTCTTAACCGCACTTTCAGACAATTTAG
▸ rArgTyrSerSerArgAspPheTyrThrLeuSerAspThrIleGlyLeuAsnArgThrPheArgGlnPheSe
CGGTGCGTATTTGCCTGAAATTTACCGCCCAAAAAATCAGTTTCAAGTGAGTTTAAGCCAAAGTCTGGGGAA
▸ rGlyAlaTyrLeuProGluIleTyrArgProLysAsnGlnPheGlnValSerLeuSerGlnSerLeuGlyAs
TTGGGGAAATCTCTATCTTTCAGGACAAACCTATAATTATTGGGAAAAACGTGGCACGAATACGCAATATCA
▸ nTrpGlyAsnLeuTyrLeuSerGlyGlnThrTyrAsnTyrTrpGluLysArgGlyThrAsnThrGlnTyrGl
```

Figure 2C

```
AGTTGCCTATTCAAACAGCTTCCACATTCTTAATTACTCTGTAAACCTCTCACAGAGTATTGATAAAGAAAC
▶ nValAlaTyrSerAsnSerPheHisIleLeuAsnTyrSerValAsnLeuSerGlnSerIleAspLysGluTh
GGGCAAACGTGACAACAGCATTTATTTAAGTCTCAGCCTGCCATTAGGCGATAACCATTCTGCAGATAGTAG
▶ rGlyLysArgAspAsnSerIleTyrLeuSerLeuSerLeuProLeuGlyAspAsnHisSerAlaAspSerSe
TTATTCTCGCAGTGGTAACGATATTAACCAACGACTTGGCGTAAATGGCTCTTTTGGTGAACGTCATCAATG
▶ rTyrSerArgSerGlyAsnAspIleAsnGlnArgLeuGlyValAsnGlySerPheGlyGluArgHisGlnTr
GAGTTATGGTATTAACGCTTCACGCAATAATCAAGGCTATCGCAGTTATGACGGTAATCTTTCGCATAACAA
▶ pSerTyrGlyIleAsnAlaSerArgAsnAsnGlnGlyTyrArgSerTyrAspGlyAsnLeuSerHisAsnAs
TAGCATTGGTAGTTACCGTGCTTCTTATTCACGTGATAGCCTCAAAAATCGCTCCATCTCACTGGGCGCAAG
▶ nSerIleGlySerTyrArgAlaSerTyrSerArgAspSerLeuLysAsnArgSerIleSerLeuGlyAlaSe
CGGTGCTGTCGTGGCGCACAAACACGGTATTACCTTAAGCCAACCTGTTGGCGAAAGTTTTGCCATTATTCA
▶ rGlyAlaValValAlaHisLysHisGlyIleThrLeuSerGlnProValGlyGluSerPheAlaIleIleHi
CGCCAAAGATGCCGCAGGAGCAAAAGTGGAATCAGGTGCCAATGTGAGCCTTGATTATTTCGGCAATGCGGT
▶ sAlaLysAspAlaAlaGlyAlaLysValGluSerGlyAlaAsnValSerLeuAspTyrPheGlyAsnAlaVa
TATGCCTTACACCAGCCCGTATGAAATCAATTATATCGGTATCAATCCATCTGATGCGGAGGCGAATGTGGA
▶ lMetProTyrThrSerProTyrGluIleAsnTyrIleGlyIleAsnProSerAspAlaGluAlaAsnValGl
ATTTGAAGCCACTGAACGCCAAATCATTCCTCGTGCAAATTCAATTAGCTTAGTAGATTTCCGCACGGGCAA
▶ uPheGluAlaThrGluArgGlnIleIleProArgAlaAsnSerIleSerLeuValAspPheArgThrGlyLy
AAATACAATGGTGTTATTTAACCTCACTTTGCCAAATGGCGAGCCAGTGCCAATGGCATCCACCGCACAAGA
▶ sAsnThrMetValLeuPheAsnLeuThrLeuProAsnGlyGluProValProMetAlaSerThrAlaGlnAs
TAGCGAAGGGGCATTTGTGGGCGATGTGGTGCAAGGTGGTGTGCTTTTCGCTAATAAACTTACCCAGCCAAA
▶ pSerGluGlyAlaPheValGlyAspValValGlnGlyGlyValLeuPheAlaAsnLysLeuThrGlnProLy
AGGCGAGTTAATCGTCAAATGGGGTGAGCGAGAAAGCGAACAATGCCGTTTCCAATATCAAGTTGATTTGGA
▶ sGlyGluLeuIleValLysTrpGlyGluArgGluSerGluGlnCysArgPheGlnTyrGlnValAspLeuAs
TAACGCACAAATACAAAGTCACGATATTCAATGCAAAACCGCAAAATAAATAATTGAAGAGGATTTATGCAA
▶ pAsnAlaGlnIleGlnSerHisAspIleGlnCysLysThrAlaLys                    ▶ MetGln
AAAACACCCAAAAAATTAACCGCGCTTTTCCATCAAAATCCACTGCTACTTGTAGTGGAGCAAATTATAGT
▶ LysThrProLysLysLeuThrAlaLeuPheHisGlnLysSerThrAlaThrCysSerGlyAlaAsnTyrSer
GGAGCAAATTATAGTGGCTCAAAATGCTTTAGGTTTCATCGTCTGGCTCTGCTTGCTTGCGTGGCTCTGCTT
▶ GlyAlaAsnTyrSerGlySerLysCysPheArgPheHisArgLeuAlaLeuLeuAlaCysValAlaLeuLeu
GATTGCATTGTGGCACTGCCTGCTTATGCTTACGATGGCAGAGTGACCTTTCAAGGGGAGATTTTAAGTGAT
▶ AspCysIleValAlaLeuProAlaTyrAlaTyrAspGlyArgValThrPheGlnGlyGluIleLeuSerAsp
GGCACTTGTAAAATTGAAACAGACAGCCAAAATCGCACGGTTACCCTGCCAACAGTGGGAAAAGCTAATTTA
▶ GlyThrCysLysIleGluThrAspSerGlnAsnArgThrValThrLeuProThrValGlyLysAlaAsnLeu
AGCCACGCAGGGCAAACCGCCGCCCTGTGCCTTTTTCCATCACGTTAAAAGAATGCAATGCAGATGATGCT
▶ SerHisAlaGlyGlnThrAlaAlaProValProPheSerIleThrLeuLysGluCysAsnAlaAspAspAla
ATGAAAGCTAATCTGCTATTTAAAGGGGAGACAACACAACAGGGCAATCTTATCTTTCCAATAAGGCAGGC
▶ MetLysAlaAsnLeuLeuPheLysGlyGlyAspAsnThrThrGlyGlnSerTyrLeuSerAsnLysAlaGly
```

Figure 2D

```
AACGGCAAAGCCACCAACGTGGGCATTCAAATTGTCAAAGCCGATGGCATAGGCACGCCTATCAAGGTGGAC
▶ AsnGlyLysAlaThrAsnValGlyIleGlnIleValLysAlaAspGlyIleGlyThrProIleLysValAsp
GGCACCGAAGCCAACAGCGAAAAAGCCCCGACACAGGTAAAGCGCAAAACGGCACAGTTATTCAACCCCGT
▶ GlyThrGluAlaAsnSerGluLysAlaProAspThrGlyLysAlaGlnAsnGlyThrValIleGlnProArg
TTTGGCTACTTTGGCTCGTTATTACGCCACAGGTGAAGCCACCGCAGGCGACGTTGAAGCCACTGCAACTTT
▶ PheGlyTyrPheGlySerLeuLeuArgHisArg
TGAAGTGCAGTATAACTAAAATATTTATTATCCAGTGAAAAAATGAATAAGAAATCGTATATAAATCATTAC
                                              ▶ MetAsnLysLysSerTyrIleAsnHisTyr

TTAACTTTATTTAAAGTTACTACTTTACTATTTACTCTTTCAAGTAATCCTGTATGGGCAAATATAAAAACA
▶ LeuThrLeuPheLysValThrThrLeuLeuPheThrLeuSerSerAsnProValTrpAlaAsnIleLysThr
GTTCAGGGAACAACTAGTGGTTTTCCACTTCTAACAAGAACTTTCACATTTAATGGCAATTTGCAATGGAAT
▶ ValGlnGlyThrThrSerGlyPheProLeuLeuThrArgThrPheThrPheAsnGlyAsnLeuGlnTrpAsn
GTGAGTGCTCTACAACCAGCTTATATTGTTTCCTCTCAAGCAAGAGATAATCTTGATACAGTACATATTCAA
▶ ValSerAlaLeuGlnProAlaTyrIleValSerSerGlnAlaArgAspAsnLeuAspThrValHisIleGln
TCTTCTGAAATTAATGCTCCAACAAATTCATTAGCTCCATTTAATAATTGGATTAATACGAAATCAGCAGTA
▶ SerSerGluIleAsnAlaProThrAsnSerLeuAlaProPheAsnAsnTrpIleAsnThrLysSerAlaVal
GAGCTAGGTTATAGCTTTGCGGGCATTACTTGTACTAGTAATCCTTGCCCAACAATGAAATTACCATTATTA
▶ GluLeuGlyTyrSerPheAlaGlyIleThrCysThrSerAsnProCysProThrMetLysLeuProLeuLeu
TTTCATCCTGATCTTACTAATTTAACTCCACCTGGAAAGAAAAATTCTGATGGAGGGGAGATTTTTAAATTA
▶ PheHisProAspLeuThrAsnLeuThrProProGlyLysLysAsnSerAspGlyGlyGluIlePheLysLeu
CATAATGAATCTAATTTAGGCGTCTCTTTTCAAATTGGAGTAAAAACGAATACTTCTCTAGATTGGGTTAAT
▶ HisAsnGluSerAsnLeuGlyValSerPheGlnIleGlyValLysThrAsnThrSerLeuAspTrpValAsn
GCTAAGAATAATTTTAGCTCTCTAAAAGTTTTAATGGTGCCTTTTAATTCTAGCGATAAAATATCTTTGCAT
▶ AlaLysAsnAsnPheSerSerLeuLysValLeuMetValProPheAsnSerSerAspLysIleSerLeuHis
TTACGTGCTAAATTTCATTTATTAACAGATTTTTCATCGCTAAATAATGATATTACTATTGACCCTATGAAT
▶ LeuArgAlaLysPheHisLeuLeuThrAspPheSerSerLeuAsnAsnAspIleThrIleAspProMetAsn
ACTAGTATAGGCAAAATTAATCTTGAAACGTGGCGTGGCTCAACAGGCAATTTTTCTGTTAAATATGTAGGT
▶ ThrSerIleGlyLysIleAsnLeuGluThrTrpArgGlySerThrGlyAsnPheSerValLysTyrValGly
GAGGATAAGGGAGATATATCTATTTTCTTTAATACACCTAAAATTATTCTAAAAAAACAACAACGCCGATGT
▶ GluAspLysGlyAspIleSerIlePhePheAsnThrProLysIleIleLeuLysLysGlnGlnArgArgCys
ACTCTGAATAATGCTCCAGTGAGCCCAAATCCAGTTAAATTACGAGCGGTAAAAAAACGTGAATTGGAGGCA
▶ ThrLeuAsnAsnAlaProValSerProAsnProValLysLeuArgAlaValLysLysArgGluLeuGluAla
CAAAGTGAAATGGAAGGTGGGACATTTCAGTTAAGAGTAAATTGTGACAATACCACTTATAATAAAGCCAAC
▶ GlnSerGluMetGluGlyGlyThrPheGlnLeuArgValAsnCysAspAsnThrThrTyrAsnLysAlaAsn
GGCAAATGGTTATTTCCTGTAGTGAAAGTTACTTTTACGGACGAAGATGGTACAACGAATAATGGAACAAAT
▶ GlyLysTrpLeuPheProValValLysValThrPheThrAspGluAspGlyThrThrAsnAsnGlyThrAsn
```

Figure 2E

```
GACTTACTTCGCACCCAAACAGGCAGCGGACAAGCCACAGGCGTTAGCTTAAGAATCAAACGAGAAAATGGT
```
▸ AspLeuLeuArgThrGlnThrGlySerGlyGlnAlaThrGlyValSerLeuArgIleLysArgGluAsnGly
```
ACAGAAACCGTAAAATACGGTGCTGATTCTGCTCAAATGGGGAATGCTGGACAATTTGAATTACGAAAACAA
```
▸ ThrGluThrValLysTyrGlyAlaAspSerAlaGlnMetGlyAsnAlaGlyGlnPheGluLeuArgLysGln
```
CCATCCCCTGCTGGTGGAGATCAATATGCTGAAGAAACTTTCAAAGTCTATTACGTAAAAGACTCAACAAGA
```
▸ ProSerProAlaGlyGlyAspGlnTyrAlaGluGluThrPheLysValTyrTyrValLysAspSerThrArg
```
GGCACCTTAATCGAAGGAAAAGTCAAAGCCGCCGCCACTTTCACAATGTCATATCAATAATAATGTCGGGTG
```
▸ GlyThrLeuIleGluGlyLysValLysAlaAlaAlaThrPheThrMetSerTyrGln
```
GGAATATAAAGGCTGAAGGTTTAAACTTCAGTCTTTTTTTATAGGAAAATACCATTGCAACTTTAAGGATAA
AATTTTATCCTAAGCACAATTTTTATAAGAATAGGTCAAATTATGTTAGCCAAAGCAAAATATAGAAAAGAT
```
                                                                                 ▸ MetLeuAlaLysAlaLysTyrArgLysAsp
```
TACAAACAACCAGATTTTACGGTCACAGACATTTATTTAGATTTTCAACTTGATCCTAAAAATACTGTGGTG
```
▸ TyrLysGlnProAspPheThrValThrAspIleTyrLeuAspPheGlnLeuAspProLysAsnThrValVal

```
ACTGCAACCACAAAATTCCAACGCTTAAATAATGAAGCGACGTCTTTACGTTTAGACGGGCATAGCTTCCAG
```
▸ ThrAlaThrThrLysPheGlnArgLeuAsnAsnGluAlaThrSerLeuArgLeuAspGlyHisSerPheGln
```
TTTTCTTCTATTAAATTTAATGGCGAGCCATTTTCTGATTATCAACAAGATGGCGAGAGTTTAACGCTCGAT
```
▸ PheSerSerIleLysPheAsnGlyGluProPheSerAspTyrGlnGlnAspGlyGluSerLeuThrLeuAsp
```
TTAAAAGACAAAAGTGCGGATGAATTTGAGCTTGAAATTGTGACGTTCCTTGTGCCAGCCGAAAATACGTCA
```
▸ LeuLysAspLysSerAlaAspGluPheGluLeuGluIleValThrPheLeuValProAlaGluAsnThrSer
```
TTACAAGGGCTATATCAGTCTGGCGAAGGTATTTGTACGCAATGTGAGGCGGAAGGTTTCCGTCAAATCACT
```
▸ LeuGlnGlyLeuTyrGlnSerGlyGluGlyIleCysThrGlnCysGluAlaGluGlyPheArgGlnIleThr
```
TATATGCTTGATCGTCCTGATGTGCTGGCGCGTTATATAATCAAAATTACGGCAGATAAAACCAAATATCCA
```
▸ TyrMetLeuAspArgProAspValLeuAlaArgTyrIleIleLysIleThrAlaAspLysThrLysTyrPro
```
TTCTTACTGTCGAATGGTAATCGCATTGCAAGTGGCGAATTAGAAGATGGTCGCCATTGGGTGGAATGGAAT
```
▸ PheLeuLeuSerAsnGlyAsnArgIleAlaSerGlyGluLeuGluAspGlyArgHisTrpValGluTrpAsn
```
GATCCTTTCCCAAAACCAAGCTATTTATTTGCTTTAGTGGCGGGAGATTNNGGTTTATTACAAGATAANTTT
```
▸ AspProPheProLysProSerTyrLeuPheAlaLeuValAlaGlyAspXaaGlyLeuLeuGlnAspXaaPhe
```
ATTACTAAAAGTGGTCGTGAAGTGGCTTTAGAGCTTTATGTGGATCGCGGTAATCTTAACCGTGCAACTGGG
```
▸ IleThrLysSerGlyArgGluValAlaLeuGluLeuTyrValAspArgGlyAsnLeuAsnArgAlaThrGly
```
GCAATGGAAAGTCTGAAAAAAGCGATGAAATGGGATGAAGATCGCTTTATTTTAGAATTTTACCTAGATATT
```
▸ AlaMetGluSerLeuLysLysAlaMetLysTrpAspGluAspArgPheIleLeuGluPheTyrLeuAspIle
```
TATATGATCGCGGCCGCCGATTCCTCCAATATGGGCGCAATGGAAAATAAAGGATTAAATATCTTTAACTCT
```
▸ TyrMetIleAlaAlaAlaAspSerSerAsnMetGlyAlaMetGluAsnLysGlyLeuAsnIlePheAsnSer
```
AAATTGGTGTTGGCAAATCCACAAACGGCAACAGATGAAGATTATCTTGTCATTGAAAGTGTGATTGCACAC
```
▸ LysLeuValLeuAlaAsnProGlnThrAlaThrAspGluAspTyrLeuValIleGluSerValIleAlaHis

Figure 2F

GAATATTCCCATAACTGGACGGGAAACCGTGTAACCCGCCGAGATGGGTTCAACTAGGTTTGAAGAAGGTTA
► GluTyrSerHisAsnTrpThrGlyAsnArgValThrArgArgAspGlyPheAsn
ACGGCTTCCGGGAACAAGATTTCTCAGATCAGTTCTCCGGGCCGGAACCGATTAATAAGGGAAAATTTTCCG

Figure 2G

CLJ11

CLJ10

CLJ12

KIEEGKLVIWINGDKGYNGLAEVGKKFEKDTGIKVTVEHPDKLEEKFPQVAATGDGPDIIF
WAHDRFGGYAQSGLLAEITPDKAFQDKLYPFTWDAVRYNGKLIAYPIAVEALSLIYNKDLL
PNPPKTWEEIPALDKELKAKGKSALMFNLQEPYFTWPLIAADGGYAFKYENGKYDKIKDVG
VDNAGAKAGLTFLVDLIKNKHMNADTDYSIAEAAFNKGETAMTINGPWAWSNIDTSKVN
YGVTVLPTFKGQPSKPFVGVLSAGINAASPNKELAKEFLENYLLTDEGLEAVNKDKPLGA
VALKSYEEELAKDPRIAATMENAQKGEIMPNIPQMSAFWYAVRTAVINAASGRQTVDEALK
DAQTRITKIEGR<u>TLSSNPVWANIKTVQGTTSGFPLLTRTFTENGNLQWNVSALQPAYIVSSQ
ARDNLDTVHIQSSEINAPTNSLAPENNWINTKSAVELGYSFAGITCTSNPCPTMKLPLLFHP
QLTNLTPPGKKNSDGGEIFKLHNESNLGVSFQIGVKTNTSLDWVNAKNNFSSLKVLMVPF
NSSKSISLHLRAKFHLLTDFSSLNNDITIDPMNTSIGKINLETWRGSTGNFSVKYVGEDKG
DISIFFNTPKIILKKQQRRCTLNNAPVSPNPVKLRAVKKRELEAQSEMEGGTFQLRVNCDN
TTYNKAN</u>

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 217 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met Glu Gln Phe Ile Met Lys Lys Thr Thr Thr Gly Ser Leu Ile Leu
 1               5                  10                  15
Leu Ala Phe Ala Thr Asn Ala Ala Asp Pro Gln Val Ser Thr Glu Thr
             20                  25                  30
Ser Gly Lys Val Thr Phe Phe Gly Lys Val Val Glu Asn Thr Cys Lys
         35                  40                  45
Val Lys Thr Asp Ser Lys Asn Met Ser Val Val Leu Asn Asp Val Gly
     50                  55                  60
Lys Asn His Leu Lys Thr Lys Lys Asp Thr Ala Met Pro Thr Pro Phe
 65                  70                  75                  80
Thr Ile Asn Leu Glu Asn Cys Ser Thr Thr Thr Thr Asn Asn Lys
                 85                  90                  95
Pro Val Ala Thr Lys Val Gly Ala Tyr Phe Tyr Ser Trp Lys Asn Ala
            100                 105                 110
Asp Glu Asn Asn Glu Tyr Thr Leu Lys Asn Thr Lys Ser Gly Asn Asp
            115                 120                 125
Ala Ala Gln Asn Val Asn Ile Gln Thr Phe Asp Ala Asn Gly Thr Asp
        130                 135                 140
Ala Ile Glu Val Val Gly Asn Gly Thr Thr Asp Phe Thr His Ser Asn
145                 150                 155                 160
Thr Asn Asp Val Ala Thr Gln Gln Thr Val Asn Lys Asn His Ile Ser
                165                 170                 175
Gly Lys Ala Thr Ile Asn Gly Glu Asn Asn Val Lys Leu His Tyr Ile
                180                 185                 190
Ala Arg Tyr Tyr Ala Thr Ala Gln Ala Glu Ala Gly Lys Val Glu Ser
            195                 200                 205
Ser Val Asp Phe Gln Ile Ala Tyr Glu
        210                 215
```

( 2 ) INFORMATION FOR SEQ ID NO:2:

( i ) SEQUENCE CHARACTERISTICS:
        ( A ) LENGTH: 216 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Met Glu Gln Phe Ile Met Lys Lys Thr Leu Leu Gly Ser Leu Ile Leu
 1               5                  10                  15
Leu Ala Phe Ala Gly Asn Val Gln Ala Asp Ile Asn Thr Glu Thr Ser
             20                  25                  30
```

Gly Lys Val Thr Phe Phe Gly Lys Val Val Glu Asn Thr Cys Lys Val
          35                  40                  45
Lys Thr Glu His Lys Asn Leu Ser Val Val Leu Asn Asp Val Gly Lys
     50                  55                  60
Asn Ser Leu Ser Thr Lys Val Asn Thr Ala Met Pro Thr Pro Phe Thr
65                  70                  75                  80
Ile Thr Leu Gln Asn Cys Asp Pro Thr Thr Ala Asn Gly Thr Ala Asn
                 85                  90                  95
Lys Ala Asn Lys Val Gly Leu Tyr Phe Tyr Ser Trp Lys Asn Val Asp
             100                 105                 110
Lys Glu Asn Asn Phe Thr Leu Lys Glu Gln Thr Thr Ala Asn Asp Tyr
             115                 120                 125
Ala Thr Asn Val Asn Ile Gln Leu Met Glu Ser Asn Gly Thr Lys Ala
         130                 135                 140
Ile Ser Val Val Gly Lys Glu Thr Glu Asp Phe Met His Thr Asn Asn
145                 150                 155                 160
Asn Gly Val Ala Leu Asn Gln Thr Pro Asn Asn Thr His Ile Ser Gly
                 165                 170                 175
Ser Thr Gln Leu Thr Gly Thr Asn Glu Leu Pro Leu His Phe Ile Ala
             180                 185                 190
Gln Tyr Tyr Ala Thr Asn Lys Ala Thr Ala Gly Lys Val Gln Ser Ser
         195                 200                 205
Val Asp Phe Gln Ile Ala Tyr Glu
         210                 215

( 2 ) INFORMATION FOR SEQ ID NO:3:

( i ) SEQUENCE CHARACTERISTICS:
         ( A ) LENGTH: 214 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:3:

Met Glu Gln Phe Ile Met Lys Lys Thr Leu Leu Gly Ser Leu Ile Leu
1               5                  10                  15
Leu Ala Phe Ala Gly Asn Val Gln Ala Ala Asp Pro Asn Pro Glu Thr
             20                  25                  30
Lys Gly Lys Val Thr Phe Tyr Gly Lys Val Val Glu Asn Thr Cys Lys
         35                  40                  45
Val Lys Ser Gly Asn Arg Asp Met Ser Val Val Leu Asn Asp Val Gly
     50                  55                  60
Lys Ala His Leu Ser Gln Lys Gly Tyr Thr Ala Met Pro Thr Pro Phe
65                  70                  75                  80
Thr Ile Thr Leu Glu Gly Cys Asn Ala Asn Thr Gly Thr Lys Pro Lys
                 85                  90                  95
Ala Asn Lys Val Gly Val Tyr Phe Tyr Ser Trp Asn Asn Ala Asp Lys
             100                 105                 110
Glu Asn Ser Tyr Thr Leu Lys Ser Thr Leu Thr Gly Thr Asp Lys Ala
             115                 120                 125
Asp Asn Val Asn Ile Gln Ile Phe Gln Glu Asn Gly Thr Asp Ala Ile
         130                 135                 140
Gly Val Ala Asp Lys Thr Ile Asp Asp Phe Thr His Lys Asn Asn Gly
145                 150                 155                 160

| | | | | | | | | | | | | | | |
|---|---|---|---|---|---|---|---|---|---|---|---|---|---|---|
| Ser | Thr | Asn | Ser | Asp<br>165 | Lys | Pro | Thr | Lys | Asn<br>170 | His | Ile | Ser | Ser | Ala<br>175 | Thr |
| Ala | Leu | Asn | Asn<br>180 | Gln | Asp | Gly | Ile | Ala<br>185 | Leu | His | Tyr | Ile | Ala<br>190 | Gln | Tyr |
| Tyr | Ala | Thr<br>195 | Gly | Met | Ala | Ser | Ala<br>200 | Gly | Lys | Gly | Pro | Thr<br>205 | Ser | Val | Asp |
| Phe | Pro | Ile<br>210 | Ala | Tyr | Glu | | | | | | | | | | |

( 2 ) INFORMATION FOR SEQ ID NO:4:

( i ) SEQUENCE CHARACTERISTICS:
        ( A ) LENGTH: 9432 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: complement (1882..2532)

( i x ) FEATURE:
        ( A ) NAME/KEY: CDS
        ( B ) LOCATION: 2854..3630

( i x ) FEATURE:
        ( A ) NAME/KEY: CDS
        ( B ) LOCATION: 4016..6238

( i x ) FEATURE:
        ( A ) NAME/KEY: CDS
        ( B ) LOCATION: 6259..6873

( i x ) FEATURE:
        ( A ) NAME/KEY: CDS
        ( B ) LOCATION: 6955..8265

( i x ) FEATURE:
        ( A ) NAME/KEY: CDS
        ( B ) LOCATION: 8395..9342

( x i ) SEQUENCE DESCRIPTION: SEQ ID NO:4:

| | | | | | | |
|---|---|---|---|---|---|---|
| AAGCTTGCAT | GCCTGCAGGT | CGACTCTAGA | GGATCATTCC | ATTGTGTTTT | ATCTTTTAAT | 60 |
| AAACACCAAG | GTGAGGTAGA | AATATTCAGT | TCATCAAGCA | AGGATTTTTG | CGTAAAACGA | 120 |
| TCGGCTAATA | ATCCAAATAC | ATGTTGATTA | ACGAAGTTTT | TATGATTGCT | GAGTAATTCA | 180 |
| GTCAAAGGCG | TTTTTTCCCA | GCGTTCAATT | TCCGCCGTGA | TGATCGCATT | TTCAGGTAAG | 240 |
| TCAAAAACTG | GCGCATTGAA | GGCTAAGGGT | TCAACATAAA | TATCTAAAGG | TGCACCAGCG | 300 |
| TAACCTAACA | TTCTGCCGAG | TTGTCCGTTG | CCGAGAACAT | AAACGGTTGG | GTATAAGGTG | 360 |
| GAGTTTTGCA | TAATATTTCT | CGTTAAATTT | ACGAAAAAAC | AACCGCACTT | TAAAAGTGCG | 420 |
| GTCAGATCTG | AAGATATTTT | TATGTGCGTG | GATCGGGATT | GTCCAGTACA | GCACGAGTTT | 480 |
| GGCTTTCACG | GAAAGATTGC | AAGCGTGAAA | GCAATTCTGC | ATCCAACCT | GCTAGAATTT | 540 |
| GGGCTGCTAA | CAACCCAGCA | TTTGCCGCGC | CTGCAGAGCC | AATCGCTAAT | GTTCCGACTG | 600 |
| GAATCCCTTT | TGGCATTTGC | ACAATTGAAT | AAAGGCTATC | CACACCACTT | AACATAGAAC | 660 |
| TTTTTACTGG | CACCCCCAGC | ACTGGCACAA | GTGTTTTGGC | TGCGATCATA | CCAGGTAAAT | 720 |
| GTGCCGCACC | GCCTGCACCA | GCAATAATTA | CTTTATAGCC | ATTTTTTTGT | GCATTTTCGG | 780 |
| CAAATTCGAA | AAGTTTATCA | GGCGTACGAT | GGGCAGAGAC | GACTTCACA | TGATAAGGCA | 840 |
| CGTTTAATTC | ATCTAAAATC | TGAGTTGCCT | CTTGCATAGT | AGCCCAATCA | CTTTTTGACC | 900 |
| CCATCACAAC | GGCAATTTGT | GCAGTTTTTG | ACATGCTATT | TTCTCAATTT | TCTAATTAAA | 960 |

```
AACGTGGTGT AGAATAGCAT AGATTACATA TATCGAGCAA ACGTTTGCTA TTTATGTACG      1020

TATTAATGGG GATTATTTTA TAATTATTTG ATTTTTAAAT TTTAGTAACT ATACTTGATA      1080

CCAAATTAAT GGGCGATAGT TTATATGGGA CGAACTGAAA AATTATTAGA TAAGCTCGCA      1140

CAATCAAAAT CTACATTTAA TTGGAATGAA TTAGTTTCTT TGTTAGCTCA ACAAGGTTAT      1200

GAAAAGCGAG AAATGGCAGG TTCTCGAGTG AGATTTTATA ATAGAACACT CGAACATATG      1260

ATTTTGTTAC ACAAGCCTCA TCCTGAAAAT TATATTAAAG GCGGTGTTTT AAAGTCAGTG      1320

AAAGAATCAT TAAAACAGGT AGGTATTCTA TGAAGTTATT AAATTATAAA GGTTATGTTG      1380

GCACGATTGA GGCGGATTTA GAAAACAATA TATTATTTGG CAAACTTGCT TACATTCGTG      1440

ATTTAGTGAC TTACGAAGCA GAGTCATTAT CTGAGTTAGA AAAAGAATTT CATCAATCTG      1500

TTGATTTATA TTTACAAGAT TGTTTGGAAT TAGGTAAAGA ACCGAATAAG CCTTTTAAAG      1560

GTGTATTTAA TGTACGAATT GGCGAGGAAT TGCATAGAGA AGCAACGATC ATAGCTGGCG      1620

ATCGTTCTCT TAATGCTTTT GTGACGGAAG CAATTAAAGA AAAAATTTTT CGTGAAAAAC      1680

CAAGTTTAAG ATAACAAAAC GTATTTACAT TTTTTTTCAT CACGTAGGCT GGGCGTAAGC      1740

CCATGTAGAG ACACATAAAA AAGATTTGTA GGCTAGGCGT AAGCTCACGT GGATACATAT      1800

AAAAAAGATT TGTAGGGTGG GCGTAAGCCC ACGCAGGATA TAACAAACAC GTGGGCTTAG      1860

ATTGCATTAC ATTAGGAATT ATTCGTAAGC AATTTGGAAA TCAACTGAGG ATTCTACTTT      1920

ACCAGCTTCC GCTTGAGCTG TTGCATAGTA TCTAGCGATA TAGTGTAATT TCACATTGTT      1980

TTCACCGTTA ATTGTAGCTT TTCCTGAAAT ATGATTTTTA TTCACAGTTT GTTGTGTTGC      2040

AACGTCATTT GTATTGCTAT GCGTAAAATC TGTTGTTCCG TTGCCGACAA CTTCAATTGC      2100

ATCTGTACCA TTAGCATCAA AAAGCTGGAT ATTAACATTC TGTGCAGCAT CATTTCCTGA      2160

TTTTGTATTT TTTAATGTAT ATTCATTATT TTCATCTGCA TTTTTCCAAG AATAGAAATA      2220

AGCTCCAACT TTTGTTGCAA CAGGCTTATT ATTAGTAGTA GTAGTAGTAG AACAATTTTC      2280

TAAATTAATT GTAAATGGTG TTGGCATCGC TGTATCTTTT TTAGTTTTTA AATGATTTTT      2340

ACCCACATCA TTTAATACTA CGCTCATATT TTTACTATCC GTTTTCACTT TACAAGTATT      2400

CTCAACAACC TTACCAAAGA AAGTAACTTT ACCAGATGTT TCAGTACTTA CTTGAGGATC      2460

AGCAGCATTC GTTGCAAATG CCAATAAAAT TAAGCTACCA AGAAGTGTTT TTTTCATAAT      2520

AAATTGCTCC ATAAAGAGGT TTGTGCCTTA TAAATAAGGC AATAAAGATT AATATAAACC      2580

GTTATTAAA ATGCCAAAGG CTTAATAAAC AGCAAACTTT GTTTTCCCAA AAAAAGTAAA      2640

AAACTCTTCC ATTATATATA TATATATATA TAATTAAAGC CCTTTTTGAA AAATTTCATA      2700

TTTTTTTGAA TTAATTCGCT GTAGGTTGGG TTTTTGCCCA CATGGAGACA TATAAAAAAG      2760

ATTTGTAGGG TGGGCGTAAG CCCACGCGGA ACATCATCAA ACAACTGTAA TGTTGTATTA      2820

GGCACGGTGG GCTTATGCCT CGCCTACGGG GAA ATG AAT AAG GAT AAA TAT GGG      2874
                                     Met Asn Lys Asp Lys Tyr Gly
                                      1                   5

CTT AGC CCA GTT TAT GGA TTT AAT TAT GTT GAA ATG GGA AAA ACA ATG      2922
Leu Ser Pro Val Tyr Gly Phe Asn Tyr Val Glu Met Gly Lys Thr Met
        10                  15                  20

TTT AAA AAA ACA CTT TTA TTT TTT ACC GCA CTA TTT TTT GCC GCA CTT      2970
Phe Lys Lys Thr Leu Leu Phe Phe Thr Ala Leu Phe Phe Ala Ala Leu
    25                  30                  35

TGT GCA TTT TCA GCC AAT GCA GAT GTG ATT ATC ACT GGC ACC AGA GTG      3018
Cys Ala Phe Ser Ala Asn Ala Asp Val Ile Ile Thr Gly Thr Arg Val
40                  45                  50                      55

ATT TAT CCC GCT GGG CAA AAA AAT GTT ATC GTG AAG TTA GAA AAC AAT      3066
```

```
Ile Tyr Pro Ala Gly Gln Lys Asn Val Ile Val Lys Leu Glu Asn Asn
            60              65                      70

GAT GAT TCG GCA GCA TTG GTG CAA GCC TGG ATT GAT AAT GGC AAT CCA      3114
Asp Asp Ser Ala Ala Leu Val Gln Ala Trp Ile Asp Asn Gly Asn Pro
            75              80                      85

AAT GCC GAT CCA AAA TAC ACC AAA ACC CCT TTT GTG ATT ACC CCG CCT      3162
Asn Ala Asp Pro Lys Tyr Thr Lys Thr Pro Phe Val Ile Thr Pro Pro
            90              95                      100

GTT GCT CGA GTG GAA GCG AAA TCA GGG CAA AGT TTG CGG ATT ACG TTC      3210
Val Ala Arg Val Glu Ala Lys Ser Gly Gln Ser Leu Arg Ile Thr Phe
            105             110                     115

ACA GGC AGC GAG CCT TTA CCT GAT GAT CGC GAA AGC CTC TTT TAT TTT      3258
Thr Gly Ser Glu Pro Leu Pro Asp Asp Arg Glu Ser Leu Phe Tyr Phe
120             125                     130                     135

AAT TTG TTA GAT ATT CCG CCG AAA CCT GAT GCG GCA TTT CTG GCA AAA      3306
Asn Leu Leu Asp Ile Pro Pro Lys Pro Asp Ala Ala Phe Leu Ala Lys
                140                     145                     150

CAC GGC AGC TTT ATG CAA ATT GCC ATT CGC TCA CGT TTG AAG TTG TTT      3354
His Gly Ser Phe Met Gln Ile Ala Ile Arg Ser Arg Leu Lys Leu Phe
                155                     160                     165

TAT CGC CCT GCG AAA CTC TCG ATG GAT TCT CGT GAT GCA ATG AAA AAA      3402
Tyr Arg Pro Ala Lys Leu Ser Met Asp Ser Arg Asp Ala Met Lys Lys
                170                     175                     180

GTA GTG TTT AAA GCC ACA CCT GAA GGG GTG TTG GTG GAT AAT CAA ACC      3450
Val Val Phe Lys Ala Thr Pro Glu Gly Val Leu Val Asp Asn Gln Thr
        185                     190                     195

CCT TAT TAT ATG AAC TAC ATT GGT TTG TTA CAT CAA AAT AAA CCT GCG      3498
Pro Tyr Tyr Met Asn Tyr Ile Gly Leu Leu His Gln Asn Lys Pro Ala
200                     205                     210                     215

AAA AAT GTC AAA ATG GTT GCC CCT TTT TCT CAA GCG GTA TTT GAA GCC      3546
Lys Asn Val Lys Met Val Ala Pro Phe Ser Gln Ala Val Phe Glu Ala
                        220                     225                     230

AAA GGC GTG CGT TCT GGC GAT AAA TTG AAA TGG GTA TTG GTT AAT GAT      3594
Lys Gly Val Arg Ser Gly Asp Lys Leu Lys Trp Val Leu Val Asn Asp
                235                     240                     245

TAC GGT GCC GAC CAA GAA GGC GAA GCC ATC GCT CAA TAATAGCGAA           3640
Tyr Gly Ala Asp Gln Glu Gly Glu Ala Ile Ala Gln
                250                     255

CTAGTGTAGG GTGGGCTTTA GACCACCGAT TAACCATAAC AAAGGTGGGC TGAAGCCCAC    3700

CCTACAACCA CAAAGAACGA TTAATCTGTG AAAACAAAAA TTTTTCCCTT AAATAAAATT    3760

GCGTTTGCTT GTTCACTGCT ATTGGCAAAT CCTTTAGCGT GGGCGGGAGA TCAATTTGAT    3820

GCCTCTCTTT GGGGAGATGG TTCGGTGTTG GGCGTTGATT TTGCCCGATT TAATGTAAAA    3880

AATGCCGTGT TACCAGGGCG TTATGAAGCT CAAATCTATG TGAAATTTGA AGAAAAGGC     3940

GTAAGCGATA TTATTTTTGC TGATAATCCT GCCACAGGTC GGACAGAATT ATGCTTTACG    4000

CCTAAACTTC AAGAA ATG CTG GAT TTG ATG GAT GAA GCC ATT GTG AAA TCG    4051
                 Met Leu Asp Leu Met Asp Glu Ala Ile Val Lys Ser
                  1           5                       10

CCC AAT TCA GAA GAT GAC ACT TGT GTC TTT GCT TCT GAT GCT ATT CCT      4099
Pro Asn Ser Glu Asp Asp Thr Cys Val Phe Ala Ser Asp Ala Ile Pro
            15              20                      25

AAA GGC ACG TTT GAA TAT CAA AGC GGC GAA ATG AAA TTG AAA CTT GAG      4147
Lys Gly Thr Phe Glu Tyr Gln Ser Gly Glu Met Lys Leu Lys Leu Glu
        30                      35                      40

CTC CCT CAA GCT CTC ACT ATT CGC CGA CCA AGA GGC TAT ATT GCG CCA      4195
Leu Pro Gln Ala Leu Thr Ile Arg Arg Pro Arg Gly Tyr Ile Ala Pro
45                      50                      55                      60

TCT CGC TGG CAA ACT GGC ACC AAT GCC GCT TTT GCA AAT TAC GAT ATC      4243
```

| | | | | | | | | | | | | | | | | |
|---|---|---|---|---|---|---|---|---|---|---|---|---|---|---|---|---|
| Ser | Arg | Trp | Gln | Thr | Gly | Thr | Asn | Ala | Ala | Phe | Ala | Asn | Tyr | Asp | Ile | |
| | | | | 65 | | | | 70 | | | | | | 75 | | |

| AAC | TAT | TAT | CGT | TCT | GGT | AAT | CCC | GAA | GTA | AAA | TCC | GAA | AGT | TTG | TAT | 4291 |
|---|---|---|---|---|---|---|---|---|---|---|---|---|---|---|---|---|
| Asn | Tyr | Tyr | Arg | Ser | Gly | Asn | Pro | Glu | Val | Lys | Ser | Glu | Ser | Leu | Tyr | |
| | | | 80 | | | | 85 | | | | | 90 | | | | |

| GTG | GGC | TTG | CGT | AGT | GGC | GTA | AAT | TTT | GGC | AAC | TGG | GCA | TTG | CGT | CAT | 4339 |
|---|---|---|---|---|---|---|---|---|---|---|---|---|---|---|---|---|
| Val | Gly | Leu | Arg | Ser | Gly | Val | Asn | Phe | Gly | Asn | Trp | Ala | Leu | Arg | His | |
| | | 95 | | | | | 100 | | | | | 105 | | | | |

| AGC | GGC | AGT | TTT | AGC | CGT | TTT | GAA | AAC | CAA | AGT | AGC | TCG | GGT | TTT | ACT | 4387 |
|---|---|---|---|---|---|---|---|---|---|---|---|---|---|---|---|---|
| Ser | Gly | Ser | Phe | Ser | Arg | Phe | Glu | Asn | Gln | Ser | Ser | Ser | Gly | Phe | Thr | |
| | | 110 | | | | | 115 | | | | | 120 | | | | |

| GAT | AAG | GGC | AAA | AAT | CAT | TAC | GAA | CGT | GGC | GAT | ACC | TAT | TTA | CAA | CGA | 4435 |
|---|---|---|---|---|---|---|---|---|---|---|---|---|---|---|---|---|
| Asp | Lys | Gly | Lys | Asn | His | Tyr | Glu | Arg | Gly | Asp | Thr | Tyr | Leu | Gln | Arg | |
| 125 | | | | | 130 | | | | | 135 | | | | | 140 | |

| GAT | TTC | GCC | CTG | CTT | CGT | GGC | AAT | GTC | ACT | GTT | GGG | GAT | TTT | TTC | AGC | 4483 |
|---|---|---|---|---|---|---|---|---|---|---|---|---|---|---|---|---|
| Asp | Phe | Ala | Leu | Leu | Arg | Gly | Asn | Val | Thr | Val | Gly | Asp | Phe | Phe | Ser | |
| | | | | 145 | | | | | 150 | | | | | 155 | | |

| ACT | GCC | CGC | ATT | GGC | GAA | AAT | TTT | GGT | ATG | CGT | GGT | TTG | CGT | ATT | GCC | 4531 |
|---|---|---|---|---|---|---|---|---|---|---|---|---|---|---|---|---|
| Thr | Ala | Arg | Ile | Gly | Glu | Asn | Phe | Gly | Met | Arg | Gly | Leu | Arg | Ile | Ala | |
| | | | 160 | | | | | 165 | | | | | 170 | | | |

| TCT | GAT | GAT | AGA | ATG | CTT | GCC | CCA | TCA | CAA | CGT | GGT | TTT | GCC | CCA | GTG | 4579 |
|---|---|---|---|---|---|---|---|---|---|---|---|---|---|---|---|---|
| Ser | Asp | Asp | Arg | Met | Leu | Ala | Pro | Ser | Gln | Arg | Gly | Phe | Ala | Pro | Val | |
| | | 175 | | | | | 180 | | | | | 185 | | | | |

| GTG | CGT | GGC | GTG | GCA | AAC | ACA | AAC | GCC | AAA | GTC | AGC | ATC | AAA | CAA | AAT | 4627 |
|---|---|---|---|---|---|---|---|---|---|---|---|---|---|---|---|---|
| Val | Arg | Gly | Val | Ala | Asn | Thr | Asn | Ala | Lys | Val | Ser | Ile | Lys | Gln | Asn | |
| | 190 | | | | | 195 | | | | | 200 | | | | | |

| GGC | TAT | ACG | ATT | TAT | CAA | ATC | ACC | GTT | CCC | GCA | GGG | CCT | TTC | GTG | ATT | 4675 |
|---|---|---|---|---|---|---|---|---|---|---|---|---|---|---|---|---|
| Gly | Tyr | Thr | Ile | Tyr | Gln | Ile | Thr | Val | Pro | Ala | Gly | Pro | Phe | Val | Ile | |
| 205 | | | | | 210 | | | | | 215 | | | | | 220 | |

| AAC | GAT | TTG | TAT | GCC | AGC | GGT | TAT | AGC | GGC | GAT | TTA | ACG | GTG | GAA | ATC | 4723 |
|---|---|---|---|---|---|---|---|---|---|---|---|---|---|---|---|---|
| Asn | Asp | Leu | Tyr | Ala | Ser | Gly | Tyr | Ser | Gly | Asp | Leu | Thr | Val | Glu | Ile | |
| | | | | 225 | | | | | 230 | | | | | 235 | | |

| CAA | GAA | AGT | GAT | GGT | AAA | GTG | CGG | TCA | TTT | ATT | GTG | CCG | TTT | TCT | AAT | 4771 |
|---|---|---|---|---|---|---|---|---|---|---|---|---|---|---|---|---|
| Gln | Glu | Ser | Asp | Gly | Lys | Val | Arg | Ser | Phe | Ile | Val | Pro | Phe | Ser | Asn | |
| | | | 240 | | | | | 245 | | | | | 250 | | | |

| CTT | GCC | CCG | TTA | ATG | CGT | GTG | GGG | CAT | TTG | CGT | TAT | CAA | TTA | GCT | GGC | 4819 |
|---|---|---|---|---|---|---|---|---|---|---|---|---|---|---|---|---|
| Leu | Ala | Pro | Leu | Met | Arg | Val | Gly | His | Leu | Arg | Tyr | Gln | Leu | Ala | Gly | |
| | | 255 | | | | | 260 | | | | | 265 | | | | |

| GGA | CGT | TAT | CGA | ATT | GAC | AGC | CGC | ACC | TTT | GAT | GAA | CGT | GTG | TTA | CAA | 4867 |
|---|---|---|---|---|---|---|---|---|---|---|---|---|---|---|---|---|
| Gly | Arg | Tyr | Arg | Ile | Asp | Ser | Arg | Thr | Phe | Asp | Glu | Arg | Val | Leu | Gln | |
| | 270 | | | | | 275 | | | | | 280 | | | | | |

| GGC | GTG | TTG | CAA | TAT | GGT | TTA | ACT | AAT | CAT | CTC | ACG | CTG | AAT | TCA | AGC | 4915 |
|---|---|---|---|---|---|---|---|---|---|---|---|---|---|---|---|---|
| Gly | Val | Leu | Gln | Tyr | Gly | Leu | Thr | Asn | His | Leu | Thr | Leu | Asn | Ser | Ser | |
| 285 | | | | | 290 | | | | | 295 | | | | | 300 | |

| CTG | CTT | TAT | ACA | CGT | CAT | TAT | CGT | GCA | GGG | CTG | TTT | GGT | TTT | GGT | TTA | 4963 |
|---|---|---|---|---|---|---|---|---|---|---|---|---|---|---|---|---|
| Leu | Leu | Tyr | Thr | Arg | His | Tyr | Arg | Ala | Gly | Leu | Phe | Gly | Phe | Gly | Leu | |
| | | | | 305 | | | | | 310 | | | | | 315 | | |

| AAT | ACG | CCG | ATT | GGG | GCG | TTT | TCT | GCT | GAT | GCC | ACT | TGG | TCG | CAC | GCT | 5011 |
|---|---|---|---|---|---|---|---|---|---|---|---|---|---|---|---|---|
| Asn | Thr | Pro | Ile | Gly | Ala | Phe | Ser | Ala | Asp | Ala | Thr | Trp | Ser | His | Ala | |
| | | | 320 | | | | | 325 | | | | | 330 | | | |

| GAA | TTT | CCG | CTA | AAA | CAT | GTG | AGC | AAA | AAC | GGC | TAC | AGC | TTG | CAC | GGC | 5059 |
|---|---|---|---|---|---|---|---|---|---|---|---|---|---|---|---|---|
| Glu | Phe | Pro | Leu | Lys | His | Val | Ser | Lys | Asn | Gly | Tyr | Ser | Leu | His | Gly | |
| | | 335 | | | | | 340 | | | | | 345 | | | | |

| AGT | TAT | AGT | ATT | AAC | TTC | AAT | GAA | AGT | GGC | ACC | AAT | ATC | ACG | TTG | GCA | 5107 |
|---|---|---|---|---|---|---|---|---|---|---|---|---|---|---|---|---|
| Ser | Tyr | Ser | Ile | Asn | Phe | Asn | Glu | Ser | Gly | Thr | Asn | Ile | Thr | Leu | Ala | |
| | 350 | | | | | 355 | | | | | 360 | | | | | |

| GCC | TAT | CGC | TAT | TCT | TCA | CGG | GAT | TTT | TAC | ACC | TTA | AGC | GAC | ACC | ATT | 5155 |
|---|---|---|---|---|---|---|---|---|---|---|---|---|---|---|---|---|
| Ala | Tyr | Arg | Tyr | Ser | Ser | Arg | Asp | Phe | Tyr | Thr | Leu | Ser | Asp | Thr | Ile | |
| 365 | | | | | 370 | | | | | 375 | | | | | 380 | |

| GGT | CTT | AAC | CGC | ACT | TTC | AGA | CAA | TTT | AGC | GGT | GCG | TAT | TTG | CCT | GAA | 5203 |
|---|---|---|---|---|---|---|---|---|---|---|---|---|---|---|---|---|

```
Gly Leu Asn Arg Thr Phe Arg Gln Phe Ser Gly Ala Tyr Leu Pro Glu
            385                 390                 395

ATT TAC CGC CCA AAA AAT CAG TTT CAA GTG AGT TTA AGC CAA AGT CTG       5251
Ile Tyr Arg Pro Lys Asn Gln Phe Gln Val Ser Leu Ser Gln Ser Leu
            400                 405                 410

GGG AAT TGG GGA AAT CTC TAT CTT TCA GGA CAA ACC TAT AAT TAT TGG       5299
Gly Asn Trp Gly Asn Leu Tyr Leu Ser Gly Gln Thr Tyr Asn Tyr Trp
            415                 420                 425

GAA AAA CGT GGC ACG AAT ACG CAA TAT CAA GTT GCC TAT TCA AAC AGC       5347
Glu Lys Arg Gly Thr Asn Thr Gln Tyr Gln Val Ala Tyr Ser Asn Ser
            430                 435                 440

TTC CAC ATT CTT AAT TAC TCT GTA AAC CTC TCA CAG AGT ATT GAT AAA       5395
Phe His Ile Leu Asn Tyr Ser Val Asn Leu Ser Gln Ser Ile Asp Lys
445                 450                 455                 460

GAA ACG GGC AAA CGT GAC AAC AGC ATT TAT TTA AGT CTC AGC CTG CCA       5443
Glu Thr Gly Lys Arg Asp Asn Ser Ile Tyr Leu Ser Leu Ser Leu Pro
            465                 470                 475

TTA GGC GAT AAC CAT TCT GCA GAT AGT AGT TAT TCT CGC AGT GGT AAC       5491
Leu Gly Asp Asn His Ser Ala Asp Ser Ser Tyr Ser Arg Ser Gly Asn
            480                 485                 490

GAT ATT AAC CAA CGA CTT GGC GTA AAT GGC TCT TTT GGT GAA CGT CAT       5539
Asp Ile Asn Gln Arg Leu Gly Val Asn Gly Ser Phe Gly Glu Arg His
            495                 500                 505

CAA TGG AGT TAT GGT ATT AAC GCT TCA CGC AAT AAT CAA GGC TAT CGC       5587
Gln Trp Ser Tyr Gly Ile Asn Ala Ser Arg Asn Asn Gln Gly Tyr Arg
            510                 515                 520

AGT TAT GAC GGT AAT CTT TCG CAT AAC AAT AGC ATT GGT AGT TAC CGT       5635
Ser Tyr Asp Gly Asn Leu Ser His Asn Asn Ser Ile Gly Ser Tyr Arg
525                 530                 535                 540

GCT TCT TAT TCA CGT GAT AGC CTC AAA AAT CGC TCC ATC TCA CTG GGC       5683
Ala Ser Tyr Ser Arg Asp Ser Leu Lys Asn Arg Ser Ile Ser Leu Gly
            545                 550                 555

GCA AGC GGT GCT GTC GTG GCG CAC AAA CAC GGT ATT ACC TTA AGC CAA       5731
Ala Ser Gly Ala Val Val Ala His Lys His Gly Ile Thr Leu Ser Gln
            560                 565                 570

CCT GTT GGC GAA AGT TTT GCC ATT ATT CAC GCC AAA GAT GCC GCA GGA       5779
Pro Val Gly Glu Ser Phe Ala Ile Ile His Ala Lys Asp Ala Ala Gly
            575                 580                 585

GCA AAA GTG GAA TCA GGT GCC AAT GTG AGC CTT GAT TAT TTC GGC AAT       5827
Ala Lys Val Glu Ser Gly Ala Asn Val Ser Leu Asp Tyr Phe Gly Asn
            590                 595                 600

GCG GTT ATG CCT TAC ACC AGC CCG TAT GAA ATC AAT TAT ATC GGT ATC       5875
Ala Val Met Pro Tyr Thr Ser Pro Tyr Glu Ile Asn Tyr Ile Gly Ile
605                 610                 615                 620

AAT CCA TCT GAT GCG GAG GCG AAT GTG GAA TTT GAA GCC ACT GAA CGC       5923
Asn Pro Ser Asp Ala Glu Ala Asn Val Glu Phe Glu Ala Thr Glu Arg
            625                 630                 635

CAA ATC ATT CCT CGT GCA AAT TCA ATT AGC TTA GTA GAT TTC CGC ACG       5971
Gln Ile Ile Pro Arg Ala Asn Ser Ile Ser Leu Val Asp Phe Arg Thr
            640                 645                 650

GGC AAA AAT ACA ATG GTG TTA TTT AAC CTC ACT TTG CCA AAT GGC GAG       6019
Gly Lys Asn Thr Met Val Leu Phe Asn Leu Thr Leu Pro Asn Gly Glu
            655                 660                 665

CCA GTG CCA ATG GCA TCC ACC GCA CAA GAT AGC GAA GGG GCA TTT GTG       6067
Pro Val Pro Met Ala Ser Thr Ala Gln Asp Ser Glu Gly Ala Phe Val
            670                 675                 680

GGC GAT GTG GTG CAA GGT GGT GTG CTT TTC GCT AAT AAA CTT ACC CAG       6115
Gly Asp Val Val Gln Gly Gly Val Leu Phe Ala Asn Lys Leu Thr Gln
685                 690                 695                 700

CCA AAA GGC GAG TTA ATC GTC AAA TGG GGT GAG CGA AAA AGC GAA CAA       6163
```

```
                Pro  Lys  Gly  Glu  Leu  Ile  Val  Lys  Trp  Gly  Glu  Arg  Glu  Ser  Glu  Gln
                               705                          710                          715

TGC  CGT  TTC  CAA  TAT  CAA  GTT  GAT  TTG  GAT  AAC  GCA  CAA  ATA  CAA  AGT                    6211
Cys  Arg  Phe  Gln  Tyr  Gln  Val  Asp  Leu  Asp  Asn  Ala  Gln  Ile  Gln  Ser
               720                          725                          730

CAC  GAT  ATT  CAA  TGC  AAA  ACC  GCA  AAA  TAAATAATTG  AAGAGGATTT  ATG                           6261
His  Asp  Ile  Gln  Cys  Lys  Thr  Ala  Lys                                    Met
               735                          740                                 1

CAA  AAA  ACA  CCC  AAA  AAA  TTA  ACC  GCG  CTT  TTC  CAT  CAA  AAA  TCC  ACT                    6309
Gln  Lys  Thr  Pro  Lys  Lys  Leu  Thr  Ala  Leu  Phe  His  Gln  Lys  Ser  Thr
                 5                           10                          15

GCT  ACT  TGT  AGT  GGA  GCA  AAT  TAT  AGT  GGA  GCA  AAT  TAT  AGT  GGC  TCA                    6357
Ala  Thr  Cys  Ser  Gly  Ala  Asn  Tyr  Ser  Gly  Ala  Asn  Tyr  Ser  Gly  Ser
                20                           25                          30

AAA  TGC  TTT  AGG  TTT  CAT  CGT  CTG  GCT  CTG  CTT  GCT  TGC  GTG  GCT  CTG                    6405
Lys  Cys  Phe  Arg  Phe  His  Arg  Leu  Ala  Leu  Leu  Ala  Cys  Val  Ala  Leu
                35                           40                          45

CTT  GAT  TGC  ATT  GTG  GCA  CTG  CCT  GCT  TAT  GCT  TAC  GAT  GGC  AGA  GTG                    6453
Leu  Asp  Cys  Ile  Val  Ala  Leu  Pro  Ala  Tyr  Ala  Tyr  Asp  Gly  Arg  Val
 50                           55                           60                      65

ACC  TTT  CAA  GGG  GAG  ATT  TTA  AGT  GAT  GGC  ACT  TGT  AAA  ATT  GAA  ACA                    6501
Thr  Phe  Gln  Gly  Glu  Ile  Leu  Ser  Asp  Gly  Thr  Cys  Lys  Ile  Glu  Thr
                70                           75                          80

GAC  AGC  CAA  AAT  CGC  ACG  GTT  ACC  CTG  CCA  ACA  GTG  GGA  AAA  GCT  AAT                    6549
Asp  Ser  Gln  Asn  Arg  Thr  Val  Thr  Leu  Pro  Thr  Val  Gly  Lys  Ala  Asn
                85                           90                          95

TTA  AGC  CAC  GCA  GGG  CAA  ACC  GCC  GCC  CCT  GTG  CCT  TTT  TCC  ATC  ACG                    6597
Leu  Ser  His  Ala  Gly  Gln  Thr  Ala  Ala  Pro  Val  Pro  Phe  Ser  Ile  Thr
               100                          105                         110

TTA  AAA  GAA  TGC  AAT  GCA  GAT  GAT  GCT  ATG  AAA  GCT  AAT  CTG  CTA  TTT                    6645
Leu  Lys  Glu  Cys  Asn  Ala  Asp  Asp  Ala  Met  Lys  Ala  Asn  Leu  Leu  Phe
               115                          120                         125

AAA  GGG  GGA  GAC  AAC  ACA  ACA  GGG  CAA  TCT  TAT  CTT  TCC  AAT  AAG  GCA                    6693
Lys  Gly  Gly  Asp  Asn  Thr  Thr  Gly  Gln  Ser  Tyr  Leu  Ser  Asn  Lys  Ala
130                           135                          140                      145

GGC  AAC  GGC  AAA  GCC  ACC  AAC  GTG  GGC  ATT  CAA  ATT  GTC  AAA  GCC  GAT                    6741
Gly  Asn  Gly  Lys  Ala  Thr  Asn  Val  Gly  Ile  Gln  Ile  Val  Lys  Ala  Asp
               150                          155                         160

GGC  ATA  GGC  ACG  CCT  ATC  AAG  GTG  GAC  GGC  ACC  GAA  GCC  AAC  AGC  GAA                    6789
Gly  Ile  Gly  Thr  Pro  Ile  Lys  Val  Asp  Gly  Thr  Glu  Ala  Asn  Ser  Glu
               165                          170                         175

AAA  GCC  CCC  GAC  ACA  GGT  AAA  GCG  CAA  AAC  GGC  ACA  GTT  ATT  CAA  CCC                    6837
Lys  Ala  Pro  Asp  Thr  Gly  Lys  Ala  Gln  Asn  Gly  Thr  Val  Ile  Gln  Pro
               180                          185                         190

CGT  TTT  GGC  TAC  TTT  GGC  TCG  TTA  TTA  CGC  CAC  AGG  TGAAGCCACC                             6883
Arg  Phe  Gly  Tyr  Phe  Gly  Ser  Leu  Leu  Arg  His  Arg
               195                          200                         205

GCAGGCGACG  TTGAAGCCAC  TGCAACTTTT  GAAGTGCAGT  ATAACTAAAA  TATTTATTAT                             6943

CCAGTGAAAA  A ATG  AAT  AAG  AAA  TCG  TAT  ATA  AAT  CAT  TAC  TTA  ACT  TTA                     6993
              Met  Asn  Lys  Lys  Ser  Tyr  Ile  Asn  His  Tyr  Leu  Thr  Leu
                1                     5                          10

TTT  AAA  GTT  ACT  ACT  TTA  CTA  TTT  ACT  CTT  TCA  AGT  AAT  CCT  GTA  TGG                    7041
Phe  Lys  Val  Thr  Thr  Leu  Leu  Phe  Thr  Leu  Ser  Ser  Asn  Pro  Val  Trp
                15                           20                          25

GCA  AAT  ATA  AAA  ACA  GTT  CAG  GGA  ACA  ACT  AGT  GGT  TTT  CCA  CTT  CTA                    7089
Ala  Asn  Ile  Lys  Thr  Val  Gln  Gly  Thr  Thr  Ser  Gly  Phe  Pro  Leu  Leu
 30                           35                           40                      45

ACA  AGA  ACT  TTC  ACA  TTT  AAT  GGC  AAT  TTG  CAA  TGG  AAT  GTG  AGT  GCT                    7137
Thr  Arg  Thr  Phe  Thr  Phe  Asn  Gly  Asn  Leu  Gln  Trp  Asn  Val  Ser  Ala
                50                           55                          60
```

| | | | | | | | | | | | | | | | | |
|---|---|---|---|---|---|---|---|---|---|---|---|---|---|---|---|---|
| CTA | CAA | CCA | GCT | TAT | ATT | GTT | TCC | TCT | CAA | GCA | AGA | GAT | AAT | CTT | GAT | 7185 |
| Leu | Gln | Pro | Ala | Tyr | Ile | Val | Ser | Ser | Gln | Ala | Arg | Asp | Asn | Leu | Asp | |
| | | | 65 | | | | | 70 | | | | | 75 | | | |
| ACA | GTA | CAT | ATT | CAA | TCT | TCT | GAA | ATT | AAT | GCT | CCA | ACA | AAT | TCA | TTA | 7233 |
| Thr | Val | His | Ile | Gln | Ser | Ser | Glu | Ile | Asn | Ala | Pro | Thr | Asn | Ser | Leu | |
| | | | 80 | | | | | 85 | | | | | 90 | | | |
| GCT | CCA | TTT | AAT | AAT | TGG | ATT | AAT | ACG | AAA | TCA | GCA | GTA | GAG | CTA | GGT | 7281 |
| Ala | Pro | Phe | Asn | Asn | Trp | Ile | Asn | Thr | Lys | Ser | Ala | Val | Glu | Leu | Gly | |
| | | 95 | | | | | 100 | | | | | 105 | | | | |
| TAT | AGC | TTT | GCG | GGC | ATT | ACT | TGT | ACT | AGT | AAT | CCT | TGC | CCA | ACA | ATG | 7329 |
| Tyr | Ser | Phe | Ala | Gly | Ile | Thr | Cys | Thr | Ser | Asn | Pro | Cys | Pro | Thr | Met | |
| 110 | | | | | 115 | | | | 120 | | | | | 125 | | |
| AAA | TTA | CCA | TTA | TTA | TTT | CAT | CCT | GAT | CTT | ACT | AAT | TTA | ACT | CCA | CCT | 7377 |
| Lys | Leu | Pro | Leu | Leu | Phe | His | Pro | Asp | Leu | Thr | Asn | Leu | Thr | Pro | Pro | |
| | | | 130 | | | | | 135 | | | | | 140 | | | |
| GGA | AAG | AAA | AAT | TCT | GAT | GGA | GGG | GAG | ATT | TTT | AAA | TTA | CAT | AAT | GAA | 7425 |
| Gly | Lys | Lys | Asn | Ser | Asp | Gly | Gly | Glu | Ile | Phe | Lys | Leu | His | Asn | Glu | |
| | | | 145 | | | | | 150 | | | | | 155 | | | |
| TCT | AAT | TTA | GGC | GTC | TCT | TTT | CAA | ATT | GGA | GTA | AAA | ACG | AAT | ACT | TCT | 7473 |
| Ser | Asn | Leu | Gly | Val | Ser | Phe | Gln | Ile | Gly | Val | Lys | Thr | Asn | Thr | Ser | |
| | | | 160 | | | | | 165 | | | | | 170 | | | |
| CTA | GAT | TGG | GTT | AAT | GCT | AAG | AAT | AAT | TTT | AGC | TCT | CTA | AAA | GTT | TTA | 7521 |
| Leu | Asp | Trp | Val | Asn | Ala | Lys | Asn | Asn | Phe | Ser | Ser | Leu | Lys | Val | Leu | |
| | | 175 | | | | | 180 | | | | | 185 | | | | |
| ATG | GTG | CCT | TTT | AAT | TCT | AGC | GAT | AAA | ATA | TCT | TTG | CAT | TTA | CGT | GCT | 7569 |
| Met | Val | Pro | Phe | Asn | Ser | Ser | Asp | Lys | Ile | Ser | Leu | His | Leu | Arg | Ala | |
| 190 | | | | | 195 | | | | 200 | | | | | 205 | | |
| AAA | TTT | CAT | TTA | TTA | ACA | GAT | TTT | TCA | TCG | CTA | AAT | AAT | GAT | ATT | ACT | 7617 |
| Lys | Phe | His | Leu | Leu | Thr | Asp | Phe | Ser | Ser | Leu | Asn | Asn | Asp | Ile | Thr | |
| | | | 210 | | | | | 215 | | | | | 220 | | | |
| ATT | GAC | CCT | ATG | AAT | ACT | AGT | ATA | GGC | AAA | ATT | AAT | CTT | GAA | ACG | TGG | 7665 |
| Ile | Asp | Pro | Met | Asn | Thr | Ser | Ile | Gly | Lys | Ile | Asn | Leu | Glu | Thr | Trp | |
| | | | 225 | | | | | 230 | | | | | 235 | | | |
| CGT | GGC | TCA | ACA | GGC | AAT | TTT | TCT | GTT | AAA | TAT | GTA | GGT | GAG | GAT | AAG | 7713 |
| Arg | Gly | Ser | Thr | Gly | Asn | Phe | Ser | Val | Lys | Tyr | Val | Gly | Glu | Asp | Lys | |
| | | | 240 | | | | | 245 | | | | | 250 | | | |
| GGA | GAT | ATA | TCT | ATT | TTC | TTT | AAT | ACA | CCT | AAA | ATT | ATT | CTA | AAA | AAA | 7761 |
| Gly | Asp | Ile | Ser | Ile | Phe | Phe | Asn | Thr | Pro | Lys | Ile | Ile | Leu | Lys | Lys | |
| | | | 255 | | | | | 260 | | | | | 265 | | | |
| CAA | CAA | CGC | CGA | TGT | ACT | CTG | AAT | AAT | GCT | CCA | GTG | AGC | CCA | AAT | CCA | 7809 |
| Gln | Gln | Arg | Arg | Cys | Thr | Leu | Asn | Asn | Ala | Pro | Val | Ser | Pro | Asn | Pro | |
| 270 | | | | | 275 | | | | 280 | | | | | 285 | | |
| GTT | AAA | TTA | CGA | GCG | GTA | AAA | AAA | CGT | GAA | TTG | GAG | GCA | CAA | AGT | GAA | 7857 |
| Val | Lys | Leu | Arg | Ala | Val | Lys | Lys | Arg | Glu | Leu | Glu | Ala | Gln | Ser | Glu | |
| | | | 290 | | | | | 295 | | | | | 300 | | | |
| ATG | GAA | GGT | GGG | ACA | TTT | CAG | TTA | AGA | GTA | AAT | TGT | GAC | AAT | ACC | ACT | 7905 |
| Met | Glu | Gly | Gly | Thr | Phe | Gln | Leu | Arg | Val | Asn | Cys | Asp | Asn | Thr | Thr | |
| | | | 305 | | | | | 310 | | | | | 315 | | | |
| TAT | AAT | AAA | GCC | AAC | GGC | AAA | TGG | TTA | TTT | CCT | GTA | GTG | AAA | GTT | ACT | 7953 |
| Tyr | Asn | Lys | Ala | Asn | Gly | Lys | Trp | Leu | Phe | Pro | Val | Val | Lys | Val | Thr | |
| | | | 320 | | | | | 325 | | | | | 330 | | | |
| TTT | ACG | GAC | GAA | GAT | GGT | ACA | ACG | AAT | AAT | GGA | ACA | AAT | GAC | TTA | CTT | 8001 |
| Phe | Thr | Asp | Glu | Asp | Gly | Thr | Thr | Asn | Asn | Gly | Thr | Asn | Asp | Leu | Leu | |
| | | 335 | | | | | 340 | | | | | 345 | | | | |
| CGC | ACC | CAA | ACA | GGC | AGC | GGA | CAA | GCC | ACA | GGC | GTT | AGC | TTA | AGA | ATC | 8049 |
| Arg | Thr | Gln | Thr | Gly | Ser | Gly | Gln | Ala | Thr | Gly | Val | Ser | Leu | Arg | Ile | |
| 350 | | | | | 355 | | | | | 360 | | | | | 365 | |
| AAA | CGA | GAA | AAT | GGT | ACA | GAA | ACC | GTA | AAA | TAC | GGT | GCT | GAT | TCT | GCT | 8097 |
| Lys | Arg | Glu | Asn | Gly | Thr | Glu | Thr | Val | Lys | Tyr | Gly | Ala | Asp | Ser | Ala | |
| | | | 370 | | | | | 375 | | | | | 380 | | | |

```
CAA ATG GGG AAT GCT GGA CAA TTT GAA TTA CGA AAA CAA CCA TCC CCT           8145
Gln Met Gly Asn Ala Gly Gln Phe Glu Leu Arg Lys Gln Pro Ser Pro
        385                     390                     395

GCT GGT GGA GAT CAA TAT GCT GAA GAA ACT TTC AAA GTC TAT TAC GTA           8193
Ala Gly Gly Asp Gln Tyr Ala Glu Glu Thr Phe Lys Val Tyr Tyr Val
        400                     405                     410

AAA GAC TCA ACA AGA GGC ACC TTA ATC GAA GGA AAA GTC AAA GCC GCC           8241
Lys Asp Ser Thr Arg Gly Thr Leu Ile Glu Gly Lys Val Lys Ala Ala
        415                     420                     425

GCC ACT TTC ACA ATG TCA TAT CAA TAATAATGTC GGGTGGGAAT ATAAAGGCTG          8295
Ala Thr Phe Thr Met Ser Tyr Gln
430                 435

AAGGTTTAAA CTTCAGTCTT TTTTTATAGG AAAATACCAT TGCAACTTTA AGGATAAAAT        8355

TTTATCCTAA GCACAATTTT TATAAGAATA GGTCAAATT ATG TTA GCC AAA GCA            8409
                                             Met Leu Ala Lys Ala
                                             1                 5

AAA TAT AGA AAA GAT TAC AAA CAA CCA GAT TTT ACG GTC ACA GAC ATT           8457
Lys Tyr Arg Lys Asp Tyr Lys Gln Pro Asp Phe Thr Val Thr Asp Ile
        10                      15                      20

TAT TTA GAT TTT CAA CTT GAT CCT AAA AAT ACT GTG GTG ACT GCA ACC           8505
Tyr Leu Asp Phe Gln Leu Asp Pro Lys Asn Thr Val Val Thr Ala Thr
        25                      30                      35

ACA AAA TTC CAA CGC TTA AAT AAT GAA GCG ACG TCT TTA CGT TTA GAC           8553
Thr Lys Phe Gln Arg Leu Asn Asn Glu Ala Thr Ser Leu Arg Leu Asp
        40                      45                      50

GGG CAT AGC TTC CAG TTT TCT TCT ATT AAA TTT AAT GGC GAG CCA TTT           8601
Gly His Ser Phe Gln Phe Ser Ser Ile Lys Phe Asn Gly Glu Pro Phe
        55                      60                      65

TCT GAT TAT CAA CAA GAT GGC GAG AGT TTA ACG CTC GAT TTA AAA GAC           8649
Ser Asp Tyr Gln Gln Asp Gly Glu Ser Leu Thr Leu Asp Leu Lys Asp
70                      75                      80                  85

AAA AGT GCG GAT GAA TTT GAG CTT GAA ATT GTG ACG TTC CTT GTG CCA           8697
Lys Ser Ala Asp Glu Phe Glu Leu Glu Ile Val Thr Phe Leu Val Pro
                90                      95                      100

GCC GAA AAT ACG TCA TTA CAA GGG CTA TAT CAG TCT GGC GAA GGT ATT           8745
Ala Glu Asn Thr Ser Leu Gln Gly Leu Tyr Gln Ser Gly Glu Gly Ile
        105                     110                     115

TGT ACG CAA TGT GAG GCG GAA GGT TTC CGT CAA ATC ACT TAT ATG CTT           8793
Cys Thr Gln Cys Glu Ala Glu Gly Phe Arg Gln Ile Thr Tyr Met Leu
        120                     125                     130

GAT CGT CCT GAT GTG CTG GCG CGT TAT ATA ATC AAA ATT ACG GCA GAT           8841
Asp Arg Pro Asp Val Leu Ala Arg Tyr Ile Ile Lys Ile Thr Ala Asp
        135                     140                     145

AAA ACC AAA TAT CCA TTC TTA CTG TCG AAT GGT AAT CGC ATT GCA AGT           8889
Lys Thr Lys Tyr Pro Phe Leu Leu Ser Asn Gly Asn Arg Ile Ala Ser
150                     155                     160                 165

GGC GAA TTA GAA GAT GGT CGC CAT TGG GTG GAA TGG AAT GAT CCT TTC           8937
Gly Glu Leu Glu Asp Gly Arg His Trp Val Glu Trp Asn Asp Pro Phe
                170                     175                     180

CCA AAA CCA AGC TAT TTA TTT GCT TTA GTG GCG GGA GAT TNN GGT TTA           8985
Pro Lys Pro Ser Tyr Leu Phe Ala Leu Val Ala Gly Asp Xaa Gly Leu
                185                     190                     195

TTA CAA GAT AAN TTT ATT ACT AAA AGT GGT CGT GAA GTG GCT TTA GAG           9033
Leu Gln Asp Xaa Phe Ile Thr Lys Ser Gly Arg Glu Val Ala Leu Glu
        200                     205                     210

CTT TAT GTG GAT CGC GGT AAT CTT AAC CGT GCA ACT GGG GCA ATG GAA           9081
Leu Tyr Val Asp Arg Gly Asn Leu Asn Arg Ala Thr Gly Ala Met Glu
        215                     220                     225

AGT CTG AAA AAA GCG ATG AAA TGG GAT GAA GAT CGC TTT ATT TTA GAA           9129
```

| Ser | Leu | Lys | Lys | Ala | Met | Lys | Trp | Asp | Glu | Asp | Arg | Phe | Ile | Leu | Glu |
| 230 | | | | | 235 | | | | 240 | | | | | | 245 |

| TTT | TAC | CTA | GAT | ATT | TAT | ATG | ATC | GCG | GCC | GCC | GAT | TCC | TCC | AAT | ATG | 9177 |
| Phe | Tyr | Leu | Asp | Ile | Tyr | Met | Ile | Ala | Ala | Ala | Asp | Ser | Ser | Asn | Met | |
| | | | | 250 | | | | 255 | | | | | | 260 | | |

| GGC | GCA | ATG | GAA | AAT | AAA | GGA | TTA | AAT | ATC | TTT | AAC | TCT | AAA | TTG | GTG | 9225 |
| Gly | Ala | Met | Glu | Asn | Lys | Gly | Leu | Asn | Ile | Phe | Asn | Ser | Lys | Leu | Val | |
| | | | 265 | | | | 270 | | | | | | 275 | | | |

| TTG | GCA | AAT | CCA | CAA | ACG | GCA | ACA | GAT | GAA | GAT | TAT | CTT | GTC | ATT | GAA | 9273 |
| Leu | Ala | Asn | Pro | Gln | Thr | Ala | Thr | Asp | Glu | Asp | Tyr | Leu | Val | Ile | Glu | |
| | | 280 | | | | 285 | | | | | | 290 | | | | |

| AGT | GTG | ATT | GCA | CAC | GAA | TAT | TCC | CAT | AAC | TGG | ACG | GGA | AAC | CGT | GTA | 9321 |
| Ser | Val | Ile | Ala | His | Glu | Tyr | Ser | His | Asn | Trp | Thr | Gly | Asn | Arg | Val | |
| | 295 | | | | 300 | | | | | 305 | | | | | | |

| ACC | CGC | CGA | GAT | GGG | TTC | AAC | TAGGTTTGAA | GAAGGTTAAC | GGCTTCCGGG | | 9372 |
| Thr | Arg | Arg | Asp | Gly | Phe | Asn | | | | | |
| 310 | | | | | 315 | | | | | | |

AACAAGATTT CTCAGATCAG TTCTCCGGGC CGGAACCGAT TAATAAGGGA AAATTTTCCG 9432

( 2 ) INFORMATION FOR SEQ ID NO:5:

( i ) SEQUENCE CHARACTERISTICS:
( A ) LENGTH: 217 amino acids
( B ) TYPE: amino acid
( D ) TOPOLOGY: linear ( i i ) MOLECULE TYPE: protein ( x i ) SEQUENCE DESCRIPTION: SEQ ID NO:5:

| Met | Glu | Gln | Phe | Ile | Met | Lys | Lys | Thr | Leu | Leu | Gly | Ser | Leu | Ile | Leu |
| 1 | | | | 5 | | | | | 10 | | | | | 15 | |

| Leu | Ala | Phe | Ala | Thr | Asn | Ala | Ala | Asp | Pro | Gln | Val | Ser | Thr | Glu | Thr |
| | | | 20 | | | | | 25 | | | | | 30 | | |

| Ser | Gly | Lys | Val | Thr | Phe | Phe | Gly | Lys | Val | Val | Glu | Asn | Thr | Cys | Lys |
| | | 35 | | | | | 40 | | | | | 45 | | | |

| Val | Lys | Thr | Asp | Ser | Lys | Asn | Met | Ser | Val | Val | Leu | Asn | Asp | Val | Gly |
| | 50 | | | | | 55 | | | | | 60 | | | | |

| Lys | Asn | His | Leu | Lys | Thr | Lys | Lys | Asp | Thr | Ala | Met | Pro | Thr | Pro | Phe |
| 65 | | | | | 70 | | | | 75 | | | | | | 80 |

| Thr | Ile | Asn | Leu | Glu | Asn | Cys | Ser | Thr | Thr | Thr | Thr | Asn | Asn | Lys |
| | | | | 85 | | | | | 90 | | | | | 95 |

| Pro | Val | Ala | Thr | Lys | Val | Gly | Ala | Tyr | Phe | Tyr | Ser | Trp | Lys | Asn | Ala |
| | | | 100 | | | | | 105 | | | | | 110 | | |

| Asp | Glu | Asn | Asn | Glu | Tyr | Thr | Leu | Lys | Asn | Thr | Lys | Ser | Gly | Asn | Asp |
| | | | 115 | | | | | 120 | | | | | 125 | | |

| Ala | Ala | Gln | Asn | Val | Asn | Ile | Gln | Leu | Phe | Asp | Ala | Asn | Gly | Thr | Asp |
| | | 130 | | | | | 135 | | | | | 140 | | | |

| Ala | Ile | Glu | Val | Val | Gly | Asn | Gly | Thr | Thr | Asp | Phe | Thr | His | Ser | Asn |
| 145 | | | | | 150 | | | | | 155 | | | | | 160 |

| Thr | Asn | Asp | Val | Ala | Thr | Gln | Gln | Thr | Val | Asn | Lys | Asn | His | Ile | Ser |
| | | | | 165 | | | | | 170 | | | | | 175 | |

| Gly | Lys | Ala | Thr | Ile | Asn | Gly | Glu | Asn | Asn | Val | Lys | Leu | His | Tyr | Ile |
| | | | 180 | | | | | 185 | | | | | 190 | | |

| Ala | Arg | Tyr | Tyr | Ala | Thr | Ala | Gln | Ala | Glu | Ala | Gly | Lys | Val | Glu | Ser |
| | | 195 | | | | | 200 | | | | | 205 | | | |

| Ser | Val | Asp | Phe | Gln | Ile | Ala | Tyr | Glu |
| | 210 | | | | | 215 | | |

( 2 ) INFORMATION FOR SEQ ID NO:6:

( i ) SEQUENCE CHARACTERISTICS:
        ( A ) LENGTH: 259 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Asn Lys Asp Lys Tyr Gly Leu Ser Pro Val Tyr Gly Phe Asn Tyr
 1           5                  10                  15
Val Glu Met Gly Lys Thr Met Phe Lys Lys Thr Leu Leu Phe Phe Thr
            20                  25                  30
Ala Leu Phe Phe Ala Ala Leu Cys Ala Phe Ser Ala Asn Ala Asp Val
            35                  40                  45
Ile Ile Thr Gly Thr Arg Val Ile Tyr Pro Ala Gly Gln Lys Asn Val
        50                  55                  60
Ile Val Lys Leu Glu Asn Asn Asp Ser Ala Ala Leu Val Gln Ala
65                  70                  75                  80
Trp Ile Asp Asn Gly Asn Pro Asn Ala Asp Pro Lys Tyr Thr Lys Thr
                    85                  90                  95
Pro Phe Val Ile Thr Pro Val Ala Arg Val Glu Ala Lys Ser Gly
                100                 105                 110
Gln Ser Leu Arg Ile Thr Phe Thr Gly Ser Glu Pro Leu Pro Asp Asp
            115                 120                 125
Arg Glu Ser Leu Phe Tyr Phe Asn Leu Leu Asp Ile Pro Pro Lys Pro
        130                 135                 140
Asp Ala Ala Phe Leu Ala Lys His Gly Ser Phe Met Gln Ile Ala Ile
145                 150                 155                 160
Arg Ser Arg Leu Lys Leu Phe Tyr Arg Pro Ala Lys Leu Ser Met Asp
                    165                 170                 175
Ser Arg Asp Ala Met Lys Lys Val Val Phe Lys Ala Thr Pro Glu Gly
                180                 185                 190
Val Leu Val Asp Asn Gln Thr Pro Tyr Tyr Met Asn Tyr Ile Gly Leu
            195                 200                 205
Leu His Gln Asn Lys Pro Ala Lys Asn Val Lys Met Val Ala Pro Phe
        210                 215                 220
Ser Gln Ala Val Phe Glu Ala Lys Gly Val Arg Ser Gly Asp Lys Leu
225                 230                 235                 240
Lys Trp Val Leu Val Asn Asp Tyr Gly Ala Asp Gln Glu Gly Glu Ala
                    245                 250                 255
Ile Ala Gln
```

( 2 ) INFORMATION FOR SEQ ID NO:7:

( i ) SEQUENCE CHARACTERISTICS:
        ( A ) LENGTH: 741 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Leu Asp Leu Met Asp Glu Ala Ile Val Lys Ser Pro Asn Ser Glu
 1           5                  10                  15
Asp Asp Thr Cys Val Phe Ala Ser Asp Ala Ile Pro Lys Gly Thr Phe
            20                  25                  30
Glu Tyr Gln Ser Gly Glu Met Lys Leu Lys Leu Glu Leu Pro Gln Ala
```

|    | 35  |     |     |     |     | 40  |     |     |     |     | 45  |     |     |     |     |
|----|-----|-----|-----|-----|-----|-----|-----|-----|-----|-----|-----|-----|-----|-----|-----|
| Leu | Thr 50 | Ile | Arg | Arg | Pro | Arg 55 | Gly | Tyr | Ile | Ala | Pro 60 | Ser | Arg | Trp | Gln |
| Thr 65 | Gly | Thr | Asn | Ala 70 | Ala | Phe | Ala | Asn | Tyr 75 | Asp | Ile | Asn | Tyr | Tyr | Arg 80 |
| Ser | Gly | Asn | Pro | Glu 85 | Val | Lys | Ser | Glu | Ser 90 | Leu | Tyr | Val | Gly | Leu 95 | Arg |
| Ser | Gly | Val | Asn 100 | Phe | Gly | Asn | Trp | Ala 105 | Leu | Arg | His | Ser | Gly 110 | Ser | Phe |
| Ser | Arg | Phe 115 | Glu | Asn | Gln | Ser | Ser 120 | Gly | Phe | Thr | Asp | Lys 125 | Gly | Lys |
| Asn | His 130 | Tyr | Glu | Arg | Gly | Asp 135 | Thr | Tyr | Leu | Gln | Arg 140 | Asp | Phe | Ala | Leu |
| Leu 145 | Arg | Gly | Asn | Val | Thr 150 | Val | Gly | Asp | Phe | Phe 155 | Ser | Thr | Ala | Arg | Ile 160 |
| Gly | Glu | Asn | Phe | Gly 165 | Met | Arg | Gly | Leu | Arg 170 | Ile | Ala | Ser | Asp | Asp 175 | Arg |
| Met | Leu | Ala | Pro 180 | Ser | Gln | Arg | Gly | Phe 185 | Ala | Pro | Val | Val | Arg 190 | Gly | Val |
| Ala | Asn | Thr 195 | Asn | Ala | Lys | Val | Ser 200 | Ile | Lys | Gln | Asn | Gly 205 | Tyr | Thr | Ile |
| Tyr | Gln 210 | Ile | Thr | Val | Pro | Ala 215 | Gly | Pro | Phe | Val | Ile 220 | Asn | Asp | Leu | Tyr |
| Ala 225 | Ser | Gly | Tyr | Ser | Gly 230 | Asp | Leu | Thr | Val | Glu 235 | Ile | Gln | Glu | Ser | Asp 240 |
| Gly | Lys | Val | Arg | Ser 245 | Phe | Ile | Val | Pro | Phe 250 | Ser | Asn | Leu | Ala | Pro 255 | Leu |
| Met | Arg | Val | Gly 260 | His | Leu | Arg | Tyr | Gln 265 | Leu | Ala | Gly | Gly | Arg 270 | Tyr | Arg |
| Ile | Asp | Ser 275 | Arg | Thr | Phe | Asp | Glu 280 | Arg | Val | Leu | Gln | Gly 285 | Val | Leu | Gln |
| Tyr | Gly 290 | Leu | Thr | Asn | His | Leu 295 | Thr | Leu | Asn | Ser | Ser 300 | Leu | Leu | Tyr | Thr |
| Arg 305 | His | Tyr | Arg | Ala | Gly 310 | Leu | Phe | Gly | Phe | Gly 315 | Leu | Asn | Thr | Pro | Ile 320 |
| Gly | Ala | Phe | Ser | Ala 325 | Asp | Ala | Thr | Trp | Ser 330 | His | Ala | Glu | Phe | Pro 335 | Leu |
| Lys | His | Val | Ser 340 | Lys | Asn | Gly | Tyr | Ser 345 | Leu | His | Gly | Ser | Tyr 350 | Ser | Ile |
| Asn | Phe | Asn 355 | Glu | Ser | Gly | Thr | Asn 360 | Ile | Thr | Leu | Ala | Ala 365 | Tyr | Arg | Tyr |
| Ser | Ser 370 | Arg | Asp | Phe | Tyr | Thr 375 | Leu | Ser | Asp | Thr | Ile 380 | Gly | Leu | Asn | Arg |
| Thr 385 | Phe | Arg | Gln | Phe | Ser 390 | Gly | Ala | Tyr | Leu | Pro 395 | Glu | Ile | Tyr | Arg | Pro 400 |
| Lys | Asn | Gln | Phe | Gln 405 | Val | Ser | Leu | Ser | Gln 410 | Ser | Leu | Gly | Asn | Trp 415 | Gly |
| Asn | Leu | Tyr | Leu 420 | Ser | Gly | Gln | Thr | Tyr 425 | Asn | Tyr | Trp | Glu | Lys 430 | Arg | Gly |
| Thr | Asn | Thr 435 | Gln | Tyr | Gln | Val | Ala 440 | Tyr | Ser | Asn | Ser | Phe 445 | His | Ile | Leu |
| Asn | Tyr 450 | Ser | Val | Asn | Leu | Ser 455 | Gln | Ser | Ile | Asp | Lys 460 | Glu | Thr | Gly | Lys |

-continued

| | | | | | | | | | | | | | | |
|---|---|---|---|---|---|---|---|---|---|---|---|---|---|---|
| Arg | Asp | Asn | Ser | Ile | Tyr | Leu | Ser | Leu | Ser | Leu | Pro | Leu | Gly | Asp | Asn |
| 465 | | | | 470 | | | | 475 | | | | | | | 480 |
| His | Ser | Ala | Asp | Ser | Ser | Tyr | Ser | Arg | Ser | Gly | Asn | Asp | Ile | Asn | Gln |
| | | | | 485 | | | | 490 | | | | | 495 | | |
| Arg | Leu | Gly | Val | Asn | Gly | Ser | Phe | Gly | Glu | Arg | His | Gln | Trp | Ser | Tyr |
| | | | 500 | | | | | 505 | | | | | 510 | | |
| Gly | Ile | Asn | Ala | Ser | Arg | Asn | Asn | Gln | Gly | Tyr | Arg | Ser | Tyr | Asp | Gly |
| | | | 515 | | | | 520 | | | | | 525 | | | |
| Asn | Leu | Ser | His | Asn | Asn | Ser | Ile | Gly | Ser | Tyr | Arg | Ala | Ser | Tyr | Ser |
| | | 530 | | | | 535 | | | | | 540 | | | | |
| Arg | Asp | Ser | Leu | Lys | Asn | Arg | Ser | Ile | Ser | Leu | Gly | Ala | Ser | Gly | Ala |
| 545 | | | | | 550 | | | | 555 | | | | | | 560 |
| Val | Val | Ala | His | Lys | His | Gly | Ile | Thr | Leu | Ser | Gln | Pro | Val | Gly | Glu |
| | | | | 565 | | | | | 570 | | | | | 575 | |
| Ser | Phe | Ala | Ile | Ile | His | Ala | Lys | Asp | Ala | Ala | Gly | Ala | Lys | Val | Glu |
| | | | 580 | | | | 585 | | | | | 590 | | | |
| Ser | Gly | Ala | Asn | Val | Ser | Leu | Asp | Tyr | Phe | Gly | Asn | Ala | Val | Met | Pro |
| | | 595 | | | | | 600 | | | | | 605 | | | |
| Tyr | Thr | Ser | Pro | Tyr | Glu | Ile | Asn | Tyr | Ile | Gly | Ile | Asn | Pro | Ser | Asp |
| | 610 | | | | | 615 | | | | | 620 | | | | |
| Ala | Glu | Ala | Asn | Val | Glu | Phe | Glu | Ala | Thr | Glu | Arg | Gln | Ile | Ile | Pro |
| 625 | | | | | 630 | | | | | 635 | | | | | 640 |
| Arg | Ala | Asn | Ser | Ile | Ser | Leu | Val | Asp | Phe | Arg | Thr | Gly | Lys | Asn | Thr |
| | | | | 645 | | | | 650 | | | | | | 655 | |
| Met | Val | Leu | Phe | Asn | Leu | Thr | Leu | Pro | Asn | Gly | Glu | Pro | Val | Pro | Met |
| | | | 660 | | | | | 665 | | | | | 670 | | |
| Ala | Ser | Thr | Ala | Gln | Asp | Ser | Glu | Gly | Ala | Phe | Val | Gly | Asp | Val | Val |
| | | 675 | | | | | 680 | | | | | 685 | | | |
| Gln | Gly | Gly | Val | Leu | Phe | Ala | Asn | Lys | Leu | Thr | Gln | Pro | Lys | Gly | Glu |
| | 690 | | | | | 695 | | | | | 700 | | | | |
| Leu | Ile | Val | Lys | Trp | Gly | Glu | Arg | Glu | Ser | Glu | Gln | Cys | Arg | Phe | Gln |
| 705 | | | | | 710 | | | | 715 | | | | | | 720 |
| Tyr | Gln | Val | Asp | Leu | Asp | Asn | Ala | Gln | Ile | Gln | Ser | His | Asp | Ile | Gln |
| | | | | 725 | | | | | 730 | | | | | 735 | |
| Cys | Lys | Thr | Ala | Lys | | | | | | | | | | | |
| | | | | 740 | | | | | | | | | | | |

( 2 ) INFORMATION FOR SEQ ID NO:8:

( i ) SEQUENCE CHARACTERISTICS:
        ( A ) LENGTH: 205 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | | |
|---|---|---|---|---|---|---|---|---|---|---|---|---|---|---|---|
| Met | Gln | Lys | Thr | Pro | Lys | Lys | Leu | Thr | Ala | Leu | Phe | His | Gln | Lys | Ser |
| 1 | | | | 5 | | | | | 10 | | | | | 15 | |
| Thr | Ala | Thr | Cys | Ser | Gly | Ala | Asn | Tyr | Ser | Gly | Ala | Asn | Tyr | Ser | Gly |
| | | | 20 | | | | | 25 | | | | | 30 | | |
| Ser | Lys | Cys | Phe | Arg | Phe | His | Arg | Leu | Ala | Leu | Leu | Ala | Cys | Val | Ala |
| | | | 35 | | | | | 40 | | | | | 45 | | |
| Leu | Leu | Asp | Cys | Ile | Val | Ala | Leu | Pro | Ala | Tyr | Ala | Tyr | Asp | Gly | Arg |
| | | | 50 | | | | 55 | | | | | 60 | | | |
| Val | Thr | Phe | Gln | Gly | Glu | Ile | Leu | Ser | Asp | Gly | Thr | Cys | Lys | Ile | Glu |
| 65 | | | | | 70 | | | | | 75 | | | | | 80 |

| | | | | | | | | | | | | | | |
|---|---|---|---|---|---|---|---|---|---|---|---|---|---|---|
| Thr | Asp | Ser | Gln | Asn<br>85 | Arg | Thr | Val | Thr | Leu<br>90 | Pro | Thr | Val | Gly | Lys<br>95 | Ala |
| Asn | Leu | Ser | His | Ala<br>100 | Gly | Gln | Thr | Ala<br>105 | Ala | Pro | Val | Pro | Phe<br>110 | Ser | Ile |
| Thr | Leu | Lys<br>115 | Glu | Cys | Asn | Ala | Asp<br>120 | Asp | Ala | Met | Lys | Ala<br>125 | Asn | Leu | Leu |
| Phe | Lys<br>130 | Gly | Gly | Asp | Asn | Thr<br>135 | Thr | Gly | Gln | Ser | Tyr<br>140 | Leu | Ser | Asn | Lys |
| Ala<br>145 | Gly | Asn | Gly | Lys | Ala<br>150 | Thr | Asn | Val | Gly | Ile<br>155 | Gln | Ile | Val | Lys | Ala<br>160 |
| Asp | Gly | Ile | Gly | Thr<br>165 | Pro | Ile | Lys | Val | Asp<br>170 | Gly | Thr | Glu | Ala | Asn<br>175 | Ser |
| Glu | Lys | Ala | Pro<br>180 | Asp | Thr | Gly | Lys | Ala<br>185 | Gln | Asn | Gly | Thr | Val<br>190 | Ile | Gln |
| Pro | Arg | Phe<br>195 | Gly | Tyr | Phe | Gly | Ser<br>200 | Leu | Leu | Arg | His | Arg<br>205 | | | |

(2) INFORMATION FOR SEQ ID NO:9:

(i) SEQUENCE CHARACTERISTICS:
        (A) LENGTH: 437 amino acids
        (B) TYPE: amino acid
        (D) TOPOLOGY: linear (ii) MOLECULE TYPE: protein (xi) SEQUENCE DESCRIPTION: SEQ ID NO:9:

| | | | | | | | | | | | | | | |
|---|---|---|---|---|---|---|---|---|---|---|---|---|---|---|
| Met<br>1 | Asn | Lys | Lys | Ser<br>5 | Tyr | Ile | Asn | His | Tyr<br>10 | Leu | Thr | Leu | Phe | Lys<br>15 | Val |
| Thr | Thr | Leu | Leu<br>20 | Phe | Thr | Leu | Ser | Ser<br>25 | Asn | Pro | Val | Trp | Ala<br>30 | Asn | Ile |
| Lys | Thr | Val<br>35 | Gln | Gly | Thr | Thr | Ser<br>40 | Gly | Phe | Pro | Leu | Leu<br>45 | Thr | Arg | Thr |
| Phe | Thr<br>50 | Phe | Asn | Gly | Asn | Leu<br>55 | Gln | Trp | Asn | Val | Ser<br>60 | Ala | Leu | Gln | Pro |
| Ala<br>65 | Tyr | Ile | Val | Ser | Ser<br>70 | Gln | Ala | Arg | Asp | Asn<br>75 | Leu | Asp | Thr | Val | His<br>80 |
| Ile | Gln | Ser | Ser | Glu<br>85 | Ile | Asn | Ala | Pro | Thr<br>90 | Asn | Ser | Leu | Ala | Pro<br>95 | Phe |
| Asn | Asn | Trp | Ile<br>100 | Asn | Thr | Lys | Ser | Ala<br>105 | Val | Glu | Leu | Gly | Tyr<br>110 | Ser | Phe |
| Ala | Gly | Ile<br>115 | Thr | Cys | Thr | Ser | Asn<br>120 | Pro | Cys | Pro | Thr | Met<br>125 | Lys | Leu | Pro |
| Leu | Leu<br>130 | Phe | His | Pro | Asp | Leu<br>135 | Thr | Asn | Leu | Thr | Pro<br>140 | Pro | Gly | Lys | Lys |
| Asn<br>145 | Ser | Asp | Gly | Gly | Glu<br>150 | Ile | Phe | Lys | Leu | His<br>155 | Asn | Glu | Ser | Asn | Leu<br>160 |
| Gly | Val | Ser | Phe | Gln<br>165 | Ile | Gly | Val | Lys | Thr<br>170 | Asn | Thr | Ser | Leu | Asp<br>175 | Trp |
| Val | Asn | Ala | Lys<br>180 | Asn | Asn | Phe | Ser | Ser<br>185 | Leu | Lys | Val | Leu | Met<br>190 | Val | Pro |
| Phe | Asn | Ser<br>195 | Ser | Asp | Lys | Ile | Ser<br>200 | Leu | His | Leu | Arg | Ala<br>205 | Lys | Phe | His |
| Leu | Leu<br>210 | Thr | Asp | Phe | Ser | Ser<br>215 | Leu | Asn | Asn | Asp | Ile<br>220 | Thr | Ile | Asp | Pro |
| Met | Asn | Thr | Ser | Ile | Gly | Lys | Ile | Asn | Leu | Glu | Thr | Trp | Arg | Gly | Ser |

```
225                      230                      235                      240

Thr   Gly   Asn   Phe   Ser   Val   Lys   Tyr   Val   Glu   Asp   Lys   Gly   Asp   Ile
                        245                     250                     255

Ser   Ile   Phe   Phe   Asn   Thr   Pro   Lys   Ile   Ile   Leu   Lys   Lys   Gln   Gln   Arg
                  260                     265                     270

Arg   Cys   Thr   Leu   Asn   Asn   Ala   Pro   Val   Ser   Pro   Asn   Pro   Val   Lys   Leu
            275                     280                     285

Arg   Ala   Val   Lys   Lys   Arg   Glu   Leu   Glu   Ala   Gln   Ser   Glu   Met   Glu   Gly
      290                     295                     300

Gly   Thr   Phe   Gln   Leu   Arg   Val   Asn   Cys   Asp   Asn   Thr   Thr   Tyr   Asn   Lys
305                     310                     315                     320

Ala   Asn   Gly   Lys   Trp   Leu   Phe   Pro   Val   Val   Lys   Val   Thr   Phe   Thr   Asp
                        325                     330                     335

Glu   Asp   Gly   Thr   Thr   Asn   Asn   Gly   Thr   Asn   Asp   Leu   Leu   Arg   Thr   Gln
                  340                     345                     350

Thr   Gly   Ser   Gly   Gln   Ala   Thr   Gly   Val   Ser   Leu   Arg   Ile   Lys   Arg   Glu
            355                     360                     365

Asn   Gly   Thr   Glu   Thr   Val   Lys   Tyr   Gly   Ala   Asp   Ser   Ala   Gln   Met   Gly
      370                     375                     380

Asn   Ala   Gly   Gln   Phe   Glu   Leu   Arg   Lys   Gln   Pro   Ser   Pro   Ala   Gly   Gly
385                     390                     395                     400

Asp   Gln   Tyr   Ala   Glu   Glu   Thr   Phe   Lys   Val   Tyr   Tyr   Val   Lys   Asp   Ser
                        405                     410                     415

Thr   Arg   Gly   Thr   Leu   Ile   Glu   Gly   Lys   Val   Lys   Ala   Ala   Ala   Thr   Phe
                  420                     425                     430

Thr   Met   Ser   Tyr   Gln
                  435
```

(2) INFORMATION FOR SEQ ID NO:10:

(i) SEQUENCE CHARACTERISTICS:
        (A) LENGTH: 316 amino acids
        (B) TYPE: amino acid
        (D) TOPOLOGY: linear (ii) MOLECULE TYPE: protein (xi) SEQUENCE DESCRIPTION: SEQ ID NO:10:

```
Met   Leu   Ala   Lys   Ala   Lys   Tyr   Arg   Lys   Asp   Tyr   Lys   Gln   Pro   Asp   Phe
 1                      5                      10                     15

Thr   Val   Thr   Asp   Ile   Tyr   Leu   Asp   Phe   Gln   Leu   Asp   Pro   Lys   Asn   Thr
                  20                     25                     30

Val   Val   Thr   Ala   Thr   Thr   Lys   Phe   Gln   Arg   Leu   Asn   Asn   Glu   Ala   Thr
            35                     40                     45

Ser   Leu   Arg   Leu   Asp   Gly   His   Ser   Phe   Gln   Phe   Ser   Ser   Ile   Lys   Phe
      50                     55                     60

Asn   Gly   Glu   Pro   Phe   Ser   Asp   Tyr   Gln   Gln   Asp   Gly   Glu   Ser   Leu   Thr
65                     70                     75                     80

Leu   Asp   Leu   Lys   Asp   Lys   Ser   Ala   Asp   Glu   Phe   Glu   Leu   Glu   Ile   Val
                        85                     90                     95

Thr   Phe   Leu   Val   Pro   Ala   Glu   Asn   Thr   Ser   Leu   Gln   Gly   Leu   Tyr   Gln
                  100                    105                    110

Ser   Gly   Glu   Gly   Ile   Cys   Thr   Gln   Cys   Glu   Ala   Glu   Gly   Phe   Arg   Gln
            115                    120                    125

Ile   Thr   Tyr   Met   Leu   Asp   Arg   Pro   Asp   Val   Leu   Ala   Arg   Tyr   Ile   Ile
      130                    135                    140
```

| | | | | | | | | | | | | | | |
|---|---|---|---|---|---|---|---|---|---|---|---|---|---|---|
| Lys | Ile | Thr | Ala | Asp | Lys | Thr | Lys | Tyr | Pro | Phe | Leu | Leu | Ser | Asn | Gly |
| 145 | | | | 150 | | | | | 155 | | | | | | 160 |
| Asn | Arg | Ile | Ala | Ser | Gly | Glu | Leu | Glu | Asp | Gly | Arg | His | Trp | Val | Glu |
| | | | | 165 | | | | 170 | | | | | 175 | | |
| Trp | Asn | Asp | Pro | Phe | Pro | Lys | Pro | Ser | Tyr | Leu | Phe | Ala | Leu | Val | Ala |
| | | | 180 | | | | | 185 | | | | | 190 | | |
| Gly | Asp | Xaa | Gly | Leu | Leu | Gln | Asp | Xaa | Phe | Ile | Thr | Lys | Ser | Gly | Arg |
| | | | 195 | | | | 200 | | | | | 205 | | | |
| Glu | Val | Ala | Leu | Glu | Leu | Tyr | Val | Asp | Arg | Gly | Asn | Leu | Asn | Arg | Ala |
| | 210 | | | | | 215 | | | | 220 | | | | | |
| Thr | Gly | Ala | Met | Glu | Ser | Leu | Lys | Lys | Ala | Met | Lys | Trp | Asp | Glu | Asp |
| 225 | | | | | 230 | | | | | 235 | | | | | 240 |
| Arg | Phe | Ile | Leu | Glu | Phe | Tyr | Leu | Asp | Ile | Tyr | Met | Ile | Ala | Ala | Ala |
| | | | | 245 | | | | | 250 | | | | | 255 | |
| Asp | Ser | Ser | Asn | Met | Gly | Ala | Met | Glu | Asn | Lys | Gly | Leu | Asn | Ile | Phe |
| | | | | 260 | | | | 265 | | | | | 270 | | |
| Asn | Ser | Lys | Leu | Val | Leu | Ala | Asn | Pro | Gln | Thr | Ala | Thr | Asp | Glu | Asp |
| | | 275 | | | | | 280 | | | | | 285 | | | |
| Tyr | Leu | Val | Ile | Glu | Ser | Val | Ile | Ala | His | Glu | Tyr | Ser | His | Asn | Trp |
| | 290 | | | | | 295 | | | | | 300 | | | | |
| Thr | Gly | Asn | Arg | Val | Thr | Arg | Arg | Asp | Gly | Phe | Asn | | | | |
| 305 | | | | | 310 | | | | | 315 | | | | | |

( 2 ) INFORMATION FOR SEQ ID NO:11:

( i ) SEQUENCE CHARACTERISTICS:
        ( A ) LENGTH: 670 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

| | | | | | | | | | | | | | | |
|---|---|---|---|---|---|---|---|---|---|---|---|---|---|---|
| Lys | Ile | Glu | Glu | Gly | Lys | Leu | Val | Ile | Trp | Ile | Asn | Gly | Asp | Lys | Gly |
| 1 | | | | 5 | | | | | 10 | | | | | 15 | |
| Tyr | Asn | Gly | Leu | Ala | Glu | Val | Gly | Lys | Lys | Phe | Glu | Lys | Asp | Thr | Gly |
| | | | 20 | | | | | 25 | | | | | 30 | | |
| Ile | Lys | Val | Thr | Val | Glu | His | Pro | Asp | Lys | Leu | Glu | Glu | Lys | Phe | Pro |
| | | | 35 | | | | | 40 | | | | | 45 | | |
| Gln | Val | Ala | Ala | Thr | Gly | Asp | Gly | Pro | Asp | Ile | Ile | Phe | Trp | Ala | His |
| | 50 | | | | | 55 | | | | | 60 | | | | |
| Asp | Arg | Phe | Gly | Gly | Tyr | Ala | Gln | Ser | Gly | Leu | Leu | Ala | Glu | Ile | Thr |
| 65 | | | | | 70 | | | | | 75 | | | | | 80 |
| Pro | Asp | Lys | Ala | Phe | Gln | Asp | Lys | Leu | Tyr | Pro | Phe | Thr | Trp | Asp | Ala |
| | | | | 85 | | | | | 90 | | | | | 95 | |
| Val | Arg | Tyr | Asn | Gly | Lys | Leu | Ile | Ala | Tyr | Pro | Ile | Ala | Val | Glu | Ala |
| | | | | 100 | | | | | 105 | | | | | 110 | |
| Leu | Ser | Leu | Ile | Tyr | Asn | Lys | Asp | Leu | Leu | Pro | Asn | Pro | Pro | Lys | Thr |
| | | | | 115 | | | | | 120 | | | | | 125 | |
| Trp | Glu | Glu | Ile | Pro | Ala | Leu | Asp | Lys | Glu | Leu | Lys | Ala | Lys | Gly | Lys |
| | | | 130 | | | | | 135 | | | | | 140 | | |
| Ser | Ala | Leu | Met | Phe | Asn | Leu | Gln | Glu | Pro | Tyr | Phe | Thr | Trp | Pro | Leu |
| 145 | | | | | 150 | | | | | 155 | | | | | 160 |
| Ile | Ala | Ala | Asp | Gly | Gly | Tyr | Ala | Phe | Lys | Tyr | Glu | Asn | Gly | Lys | Tyr |
| | | | | 165 | | | | | 170 | | | | | 175 | |
| Asp | Lys | Ile | Lys | Asp | Val | Gly | Val | Asp | Asn | Ala | Gly | Ala | Lys | Ala | Gly |

|     |     |     |     |     | 180 |     |     |     |     | 185 |     |     |     |     | 190 |     |     |
|---|---|---|---|---|---|---|---|---|---|---|---|---|---|---|---|---|---|

Leu Thr Phe Leu Val Asp Leu Ile Lys Asn Lys His Met Asn Ala Asp
        195                     200                 205

Thr Asp Tyr Ser Ile Ala Glu Ala Phe Asn Lys Gly Glu Thr Ala
210                 215                 220

Met Thr Ile Asn Gly Pro Trp Ala Trp Ser Asn Ile Asp Thr Ser Lys
225             230                 235                 240

Val Asn Tyr Gly Val Thr Val Leu Pro Thr Phe Lys Gly Gln Pro Ser
            245             250                 255

Lys Pro Phe Val Gly Val Leu Ser Ala Gly Ile Asn Ala Ala Ser Pro
            260                 265             270

Asn Lys Glu Leu Ala Lys Glu Phe Leu Glu Asn Tyr Leu Leu Thr Asp
        275             280             285

Glu Gly Leu Glu Ala Val Asn Lys Asp Lys Pro Leu Gly Ala Val Ala
    290             295             300

Leu Lys Ser Tyr Glu Glu Leu Ala Lys Asp Pro Arg Ile Ala Ala
305             310             315             320

Thr Met Glu Asn Ala Gln Lys Gly Glu Ile Met Pro Asn Ile Pro Gln
                325             330             335

Met Ser Ala Phe Trp Tyr Ala Val Arg Thr Ala Val Ile Asn Ala Ala
            340             345             350

Ser Gly Arg Gln Thr Val Asp Glu Ala Leu Lys Asp Ala Gln Thr Arg
        355             360             365

Ile Thr Lys Ile Glu Gly Arg Thr Leu Ser Ser Asn Pro Val Trp Ala
    370             375             380

Asn Ile Lys Thr Val Gly Thr Thr Ser Gly Phe Pro Leu Leu Thr Arg
385             390             395                 400

Thr Phe Thr Glu Asn Gly Asn Leu Trp Asn Val Ser Ala Leu Pro Ala
            405             410             415

Tyr Ile Val Ser Ser Ala Arg Asp Asn Leu Asp Thr Val His Ile Gln
        420             425             430

Ser Ser Glu Ile Asn Ala Pro Thr Asn Ser Leu Ala Pro Glu Asn Asn
        435             440             445

Trp Ile Asn Thr Lys Ser Ala Val Glu Leu Gly Tyr Ser Phe Ala Gly
    450             455             460

Ile Thr Cys Thr Ser Asn Pro Cys Pro Thr Met Lys Leu Pro Leu Leu
465             470             475                 480

Phe His Pro Leu Thr Asn Leu Thr Pro Pro Gly Lys Lys Asn Ser Asp
            485             490                 495

Gly Gly Glu Ile Phe Lys Leu His Asn Glu Ser Asn Leu Gly Val Ser
            500             505             510

Phe Gln Ile Gly Val Lys Thr Asn Thr Ser Leu Asp Trp Val Asn Ala
        515             520             525

Lys Asn Asn Phe Ser Ser Leu Lys Val Leu Met Val Pro Phe Asn Ser
530             535             540

Ser Lys Ser Ile Ser Leu His Leu Arg Ala Lys Phe His Leu Leu Thr
545             550             555             560

Asp Phe Ser Ser Leu Asn Asn Asp Ile Thr Ile Asp Pro Met Asn Thr
            565             570             575

Ser Ile Gly Lys Ile Asn Leu Glu Thr Trp Arg Gly Ser Thr Gly Asn
        580             585             590

Phe Ser Val Lys Tyr Val Gly Glu Asp Lys Gly Asp Ile Ser Ile Phe
        595             600             605

```
        Phe  Asn  Thr  Pro  Lys  Ile  Ile  Leu  Lys  Lys  Gln  Gln  Arg  Arg  Cys  Thr
                       610                 615                 620

Leu  Asn  Asn  Ala  Pro  Val  Ser  Pro  Asn  Pro  Val  Lys  Leu  Arg  Ala  Val
        625                      630                 635                           640

Lys  Lys  Arg  Glu  Leu  Glu  Ala  Gln  Ser  Glu  Met  Glu  Gly  Gly  Thr  Phe
                            645                      650                      655

Leu  Arg  Val  Asn  Cys  Asp  Asn  Thr  Thr  Tyr  Asn  Lys  Ala  Asn
                       660                      665                 670
```

( 2 ) INFORMATION FOR SEQ ID NO:12:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

```
GTGCTGGATC  CGTTTCTCTT  GCATTACATT  AGG                                         33
```

( 2 ) INFORMATION FOR SEQ ID NO:13:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

```
TTAGGAATTC  GGAAGCGTTT  TTTACTTTTT  TTGG                                        34
```

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

```
AACGAATTCT  GCTGTTTATT  AAGGCTTTAG                                              30
```

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
AGCTGGATCC  TTGTAGGGTG  GGCGTAAGCC                                              30
```

( 2 ) INFORMATION FOR SEQ ID NO:16:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
AGCTGGATCC  TTGTAGGGTG  GGCGTAAGCC                                              30
```

( 2 ) INFORMATION FOR SEQ ID NO:17:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:17:

AACGGATTCG TTTGCTGTTT ATTAAGCCTT                    30

( 2 ) INFORMATION FOR SEQ ID NO:18:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( x i ) SEQUENCE DESCRIPTION: SEQ ID NO:18:

AACGGATTCG TTTGCTGTTT ATTAAGCCTT                    30

( 2 ) INFORMATION FOR SEQ ID NO:19:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:19:

GGCAAATACG CACCGCTAAA T                             21

( 2 ) INFORMATION FOR SEQ ID NO:20:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:20:

CGGACGAAGA TGGTACAACG A                             21

( 2 ) INFORMATION FOR SEQ ID NO:21:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( x i ) SEQUENCE DESCRIPTION: SEQ ID NO:21:

CCAAGCTTGG CCCGACATTA TTATTGATAT GACA               34

SEQUENCE AND ANALYSIS OF LKP PILIN STRUCTURAL GENES AND THE LKP PILI OPERON OF NONTYPABLE *HAEMOPHILUS INFLUENZAE*

RELATED APPLICATION

This application is a Continuation-In-Part of Ser. No. 08/277,231 filed Jul. 19, 1994, the contents of which is incorporated herein by reference.

BACKGROUND OF THE INVENTION

Nontypable *Haemophilus influenzae* (NTHi) are primarily noninvasive human respiratory tract pathogens. NTHi can reside in the respiratory tract as a commensal or give rise to local infections, including otitis media, bronchitis, sinusitis, and rarely, pneumonia (Bluestone, C. D., and J. O. Klein, *In Pediatric Otolaryngology.*, 356 (1983); Bluestone and Stool ed. W. B. Saunders Co. Philadelphia.; Musher, D. M. et al., *Ann. Intern. Med.* 99:344–350 (1983)). Several potential adherence factors have been described for *Haemophilus influenzae* (both typable and nontypable) adherence to human cells, including four classes of fimbriae/pili and two high molecular weight proteins with similarity to the filamentous hemagglutinin of *Bordetella pertussis* (St. Geme, J. W., et al., *Proc. Natl. Acad. Sci. USA* 90:2875–2879 (1993)). Pili are bacterial surface antigens. They are protein appendages consisting of a helically symmetrical assembly of major protein (pilin) subunits. Some pili can also carry from two to three minor proteins assembled on their tips. One of these proteins, adhesin, carries the active site for pilus adhesion to specific membrane receptors on human and animal cells.

One class of pili/fimbriae has been widely studied, the long thick pili (LKP) family. LKP pili are expressed by both typable and nontypable *H. influenzae* (Hib). The pili in this family have a characteristic morphology, partially shared adhesion specificity and their structural proteins share amino acid sequences. These pili are hemagglutination positive and mediate attachment to human mucosal cells (Brinton, C. C. et al., *Pediatr. Infect. Dis. J.* 8 Suppl.:54–61 (1989)). Hemagglutination of human erythrocytes is accomplished via binding to the AnWj blood group antigen while binding to epithelial cells involves a sialic acid containing lactosylceramide receptor (van Alphen, L. et al., *Infect. Immun.* 69:4473–4477 (1991)).

The LKP family has been divided into different strain specific serotypes based on reactivity to polyclonal antisera raised against the purified pili. Little cross reactivity among pili serotypes has been observed (Brinton, C. C., et al., *Pediatr. Infect. Dis. J.* 8 Suppl.:54–61 (1989)).

Inhibiting, or blocking, LKP pilus-mediated adhesion by *H. influenzae* to cells can prevent *H. influenzae* diseases. Purified, intact LKP pili have been shown to be vaccine candidates for NTHi otitis media in the chinchilla model, conferring protection against challenge with NTHi strains bearing homologous pili serotype (Karasic, R. et al., *Pediatr. Infect. Dis. J.* 8 (Suppl.): S62–65 (1988)). However, because protection is pilus-specific, for broad protection, a vaccine would be required to be multivalent, including the most frequently occurring serotypes of pili in the natural population of pathogens. LKP pilin structural genes have been cloned and sequenced by several groups (Coleman, T. et al., *Infect. Immun.* 59:1716–1722 (1991); Forney, L. J. et al., *Infect. Immun.* 59:1991–1996 (1991); Kar, S., et al., *Infect. Immun.* 58:903–908 (1990); van Ham, S. M., et al., *EMBO Jour.* 8:3535–3540 (1989)), but only the genes responsible for pili serotypes 1 and 4 have been identified.

SUMMARY OF THE INVENTION

The invention relates to the isolation, cloning and sequencing of the pilin gene for the *Haemophilus influenzae* pili serotype 5 (FIG. 1), to the sequencing of the entire LKP1 operon, which is set forth in FIGS. 2A–G, and to the cloning of the LKP10, LKP11, and LKP12 pili. The present invention also relates to DNA molecules (also referred to herein as DNA sequences or nucleic acid sequences) which encode proteins which comprise the *H. influenzae* LKP, particularly a tip adhesin protein. The present invention also relates to DNA molecules capable of hybridizing to the DNA sequences of the *Haemophilus influenzae* genome related to the pili. The DNA molecules of the present invention can be used in a method for assaying a sample, such as a blood sample, for the presence of *Haemophilus influenzae*. Accordingly, the present invention relates to the use of the DNA molecules as a diagnostic.

The present invention further relates to recombinant *Haemophilus influenzae* pili proteins, and peptides, specifically a tip adhesin protein. The proteins, or peptides, of the present invention can be used to produce antibodies, both polyclonal and monoclonal, which are reactive with (i.e., bind to) the *H. influenzae* pili proteins, and can be used in diagnostic assays to detect the presence of *Haemophilus influenzae* antibodies, in for example, a blood sample. Such antibodies to *Haemophilus influenzae* also be used as vaccines in methods of passive immunization.

The proteins and peptides of the present invention can also be employed in methods for immunizing a mammal, such as a human, against *Haemophilus influenzae* infection and, thus, as a vaccine for the prevention of *Haemophilus influenzae* related diseases, for example, otitis media. In particular, based on the DNA and amino acid sequences presented herein, an adhesin protein, or peptide, vaccine can be constructed which can induce protecting antibodies to *H. influenzae* in mammals.

BRIEF DESCRIPTION OF THE DRAWINGS

FIG. 1 is a graphic illustration of the conserved regions of the pilin genes of *H. influenzae* serotypes 1, 4 and 5 (SEQ ID NOs:1–3, respectively).

FIGS. 2A–2G show the DNA sequence (SEQ ID NO:4) of the LKP1 operon and the deduced amino acid sequences for the six open reading frames (SEQ ID NOs:5–10).

FIG. 9 shows the amino acid sequence of LKP1 fusion protein. The underline indicates the partial amino acid sequence of the LKP tip adhesin protein that was fused to maltose-binding protein (SEQ ID NO:11).

DETAILED DESCRIPTION OF THE INVENTION

Figure 3:
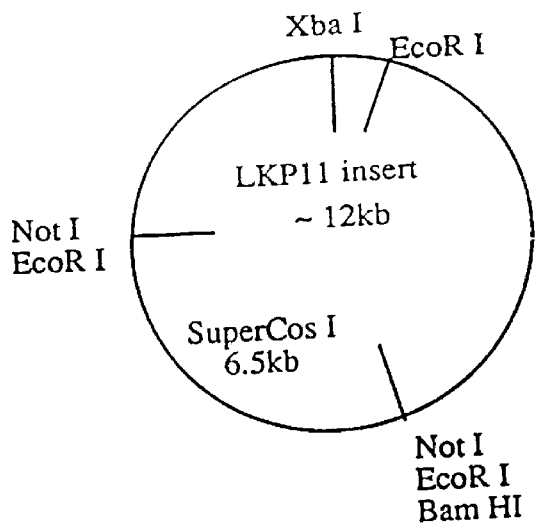
FIGS. 3, 4, and 5 are schematics of the physical maps obtained by restriction enzyme digestion of vectors containing LKP inserts.

Described herein, for the first time, is the cloning of the *Haemophilus influenzae* serotype 5 pilin gene and the sequence of the entire LKP1 operon. The LKP1 operon, as shown in FIGS. 2A–G, is composed of five separate genes, designated hipP (the pilin gene), hipC (the periplasmic chaperone gene), hipR (the membrane anchor gene), hipM (the minor tip associated protein gene) and hipA (the tip adhesin gene). These five genes are also referred to herein as hifA (for hipP), hifB (for hipC), hifC (for hipR), hifD (for hipM) and hifE (for hipA). Also present on the LKP1 operon are an integrase gene, and a peptidase gene. The proteins encoded by these genes of the LKP1 operon and the LKP5 pilin protein are collectively referred to herein as the *H. influenzae* pili proteins.

The present invention encompasses the isolated and/or recombinant nucleic acid sequences encoding the *H. influenzae* pili proteins, or biologically active fragments thereof, described herein. As used herein nucleic acids are also referred to as DNA and RNA, or DNA sequences and RNA sequences, or DNA molecules or RNA molecules. Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods known to those of skill in the art to obtain isolated nucleic acids and methods described herein. These isolated nucleic acids include essentially pure nucleic acids, nucleic acids produced by chemical synthesis, by combinations of biological and chemical methods, and recombinant nucleic acids which are isolated.

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Also encompassed by the present invention are nucleic acid sequences (DNA or RNA sequences) which are substantially complementary to the *H. influenzae* DNA sequences described herein, and nucleic acid sequences which hybridize with these DNA sequences under conditions of stringency known to those of skill in the art sufficient to identify DNA sequences with substantial nucleic acid sequence identity. It is reasonable to predict that DNA sequences identified under such stringent conditions will likely encode a protein (also referenced to herein as a polypeptide, or peptide fragment) with the biological activity of *H. influenzae* pili proteins. A general description of stringent hybridization conditions are discussed in Ausubel, F. M., et al., *Current Protocols in Molecular Biology*, Greene Publishing Assoc. and Wiley-Interscience 1989, the teachings of which are incorporated herein by reference. Factors such as probe length, base composition, percent mismatch between the hybridizing sequences, temperature and ionic strength influence the stability of nucleic acid hybrids. Thus, stringency conditions sufficient to identify additional *H. influenzae* pili proteins, (e.g., high or moderate stringency conditions) can be determined empirically, depending in part upon the characteristics of the known DNA to which other unknown nucleic acids are being compared for sequence similarity.

As defined herein, substantially complementary means that the sequence need not reflect the exact sequence of e.g., SEQ ID NO:4, but must be sufficiently similar in identity of sequence to hybridize with SEQ ID NO:4 under stringent conditions. For example, non-complementary bases, or longer or shorter sequences can be interspersed in sequences provided the sequence has sufficient complementary bases with, e.g., SEQ ID NO:4 to hybridize therewith.

The DNA molecules of the present invention can, preferably, encode a functional or biologically active pili protein, such as the pilin gene, hipP; the periplasmic chaperon, hipC; the membrane anchor protein, hipR; the tip associated protein, hipM and most preferably, the tip adhesin protein, hipA. A "functional or biologically active protein" is defined herein as a protein which shares significant identity (e.g., at least about 65%, preferably at least about 80% and most preferably at least about 95%) with the corresponding sequences of the endogenous protein and possesses one or more of the functions thereof. Biological functions of the *H. influenzae* pili proteins include antigenic structural, and adhesion properties. For example, as described in Karasic, R. et al. (Karasic, R. et al., *Pediatr. Infect. Dis. J.* 8 (*Suppl.*): S62–65 (1988)), the teachings of which are herein incorporated by reference, pili proteins can be shown to adhere to mucosal cells and erythrocytes. Thus, such adhesion properties can be a measure of biological activity. Also described herein, biological activity can include the antigenicity of the protein, or peptide, resulting in the production of antibodies which bind to the pili proteins.

The *H. influenzae* pili proteins of the present invention are understood to specifically include the proteins of the LKP1 operon and the serotype 5 hipP pilin protein, and proteins having amino acid sequences analogous to these sequences. Such proteins are defined herein as *H. influenzae* pili protein analogs, or derivatives. Analogous amino acid sequences are defined herein to mean amino acid sequences with sufficient identity of amino acid sequence with, e.g., LKP1 tip adhesin protein, to possess the biological activity of tip adhesin. The biological activity of tip adhesin can include, for example, the capability of tip adhesin to bind to specific membrane receptors on human and animal cells. For example, an analog polypeptide can be produced with "silent" changes in the amino acid sequence wherein one, or more amino acid residue differs from the amino acid residues of the LKP1 adhesin, yet still possess adhesion activity. Examples of such differences include additions, deletions or substitutions of residues to e.g., SEQ ID NO:9. Also encompassed by the present invention are analogous proteins that exhibit lesser or greater biological activity of the pili proteins of the present invention.

The present invention also encompasses biologically active protein, or biologically active fragments of the *H. influenzae* pili proteins described herein. Such fragments can include only a part of the full-length amino acid sequence of a pili protein yet possess biological activity. Such fragments can be produced by amino- and carboxyl-terminal deletions, as well as internal deletions. Such peptide fragments can be tested for biological activity as described herein. Thus, a functional, or biologically active, protein includes mutants or derivatives of the endogenous protein wherein one or more amino acids have been substituted, deleted or added. Also included are active fragments of the protein. The *H. influenzae* pili proteins, as set forth above, include functional or biologically active pili proteins, such as the pilin structural protein, hipP; the periplasmic chaperon, hipC; the membrane anchor protein, hipR; the tip associated protein, hipM; and most preferably, the tip adhesin protein, hipA.

The present invention further relates to fusion proteins comprising the pili proteins described herein (referred to herein as a first moiety) linked to a second moiety not occurring in the pili protein as found in nature. Thus, the second moiety can be a single amino acid, peptide or polypeptide. The first moiety can be in an N-terminal location, a C-terminal location or internal to the fusion protein. In one embodiment, the fusion protein comprises a pili protein and either a maltose binding protein (MBP) (SEQ ID NO:11) or glutathione-S-transferase (GST).

The DNA sequences of the present invention can also be used in a recombinant construct for the infection, transfection or transformation of a cell in vitro or in vivo under control of an appropriate promoter for the expression of functional *H. influenzae* pili proteins, as defined herein, in an appropriate host cell. Such recombinant constructs are also referred to herein as expression vectors. For example, a DNA sequence can be functionally ligated to a suitable promoter (e.g., a constitutive or inducible promoter or the endogenous promoter) introduced into a suitable expression vector, such as pUC19, which is then introduced into a suitable host cell. The construct can also include DNA encoding one or more selectable markers (such as neo, gpt, dhfr, ada, pac, hyg and hisd) or DNA encoding one or more different antigens or therapeutic proteins.

The construct can be introduced by any suitable means, as set forth above, such as by calcium phosphate precipitation, microinjection, electroporation or infection (such as with an infectious retroviral, herpes vaccinia or adenovirus vector). The host cell can be a eucaryotic or procaryotic cell. Suitable cells include bacterial (e.g. *E. coli*) or mammalian cells. Mammalian cells include primary somatic cells, such as, epithelial cells, fibroblasts, keratinocytes, macrophages or T cells, or immortalized cell lines, such as HeLa or HT1080. The recombinant host cell can then be cultured and, optionally, selected, in vitro under appropriate conditions resulting in the expression of the protein. Alternatively, the cell can be transplanted or injected into an animal, such as a human, for in vivo expression.

In one embodiment, the present invention relates to LKP type pili-producing *E. coli* recombinants. Such recombinants have been constructed from *Haemophilus infuenzae*, as described herein. These single serotype recombinants produced pili in large, easily purifiable quantities. They did not phase vary or become recalcitrant upon subculture and could be grown as *E. coli* in liquid medium with good pilus yields. The single serotype pilus preparations grown and purified from them contained pili identical to those on the parent *H. influenzae* (Hflu) strains and contained no other Hflu antigens. These preparations are easily standardized for purity, identity, concentration and potency for subsequent mixing into a multivalent vaccine and provides an efficient means of producing pilus for vaccine manufacture. As described herein, single-type-producing *E. coli* recombinant vaccine strains have been constructed for LKP10, LKP11 and LKP12 serotypes.

Multiple serotype recombinants containing two operons on separate plasmids have also been constructed. Single colonies of these strains simultaneously expressed, in good quantities, two serotypes of pili. However, these strains were unstable in that, during in vitro subculture, they tended to rapidly lose pilus expression, perhaps because the plasmids used were incompatible. When the two operons are placed on two compatible plasmids these strains are expected to be more stable. The use of stable, high-producing double-expressing recombinant strains could simply production of proteins suitable for vaccine use by reducing by half the number of vaccine strains required.

Good production, concentration and purification methods for Hflu LKP pili of different serotypes have been developed and are described herein. Pili can be purified from *E. coli* recombinant cultures producing Hflu pili as described for the purification of pili from Hflu culture. Both solid phase and liquid phase fermentation methods have been used. The preferred procedure involves mechanical removal of pili from the harvested bacteria and their separation from the bacterial cells by centrugation. Pili are concentrated and further purified by alternate cycles of longitudinal aggregation (crystallization) of intact pilus rods with soluble impurities removed by centrugation of the crystals followed by solubilization of the pilus crystals into free pilus rods with particulate impurities removed by centrugation. Each stage of the production/purification process was optimized for each pilus serotype. To date, nineteen different LKP serotypes have been purified.

Alternative pilus purification methods with analytical and industrial utility have also been developed Using appropriate solvent and column conditions, intact pili can be purified away from contaminating proteins by HPLC or FPLC on molecular sizing, hydrophobic or ion exchange columns. These methods are also capable of scale-up for industrial production.

Purification methods for individual pilus proteins have also been developed starting with intact LKP pili. Hflu LKP pilus structural proteins, as deduced from the multiple sequence alignment of pilus gene sequences with other pilus genes, include pilin, small tip minor and large tip minor proteins. The large tip minor protein is referred to as the "adhesin" because it carries the known LKP pilus adhesion specificity for human red blood cells. However, by analogy with other pilus families, the other two LKP pilus structural proteins may also be adhesins with specificities for as yet unknown human receptors. Both pilins and adhesins of LKP pili have been puried in biologically active form.

The pilins are purified in assembled rod form by removal of the minor tip proteins and separation of rods from minors on molecular sizing columns. In their assembled form, the pilin units retain the antigenic specificity of intact pili which is conferred by the exposed surface determinants of the pilin subunits on the lateral surface of the pilus rod. Pilin rods are expected to be equally as effective multivalent vaccine components as intact pili may have advantage of higher purity and possibly reduced side effects.

The adhesin of LKP11 has been isolated and purified in active and soluble form. Its removal from LKP11 pili eliminates the ability of these pili to bind to human red blood cells. In pure form it can bind to human red blood cell membranes. The adhesin band on SDS gels is labeled by antibodies reactive with fusion protein comprised of a fragment of adhesin and maltose binding protein. Purified LKP pilus adhesins may have utility as vaccine components capable of inducing adhesion-blocking or clearing antibodies. The LKP11 adhesin did not cross-react antigenically with the LKP1 adhesin on Western blots. Thus, the SDS/PAGE gel similarity of apparent molecular weights found for 3 different LKP adhesins was not predictive of antigenic similarity in this limited two-serotype test. Free adhesins can be tested for efficacy as otitis media vaccines and for their ability to induce adhesion-blocking antibodies. Antiserum to the fusion protein, which labeled the adhesin band on Western blots, did not block adhesion to red cells.

The isolated recombinant proteins of the present invention can be administered to a mammal to protect, or to treat the mammal against *H. influenzae* infection. Isolated recombinant pili protein can be formulated into a vaccine composition, for example, as described in U.S. Pat. No. 5,336,490, the teachings of which are incorporated herein by reference. The protein can also be administered via an infectious construct, preferably a replication incompetent or attenuated viral construct. Alternatively, the protein can be administered via a recombinant host cell (such as, a mammalian cell) which will express the protein in vivo or in a pharmaceutically acceptable carrier. In particular, the recombinant LKP1 tip adhesin protein, a biologically active fragment thereof, or a fusion protein, can be used in a vaccine composition to induce the production of antibodies in a mammal. It is reasonable to predict that such antibodies can protect the mammal from *H. influenzae* diseases.

The vaccine composition may be administered in a single dose or in more than one dose over a period of time to achieve a level of antibody in the blood which is sufficient to confer protection from *H. influenzae* infection.

Suitable pharmaceutical carriers include, but are not limited to water, salt solutions, alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized and desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active agents, e.g., enzyme inhibitors, to reduce metabolic degradation.

For parenteral application, particularly suitable are injectable, sterile solutions, preferably oily or aqueous solutions, as well as suspensions, emulsions, or implants, including suppositories. Ampoules are convenient unit dosages.

Modes of administration are those known in the art, such as parenteral, oral or intranasal administration or by cellular implantation.

It will be appreciated that the actual effective amounts of the protein in a specific case will vary according to the specific compound being utilized, the particular composition formulated, the mode of administration and the age, weight and condition of the patient, for example. As used herein, an effective amount of protein is an amount of protein which is capable of raising the level of antibody in a mammal to a level sufficient to provide protection from *H. influenzae* infection. Dosages for a particular patient can be determined by one of ordinary skill in the art using conventional considerations, (e.g. by means of an appropriate, conventional pharmacological protocol).

The DNA molecules and proteins of the present invention can be used in in vitro diagnostic assays to detect the presence of *H. influenzae* in biological samples. In one embodiment, the DNA molecules, or fragments thereof, can be used as probes in an assay for detecting *Haemophilus influenzae* in a sample, such as a blood sample from a mammal, e.g. a human. Such probes can be designed such that they specifically bind to the target sequence (e.g., an *H. influenzae* pili protein).

In one embodiment the DNA probe can comprise the nucleotides of a serotype conserved region of the *H. influenzae* genome, such as the nucleotides encoding a tip adhesin protein. To specifically bind to the target sequence, the probe must be of sufficient length to provide the desired specificity, i.e., to avoid being hybridized to random sequences in the sample. The DNA molecule capable of hybridization preferably contains at least about 400 nucleotides, more preferably at least about 1000 nucleotides, and most preferably at least about 1200 nucleotides. For example, the DNA molecule can comprise at least about 400 nucleotides between about nucleotide 7000 to 7400 of SEQ ID NO:4. The DNA hybridization probe preferably shares at least about around 70% homology or the corresponding sequences of the *Haemophilus influenzae* genome, more preferably at least about 80% and most preferably at least about 90%.

In particular, the DNA molecules of the present invention are capable of hybridizing to serotype conserved regions of the *H. influenzae* genome. A particularly preferred embodiment are DNA molecules that hybridize with the *H. influenzae* region encoding the tip adhesin protein. For example, a DNA molecule can be capable of hybridizing to the gene encoding the tip adhesin protein of serotype 1, preferably the sequence set forth between about nucleotide 6955 to 8265 of SEQ ID NO:4. In one embodiment, the DNA molecule is capable of hybridizing to the genome under stringent conditions, as described herein. The hybridization assay can be performed employing known hybridization procedures, such as those described herein. The probe can be, for example, detectably labeled employing known labels in the art, including enzymes, dyes, antibodies and radioactive labels. The probe is preferably immobilized on a solid support (e.g., a membrane).

Alternatively, the DNA molecule can be selected such that it hybridizes to a non-conserved region of the *Haemophilus influenzae* genome. For example, a DNA molecule that hybridizes to the gene encoding the pilin protein can be employed. Such an assay can detect the presence of a particular serotype of *Haemophilus influenzae* in the sample.

A sample which can be subjected to the present assay can be any sample which is suspected of containing or being contaminated with *Haemophilus influenzae*. Examples of such an sample include a blood sample, a nasopharyngeal sample, or an ear aspirate.

The assay can be used, therefore, as a diagnostic for the detection of infection of a subject, such as a mammal (e.g., a human), with *Haemophilus influenzae*. The assay can also be used to detect the presence of contamination of a material with *Haemophilus influenzae*, such as a food, medicament, or biological material.

In another embodiment, the protein can be used in an assay for detecting *Haemophilus influenzae* infection in a sample, such as a blood sample. For example, the pili of a pathogen can be isolated from the sample or recombinantly produced, employing the techniques described herein. One or more of the proteins, or fragments thereof, of the pili can then be sequenced. The sequences can be aligned to and compared with the corresponding protein sequence(s) of SEQ ID NO:4. Homology in excess of 90%, for example, is indicative of presence of the pathogen (i.e., infection) in the sample.

The pili protein, or a fragment thereof (e.g., a peptide fragment) can also be used in an immunoassay, specifically an ELISA, to detect the presence of antibodies in biological samples (e.g., blood, serum or tissue). Such immunoassay can be readily performed by those of skill in the art using well-established techniques to detect antibody bound to LKP pili protein or peptide fragments.

The pili proteins, or fragments thereof (also referred to herein as peptides, or peptide fragments), can also be used to produce antibodies that are reactive with the pili proteins described herein. The term antibody is intended to encompass both polyclonal and monoclonal antibodies. Polyclonal antibodies can be prepared by immunizing an animal with a preparation of crude or purified pili protein using techniques well-known to those of skill in the art. Pili fusion proteins can also be used for immunization. Monoclonal antibodies can be prepared using techniques known to those of skill in the art. These antibodies can be used in diagnostic assays to detect the presence of *H. influenzae* antibodies in biological samples as described above.

The invention is further specifically illustrated by the following examples.

EXAMPLE 1

Cloning and Sequencing of the LKP 5 hipP gene and the LKP1 Operon

Materials and Methods

Bacterial strains and plasmids

*H. influenzae* strains P860295 (ATCC 53775), P86149 (ATCC 53778), and P810384 (ATCC 53779), which express LKP serotypes 1, 4, and 5 respectively, described previously (Brinton, C. C. et al., *Pediatr. Infect. Dis. J.* 8 Suppl.: 54–61 (1989)) were employed. *E. coli* strains MB392 (Kar, S. et al., *Infect. Immun.* 58:903–908 (1990)) and HB101 were used as hosts for recombinant plasmids and strain DH5-α was used for cloning steps involving β-galactosidase α-peptide complementation. Hflu were grown in brain heart infusion (Dco Laboratories, Detroit, Mich.) containing 10 μg/ml hemin (Sigma Chemical Co., St. Louis, Mo.) and 2 μg/ml NAD (Sigma) at 37° C. *E. coli* strains were grown in Luria broth (Miller, J. H., In *Experiments in molecular genetics.*, 203 (1972). Cold Spring Harbor Laboratory. Cold Spring Harbor, N.Y.) at 37° C. Where appropriate, antibiotics were used at the following concentrations: ampicillin (Sigma) 100 μg/ml, kanamycin (Sigma) 25 μg/ml, and chloramphenicol (Sigma) 20 μg/ml.

Construction and properties of plasmid pHF1 which expresses LKP1 pili in *E. coli* as described previously (Kar, S. et al., *Infect. Immun.* 58:903–908 (1990)) were employed. Plasmid pPX551 is a pUC18 derivative containing the 1.9 kb XhoI fragment of pHF1 inserted into the BamHI site. Deletion clones of pHF1 lacking the pepN locus were constructed as described in the text. The LKP4 pilin structural gene was isolated by PCR amplification of P860295 chromosomal DNA using primers with the following sequences: for the 5' end of the gene- 5'GTGCTGGATCCGTTTCTCTTGCATTACATTAGG 3' (SEQ ID NO:12) and for the 3' end- 5'TTAGGAATTCG-GAAGCGTTTTTTACTTTTTTTGG3' (SEQ ID NO:13). The 5' primer included a HindIII restriction site, underlined in the sequence, and the 3' primer included an EcoRI site also shown underlined. The PCR product was cloned into pCR1000 (Invitrogen, Inc., Calif.) as per manufacturer's directions. The LKP4 structural gene was subcloned by blunting the EcoRI site with Klenow in the presence of all four dNTPs, and cutting with Asp718 I (an Asp718 I site is located in the vector) releasing the fragment. The LKP4 gene was ligated into HindII-Asp718 I cut pPX191 (a derivative of pUC19 with the bla gene replaced by the cat gene from pACYC184 (Chang, A. C. Y., and S. N. Cohen, *J. Bacteriol.* 134:1141–1156 (1978)) to form pPX602.

The LKP5 pilin structural gene was isolated from P810384 by PCR using the following primers: for the 5'end- 5'-AACGAATTCTGCTGTTTATTAAGGCTTTAG (SEQ ID NO:14) and for the 3'-AGCTGGATCCTTGTAGGGTGGGCGTAAGCC (SEQ ID NO:15). The PCR product of approximately 1 kb was cloned into pCRII (Invitrogen, Inc., San Diego, Calif. and subcloned as a blunt ended fragment by Klenow treatment of EcoRI ends generated using the vector's flanking EcoRI sites. The LKP5 pilin gene was subcloned into plasmid pPX191 and orientation determined by restriction analysis. The LKP5 subclone was saved as pPX605.

Cloning of hipP genes encoding other LKP serotypes hipP loci encoding serotype 4 and serotype 1 LKP genes have been described (Kar, S. et al., *Infect. Immun.* 58:903–908 (1990); van Ham, S. M. et al., *EMBO Jour.* 8:3535–3540 (1989)). To determine the serotype specificity of LKP pili is located within the hipP gene, PCR was used to clone the serotypes 4 and 5 pilin genes from an NTHi strains expressing these pili. The PCR product for the LKP4 pilin gene was cloned into pPX191 as described above and is expressed under control of the lac promoter. The hipP gene from an LKP5 expressing Hflu strain was isolated by PCR as described and cloned into pPX191 for expression under lac control.

Oligonucleotide synthesis

The synthetic oligonucleotides used as primers for PCR amplification and DNA sequencing were synthesized on an Applied Biosystems (ABI) 380B DNA synthesizer using b-cyanoethyl phosphoramidite chemistry (Sinha, N. D. et al., *Nucleic Acids Research* 12:4539–4557 (1984)).

Polymerase chain reaction (PCR) amplication

The LKP4 hipP and LKP5 hipP pilin genes were amplified by PCR from NTHi strains P861249 and P810384 respectively, using standard PCR amplification protocols (Saiki, R. K. et al., *Science* 239:487–491 (1988)).

DNA sequencing

The hipP gene contained on plasmid pPX551 and the entire LKP1 operon contained on plasmid pHF1 were sequenced with standard M13 sequencing primers and with overlapping sense and antisense primers. All the DNA sequencing was done on an Applied Biosystems (ABI) 373A DNA Sequencer, utilizing the Taq thermal cycling DyeDeoxy™ Terminator sequencing kit from ABI, part # 901497. The LKP4 and LKP5 serotypes were sequenced directly from the PCR products using the PCR amplification primers and internal synthetic primers based on the LKP1 sequencing study.

SDS-PAGE analysis

Sodium dodecyl sulfate polyacrylamide gel electrophoresis (SDS-PAGE) was performed in a 70 by 100 mm mini-gel system (Bio-Rad, Richmond, Calif.) using the method of Laemmli (Laemmli, U. K., *Nature* (London) 227:680–685 (1970)). Samples were reduced with β-mercaptoethanol or DTT in sample preparation buffer and boiled for 5 min. Gels were run at 150 V constant voltage. Separated proteins were detected by staining with Coomassie brilliant blue G-250 (Sigma).

Partial purification of pili

LKP pili were purified according to previously described methods using differential pH solubility (Brinton, C. C., Jr. et al., *Pediatr. Infect. Dis. J.* 8 *Suppl.*:54–61 (1989)). Briefly, piliated bacteria were harvested from liquid culture by centrugation and washed 2X in phosphate buffered saline, pH 7.2. The bacterial pellet was resuspended in 100 mM tris, pH 10.3, containing 150 mM NaCl at a ratio of 4 ml buffer/g wet weight of cells. Pili were sheared off of the cells by blending in an Oster miniblender for three 3 min bursts at 4° C. Bacterial debris was separated by centrugation and discarded. The supernatant was dialyzed against 50 mM NaAcetate, pH 5.0 overnight to precipitate pili and denature other proteins. The pellet was collected by centrugation at 15,000 x g at 4° C. and dissolved overnight in 50 ml of 0.01 M CAPS buffer, pH 10.4 with gentle rocking. This cycle of acid precipitation and solubilization in basic buffer was repeated two more times. The final acid pellet was then resolubilized in 0.01 M NaPhosphate, pH 10.4 and non soluble material discarded. This soluble fraction was referred to as partially purified pili.

Sequence of the LKP1 operon

The LKP1 operon was sequenced as described above and the full sequence is set forth in SEQ ID NO:4. Sequence analysis identified six potential open reading frames (ORFs) in the LKP operon, including the hipP (at about nucleotide 1882–2532 of SEQ ID NO:4) and hipC (at about nucleotide 2854–3630 of SEQ ID NO:4) genes. All six ORFs in the LKP operon were identified as homologous to equivalent pilus operon genes in the pilus superfamily, as defined by multiple sequence alignment of proteins. Analysis of sequence alignment was also performed using Entrez Sequences Database Release 10.0 of the National Center for Biotechnology Information (National Library of Medicine, Bethesda, Md.). Derived amino acid sequences of the ORFs are shown in FIGS. 2A–G (SEQ ID NOs:5–10). A function for each reading frame was assigned based on sequence alignment analysis. There are five ORFs which appear to be grouped into an operon controlled by the hipC promoter region. After the hipC (periplasmic chaperon) gene, the second reading frame hipR (at about nucleotide 4016–6238 of SEQ ID NO:4) was designated, a membrane anchor protein, the third ORF hipM (at about nucleotide 6259–6873 of SEQ ID NO:4) was designated, a tip associated protein, (also referred to herein as a minor tip protein) and the fourth ORF hipA (at about nucleotide 6955–8265 of SEQ ID NO:4) was designated, a tip adhesin protein. The pilin gene (hipP) and the periplasmic chaperon gene (hipC) are transcribed in opposite orientations as in the LKP 4 operon with the promoter region having the previously identified TA repeats (van Ham, S. M. et al., *Cell* 73:1187–1196 (1993)). Since pHF1 expresses LKP1 pili in *E. coli*, there are 10 TA repeats in the intrapromoter region as described by van Ham et al.. These TA repeats are responsible for phase variation of the LKP pili phenotype, with loss of some of the repeats resulting in loss of piliation and a TA repeat number between 10 or 11 allowing expression of the LKP operon. As identified on the LKP1 operon was an ORF encoding an integrase (at about nucleotide 1495–1868 of SEQ ID NO:4). Also located on the LKP1 operon was a sequence encoding an enzyme, peptidase (at about nucleotide 8395–9342 of SEQ ID NO:4).

The predicted size of the LKP1 hipP gene product is approximately 21.2 kilodaltons, assuming a signal sequence length of 20 amino acids, while the observed molecular weight in SDS-PAGE gels is approximately 27 kilodaltons. Part of this may be explained by the anomalous sequence migration of LKP pilins in general in SDS-PAGE gels (mature LKP4 migrates at a molecular size of 24 kilodaltons while its predicted size is 22.1 kilodaltons) but the exact explanation remains unknown.

Sequence comparison of LKP serotypes 1, 4, and 5 hipP genes

This report represents the first sequence analysis of the hipP genes encoding LKP serotypes 1 and 5 (FIG. 1). The hipP gene from an LKP4 expressing Hib strain has also been sequenced (van Ham, S. M. et al., *EMBO Jour.* 8:3535–3540 (1989)) and the derived amino acid sequence shows 99% identity with the LKP4 hipP derived amino acid sequence contained herein. The hipP gene sequences from Hib strains Eagan and M43 have been published (Forney, L. J. et al., *Infect. Immun.* 59:1991–1996 (1991)). The LKP1 hipP gene should encode a protein of approximately 21.5 kD while the predicted molecular weight of the LKP 4 hipP protein is 23.8 kD. The actual hipP gene products observed in recombinant *E. coli* are of approximately the correct sizes in Western blots for LKP4 and LKP5, but the LKP1 pilin runs aberrantly at a higher molecular weight than predicted at 26 kD. MacVector software was used to assess homology of these genes, with LKP4 hipP and LKP5 hipP proteins being 70 and 67% identical to LKP1 hipP, respectively. The alignment between the sequences is very good at the amino termini of the proteins, with three major areas of sequence divergence in the LKP1, 4, and 5 serotype genes farther into the proteins as shown in the Figure. Since little cross reactivity is observed between anti-LKP1, anti-LKP4, or anti-LKP5 sera with intact pili of a heterologous serotype, the sequences responsible for the serotype specificity of the typing antisera must be located in these regions. By comparison of the sequences in GenBank to the LKP4 sequence, the *H. influenzae* type b M43 pilin (Gilsdorf, J. R. et al., *Infect. Immun.* 58:1065–1072 (1990)) sequenced by Gilsdorf et al. also appears to be an LKP4 serotype gene (data not shown).

EXAMPLE 2

Construction of LKP Type Pili-Producing *E. coli* Recombinants

Bacterial strains

Piliated Hflu strains used for *E. coli* recombinant construction are LKP11/CB59, LKP10/88-0807 and LKP12/88-0677. Hemagglutination and serum agglutination were examined before making genomic library. *E. coli* strains XL1-Blue $^{MR}$ and HB101 were used as cloning host cell.

DNA library construction and cosmid vector DNA

Chromosomal DNA from LKP11, LKP10 and LKP12 were extracted and purified respectively by standard techniques. Hflu genomic DNA size is about $1.8 \times 10^6$ bp. Chromosomal DNA was partially digested with restriction enzyme Sau3A I. Approximately 30 kb DNA fragment was eluted from LMTA-gel (Sigma) and purified by phenol-chloroform method. The final DNA concentration is about 1 ug/ul.

Vector DNA SuperCos I (Stratagene, La Jolla, Calif.) was digested with Xba I and dephosphorylated with calf intestinal alkaline phosphatase (CIAP). The Xba I and CIAP treated vector DNA was then digested with Bam HI restriction enzyme. About 6.5 kb vector DNA fragment was obtained.

LKP11/CB59, LKP10/88-0807 and LKP12/88-0677 DNA fragments were ligated at the Bam HI site of the vector DNA SuperCos I, respectively. The ligated DNA was packaged into 1 phage particles using Ciga-pack Gold kit (Stratagene, La Jolla, Calif.). The host cell for packaging was XL1-Blue$^{MR}$.

Library screening

Figure 4:
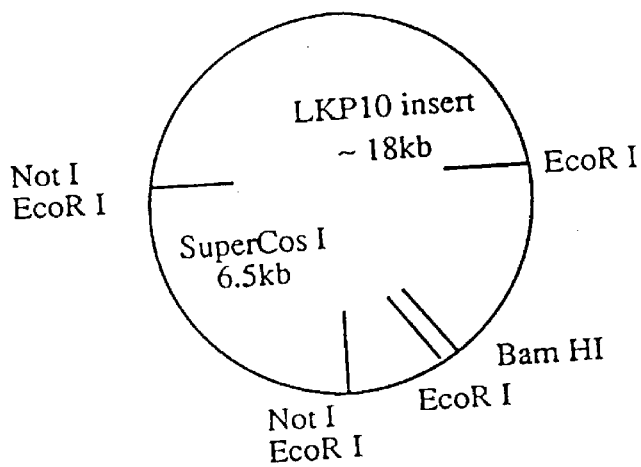
Figure 5:
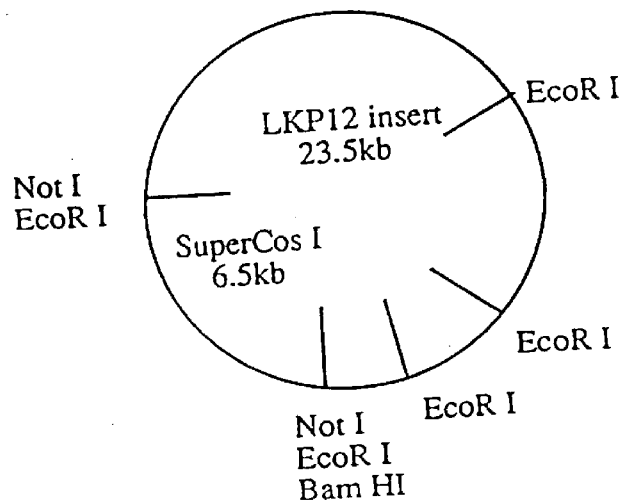

Recombinant expressed LKP type pili were screened by colony blot method. The concentration of anti-pilius sera from LKP11, LKP10 and LKP12 was 1:1000 dilution. The percentage of positive colony was 40/4200 for LKP11, 9/700 for LKP10 and 1/600 for LKP12. The cell piliation was examined by EM. The recombinants were verified by further HA and SA assay and they were named CLJ11 for LKP11, CLJ10 for LKP10 and CLJ12 for LKP12 (FIGS. 3, 4 and 5). Recombinants DNA was extracted and transformed to *E. coli* strain HB101 because XL1-Blue cell expresses type I pili. The recombinants DNA size is about 18.5 kb for CLJ11. This was obtained by digestion and subsequent ligation using restriction site on insert and vector DNA. CLJ10 DNA is about 25 kb and 35 kb is for CLJ12. Partial DNA sequence is available for these recombinant inserts.

EXAMPLE 3

Protocols for the Purification of an LKP Pilus from an *E. coli* Recombinant Strain Using the Liquid Phase Method General Protocol 1. Inoculate recombinant *E. coli* cells in a 3 ml of LB media containing ampicillin and grow at 370° C. until the OD 540 nm reading reaches 0.6–0.8 (3–4 hours).
2. Transfer the cell suspension to 50 ml of medium and grow at 37° C. until the reading at 540 nm reaches 0.8–1.0 (4–5 hours).
3. Transfer the 50 ml of cell suspension to 1 L of medium in 2.8 L flask and grow at 370° C. overnight (16–18 hours) until a reading at 540 nm of 4.0–5.0 is obtained.
4. Harvest cells by centrugation at 5000 rpm for 15 minutes.
5. Resuspend the cells in 50 nM acetate buffer pH 5.0 and keep the suspension at room temperature for 1 hour.
6. Blend at 11000 rpm in large cup, or 14000 rpm in small cup, with omnimixer, ice for 3 minutes.
7. Titrate to pH 8.0 with 1 M Tris-HCI and let stand for 3 hours at room temperature.
8. Centrifuge at 12000 rpm for 20 minutes at 40° C. Weigh all pellets and discard.
9. Add 10 ul of DNase and RNase for each 100 ml of prep. Mix thoroughly and let stand for 10 minutes at room temperature.
10. Dialyze against several changes of 50 mM acetate buffer pH 5.0 overnight. Of the prep does not reach pH 5.0 overnight, then dialyze longer against more changes of buffer.
11. Centrifuge at 16000 rpm for 60 minutes at 40° C. to pellet the protein precipitant and pilus crystals.
12. Resuspend the pellet in about 25% original volume with 25 mM Tris-HCI buffer pH 8.0.
13. With gentle stirring add TRINTON-X-100™ detergent and EDTA to the prep to yield final concentration of 0.2% and 5 mM. Stir gently overnight at 40° C.
14. Clarify the prep by centrifuging at 16000 rpm for 60 minutes at 40° C.
15. Add NaCl and PEG 8000 to final concentration of 0.5 M and 3.0% respectively then incubate and prep over ice for 2 hours.
16. Centrifuge the prep at 16000 rpm for 60 minutes at 40° C. to pellet the pilus crystals.
17. Resuspend pellet in 25 mM Tris-HCI pH 8.0 in ⅓ of previous volume. Use less solution a lesser yield of pilus crystals is obtained.
18. Repeat steps 13 to 17.
19. Resuspend pellet in 25 mM Tris-HCI pH 8.0. Depending on purity and amount of material alternative solubilization and crystallization steps may be continued as needed.

During purification, sample after each step and use SDS-PAGE to examine purity of the samples. Dark field microscopy assay is needed in assistance for purity checking. It is necessary to use UV scanning to determine any contamination by DNA or RNA.

Since TRITON-X-100™ detergent has a strong absorbance at 280 nm, it is important to remove the residual of TRINTON-X-100™ detergent by crystallization, one time, or more, of pili by PEG and NaCI after purification. This avoids false reading at 280 nm when one determines concentration of pilus preparation by UV method.

Purification of LKP 5 Pili

1. Harvest in 80 mM PBS pH 5.0 using 5–10 ml/tray.
2. Titrate prep to pH 5.0 with 6 N HCI if necessary.
3. Blend with omnimixer over ice for 3 minutes (average speed=9800 rpm) (up to 11000 rpm if possible in larger cups and up to 14000 rpm in small cups).
4. Titrate to pH 9.0 with 5 M NaOH and let stand for 3 hours at room temperature. It may be necessary to stir gently to prevent pH changes. Monitor pH throughout and adjust if needed. (If cultures were grown in broth, then titrate with a 1 M solution of buffer (Tris) instead of NaOH.)
5. Centrifuge at 15300 g for 20 minutes at 4° C. Transfer supernatant to clean bottles and clarify a second time as before. Weigh all pellets and discard.
6. Adjust pH of supernatant to 8.0 and add 10 ul of DNase and RNase for each 100 ml of prep. Mix thoroughly and let stand for 10 minutes at room temperature.

7. Dialyze against several changes of 40 mM acetate buffer pH 5.0 overnight. If prep does not reach pH 5.0 overnight then dialyze longer against more changes of buffer.
8. Centrifuge at 18600 g for 60 minutes at 4° C. to pellet the pilus crystals (crystals not typical for clear pili).
9. Resuspend the pellet in about 25% original volume with 25 mM Tris-CHI pH 9.0 using rubber policeman. Stir gently at 4° C. (avoid forming) several hours. Break up large pieces with gentle pipeting as needed.
10. With gentle stirring, add TRINTON-X-100™ detergent (2% stock) to the prep to yield a final concentration of 0.4% and add EDTA (25 mM stock) to a final concentration of 5 mM. Incubate overnight at 40° C.
11. Clarify the prep by centrifuging at 186000 g for 60 minutes at 4° C. Transfer supernatant to clean flask.
12. Adjust the pH of the supernatant to below 8.0 using 1 N HCI.
13. Add NaCI (5 M stock) to a final concentration of 0.5 M and PEG (30% stock) to final concentration of 3% then incubate the prep over ice for 0.5 hour. Inspect in darkfield for crystals. Increase time if needed but it is critical not to overexpose pili to PAGE because resolubilization becomes increasingly difficult with increasing times.
14. Centrifuge prep at 18600 g for 60 minutes at 4° C. to pellet the pilus crystals.
15. Wash pellet with 40 mM citrate buffer pH 5.0 to remove excess PEG/NaCI. Then centrifuge at 186000 g for 60 minutes (2 times).
16. Resuspend pellet in 25 mM Tris-CHI pH 9.0 in ⅓ to ½ previous volume. Solubilize by swirling followed by gentle pipetting. Run sample on a gel to check for purity. If necessary, continue with step 17.
17. Add TRINTON-X-100™ detergent to the prep to yield a final concentration of 0.4% and add EDTA to a final concentration of 5 mM then incubate overnight at 4° C. (see step 10 for details).
18. Adjust the pH of the prep to below 8.0 using HCI (between 7 and 8).
19. Add NaCI to a final concentration of 0.5 M and PEG to a final concentration of 3% then incubate the prep over ice for 0.5 hours (see step 13 for details).
20. Centrifuge prep at 186000 g for 60 minutes at 5° C. to pellet pilus crystals.
21. Resuspend the pellet in 252 mM Tris-HCI pH 9.0 to solubilize pili (see step 16 for details). Check for purity by SDS-PAGE. If necessary, continue with step 22.
22. Add Triton-X-100 to the prep to yield a final concentration of 0.4% and add EDTA to a final concentration of 5 mM then incubate overnight at 4° C. (see step 10 for details).
23. Clarify by centrifuging at 18600 g for 60 minutes at 4° C.
24. Add NaCI to a final concentration of 0.5 M and PEG to a final concentration of 3# then incubate the prep over ice for 0.5 hour (see step 13 for details).
25. Centrifuge at 18600 g for 1 hour at 4° C. Discard supernatant.
26. Resuspend pellet in Tris-HCI pH 9.0. Depending on amount and purity of material, alternating solubilization/crystallization steps may be continued as needed.

During purification process, monitor pellet material and supernatant by darkfield and/or gel and/or scan. May need to reprocess Purity by SDS-PAGE check: Repeat Triton step as needed, but avoid SDS reaction steps in previous protocols because of high losses of pili.

EXAMPLE 4

Purification of LKP pili by HPLC and other Column Methods

Besides detergent extraction and PEG precipitation, LKP pili also can be purified by HPLC, FPLC and other column methods. These methods are good particularly for unknown LKP pili. Normally, pili are partially purified by extraction and precipitation first until the pilus solution is clear, concentrated and very small size. The preparation still is not pure as determined by SDS-PAGE, column methods would be the application of the choice. Sizing columns are preferred to be used for this purpose. Prior to loading to a column, treatment for further purification of the pilus sample is important. The detergent used for partial purification of pili should be removed from pilus samples by dialysis or other known techniques. Detergent significantly reduces column separation resolution. Size exclusive column requires a small sample volume.

Figure 6A:
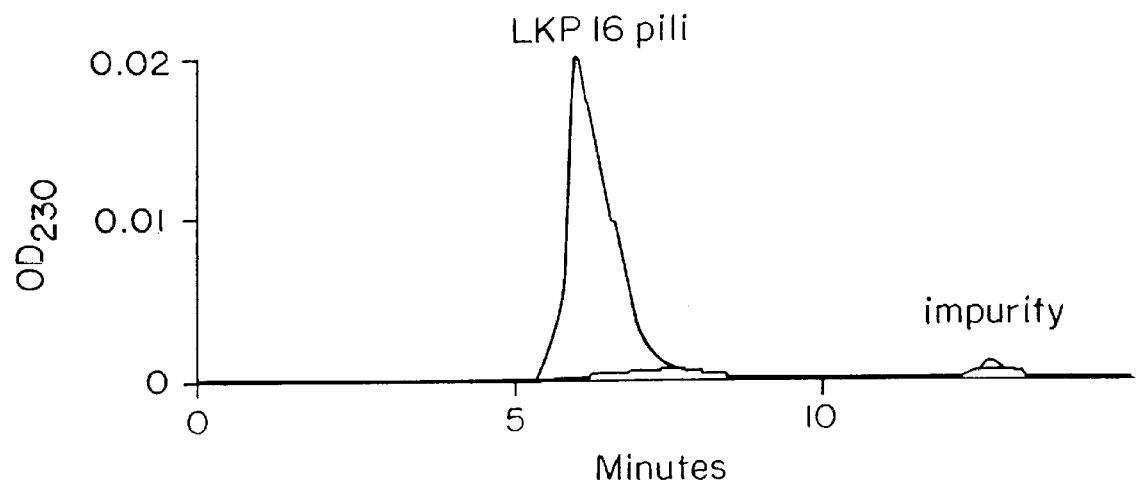
FIGS. 6A and 6B are graphic representations showing the HPLC purification of LKP16 and LKP19 pili. Protein was eluted out from a sizing column with 150 mM Tris-HCI, pH 8.0, monitored at 230 nm.
Figure 6B:
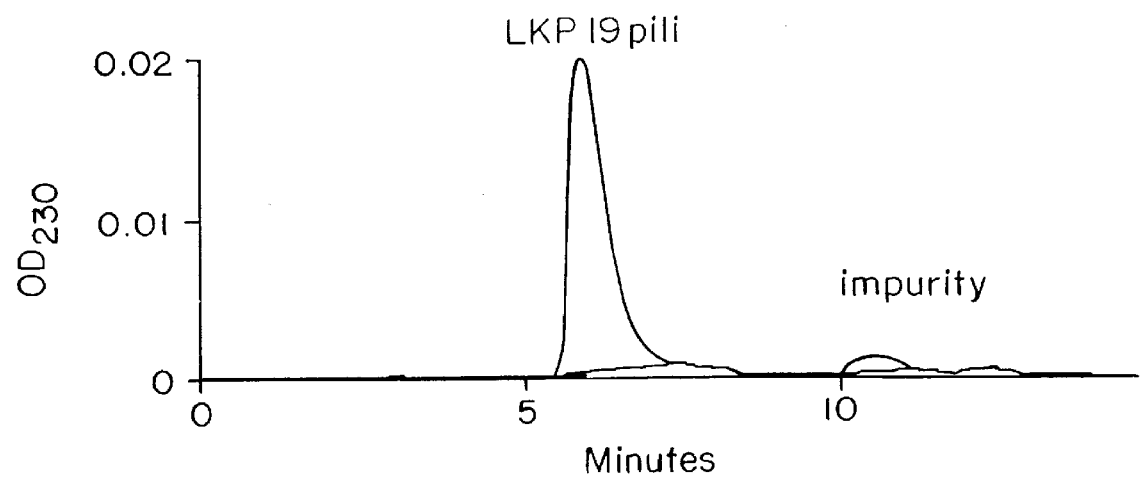
Figure 7:
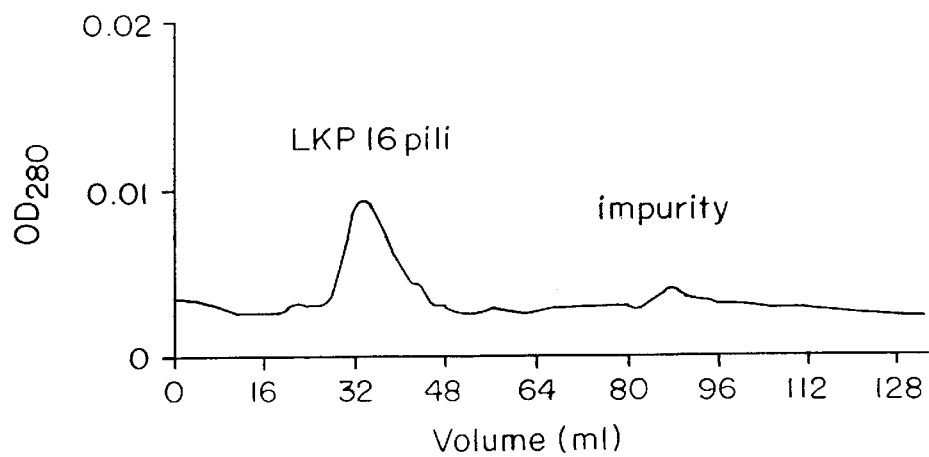
FIG. 7 is a graphic representation showing the purification of LKP16 pili with SEPHAROSE™ CL-6B beads column (1×50 cm). Protein was eluted out with 25 mM Tris-HCI, pH 8.0, monitored at 230 nm.
Figure 8:
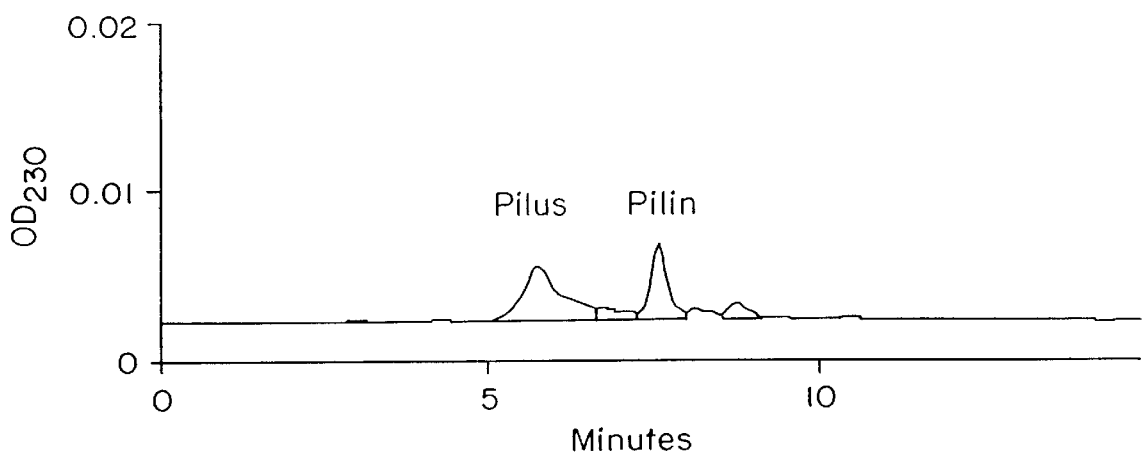
FIG. 8 is a graphic representation showing the HPLC separation of LKP1 pili and LKP1 pilin subunits. Protein was eluted out from a sizing column with 150 mM Tris-HCI, pH 8.0.

For HPLC or FPLC, the loading volume of 50 ul to 200 ul is recommended, and for other routine LC gel filtration columns, the sample loading volume depends on the length and size of the column. A 1 ml of pilus sample is preferred for a column with a total volume of 50 ml. Since pili have a low absorbance at 280 nm, a higher sensitivity for monitor is recommended. Available protein eluted from column can be monitored at 230 nm. FIGS. 6A and 6B show the purification of unknown pilus LKP16 from clinic isolate 880715 and LKP19 from 881219 by HPLC protein KW-804 column from Waters Company. Further purification of LKP16 by HPLC was seen. FIG. 7 shows the purification of LKP15 and LKP16 by a Sepharose CL-6B column (1×50 cm). Column methods are also useful for isolation of pilin from pili. FIG. 8 shows the isolation of LKP1 pilin from LKP1 pilus rods.

EXAMPLE 5

Protocol for the Purification of an LKP Pilus from an Hflu Strain or *E. coli* Recombinant Strain Using Solid Phase Method Generally speaking, recombinant strain expresses pilus structural protein better than parent strain, H flu, does, therefore, it is easier to purify pili from the recombinant cells. However, due to the fact that the *E. coli* recombinant strain expresses the pilus protein as same as the parent Hflu does, purification procedures of pilus rods from Hflu or from recombinant strain are basically the same. Growth of Hflu strain requires choclate agar media and certain $CO_2$ and humidity. Growth of *E. coli* recombinant strain needs LB agar media containing ampicillin.

1. Harvest in 80 mM PBS pH 5.0 using 5 ml/tray. Use a smoothed glass edge to scrape wet cells and then transfer the cell suspension to omnimixer cup. Less cells are made surface only use media surface moisture to collect wet cells.
2. Titrate prep to pH 5.0 with 2 M acetate buffer necessary.
3. Blend at 14000 rpm with omnimixer over ice for 3–5 minutes.
4. Titrate to pH 8.0 with 1 M Tris-HCI buffer and monitor pH change by pH meter. It may titrate to pH with 2.5 or 5 M NaOH instead of Tris buffer, prep contains a lot of wet cells. Be careful to avoid lysis of cells when use NaOH. Incubate the prep at room temperature for 3 hours.
5. Centrifuge at 12000 rpm for 20–30 minutes at 4° C. Weigh all pellets and discard.
6. Add 10 ul of DNase and RNase for each 100 ml of prep. Mix thoroughly and let stand for 10 minutes at room temperature.
7. Dialyze against several changes of 50 mM acetate buffer, pH 5.0, overnight. prep does not reach pH 5.0 overnight then dialyze longer against more changes of buffer.
8. Centrifuge at 16000 rpm for 60 minutes at 4° C. to pellet protein precipitate and pilus crystals.

9. Resuspend pellet in about 25% original volume with 25 mM Tris-HCI buffer, pH 8.0.
10. With gentle stirring, add TRINTON-X-100™ detergent and EDTA to prep to yield final concentration of 0.2% and 5 mM. Stir gently overnight at 40° C.
11. Clarify prep by centrugation at 16000 rpm for 60 minutes at 40° C.
12. Add NaCl and PEG 8000 to final concentration of 0.5 M and 3.0%, respectively, then incubate the prep over ice for 2 hours. LKP pili with different length and dimer may be crystallized in different concentrations of NaCl and PEG 8000. Therefore a concentration test for NaCl and PEG to crystalize different pili is important.
13. Centrifuge at 16000 rpm for 60 minutes at 40° C. to pellet pilus crystals.
14. Resuspend pellet in 25 mM Tris-HCI, pH 8.0 in ⅓ previous. Use even less solution a smaller yield of pilus crystal is found.
15. Repeat from step 10 to step 14.
16. Resuspend pellet in 25 mM Tris-HCI, pH 8.0. Depending on purity and amount of material, alternate solubilization and crystallization steps may be continued as needed.

During purification, sample after each step and use SDS-PAGE to examine purity of the samples. Dark field microscopy assay is needed in assistance for purity checking. It is necessary to use UV scanning for finding out any contamination by DNA or RNA.

Since TRINTON-X-100™ detergent has a strong absorbance at 280 nm it is wise to remove the residual of the detergent by one more time crystallization of pili by PEG and NaCl after purification. This avoids false readings at 280 nm when one determines concentration of pilus preparation by UV method.

EXAMPLE 6

Construction of MBP-Δ3'Tip Fusion Protein

The genetic fusion was constructed by using PCR primers to obtain a portion of the LKP1 tip gene from pHF1 which would be in frame with the MBP protein gene in the vector pMAL-p2. The primers were designed so that the carboxyl terminal of approximately 100 amino acids of the tip protein would be deleted and replaced with a stop codon. The amino terminal portion of the protein was PRC'd in frame with an appropriate restriction site at the approximate point of the signal sequence cleavage site which was determined by analogy to other bacterial signal sequences and the hydrophobicity profile of the deduced amino acid sequence of the tip protein. The amino acid sequence of the fusion protein is shown in FIG. 9. The partial sequence of the LKP tip protein of the fusion protein is underlined.

Expression of the fusion, purification, and antisera production

The protein was expressed in E. coli BL21 (an onnipT. lon K-12 strain) grown in SOB broth containing ampicillin at 100 μg/ml at 28 C after induction with 0.2 mM IPTG. The cells were pelleted by centrugation and washed 1 time in PBS. The cells were resuspended in 20 mM Tris, pH 7.5 containing 2 mM EDTA and 400 mM NaCl at a ratio of 20 ml/liter of original culture. The cells were lysed by passing through a French pressure cell 3 times and the cell debris removed by low speed centrugation at 8 times x g for 20 minutes at 4° C. The supernatant was diluted 5-fold in the same buffer used for breakage and passed over a 15 ml bed volume amylose resin column at 1 ml/min at room temperature. After the lysate was run over the column, the column was washed with 15 bed volumes of the lysing buffer at 5 ml/min. The bound material was eluted using washing buffer containing 10 mM maltose. The elution was done with 50 ml of buffer at 1 ml/min and the eluant pooled. The resulting protein mixture was analyzed by SDS-PAGE and Western Blot and anti-MBP sera and found to contain the fusion, breakdown products, and full length MBP. Little other material was detected.

The fusion proteins, MBP and breakdown products eluted as a complex. Mice were immunized with 10 μg doses of the complex using 100 μg MPL as adjuvant. Immunizations were done subcutaneously at weeks 0, 4, and 6 and the mice exsanguinated on week 8. The negative control sera was mouse anti-MBP sera made against purified MBP using the same purification and immunization protocols.

Anti-GST sera

The GST fusion was constructed using the complete LKP tip gene, including the signal sequence. The gene was PCR'd out from PHF1 with the appropriate restriction enzyme sites for insertion into pGEX-3X in frame, and expressed in E. coli DH5α. The cells were grown in SOB containing 100 μg/ml ampicillin and induced with IPTG at 0.2 mM at 37° C. for 2 hours. The cells were harvested and washed in PBS, then resuspended in PBS and lysed by passing through a French pressure cell. Cell debris was harvested by centrugation, and washed 3 times with buffer containing 1% TRINTON-X™-Zwittergent 3–14 and the inclusion bodies recovered by centrugation. The inclusion bodies, were solubilized in 5 M guanidine HCl and analyzed by SDS-PAGE. The guanidine concentration was lowered to 2.5 M by dialysis and the soluble inclusion bodies stored at 4° C. The antisera was made by running preparative 10% SDS-PAGE gels and cutting the fusion band out of the gel. The acrylamide-protein band was minced using a scalpel and mixed with MPL (100 μg) and injected into mice 3 times at weeks 0, 4, and 6. Mice were bled at week 8.

EXAMPLE 7

Removal, Purification and Identification of H. influenzae LKP Pilus Tip Adhesin Protein This is the first demonstration that tip adhesin protein from H. influenzae LKP1 pili can be removed without depolymerization of pilus rods. Free tip adhesin protein can be isolated and purified by means of dialysis and prep-electrophoresis. Purified tip adhesin can be identified by the antiserum from a constructed genetic fusion protein, which is from a portion of LKP1 tip gene and MBP (maltose binding protein) gene, using Western blot analysis. Specific binding was detected between the purified tip protein and fusion protein antiserum, which clearly shows that the protein purified from LKP1 pilus prep is LKP1 tip adhesin protein.

Activity assays with human red blood cell (RBC) ghosts demonstrated that purified tip protein binds to a native ghosts preparation but not does not bind to denatured RBC ghosts, indicating that purified tip protein is biologically functional or at least partially functional.

Removal of Tip Protein from Pilus Rods
1. Dialyze purified LKP1 pili in 200 mM Gly-HCl buffer, pH 2.0 containing 5 M NaCl, at room temperature for 4 to 6 hours.
2. Transfer the dialysis bag into a 25 mM Tris-HCl buffer, pH 8.0 and dialyze for several hours till the pH of pilus prep reaches to pH 8.0.
3. Add SDS to the pilus prep to a final concentration of 0.1% and incubate in 4° C. for 10 hours.

4. Dialyze the pilus prep in 50 mM citrate buffer, pH 5.0 overnight.
5. Pilus aggregates can be removed by centrugation and most free tip protein is retained in the supernatant.

Tip protein can be completely removed by 2% SDS in 25 mM Tris buffer without depolymerization of pilus rods, but the SDS may damage the activity of the protein. 0.1% SDS only removes about 20–30% of total tip protein, however, the protein maintains biological activity. The results also demonstrated that 4 M urea and 2 M GuHCl in pH 2.0 buffer can partially remove tip protein from pilus rods without depolymerization.

Figure 10:
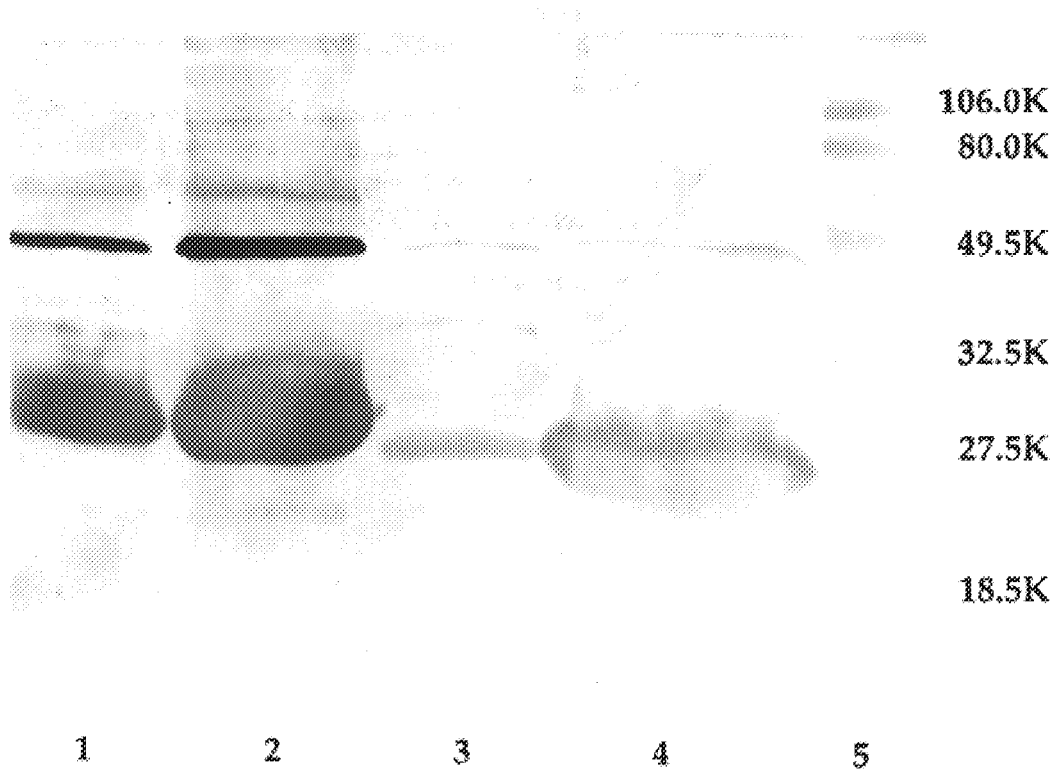
FIG. 10 is a photograph of a gel showing the identification of LKP1 tip adhesin protein by antibodies reactive with the fusion protein of LKP1 tip adhesin-MBP in Western blotted membranes. Lanes 1 and 2: different preps of purified LKP1 pili with tip protein (47 Kd). (A positive reaction was shown between tip protein and the antibody); lane 3: purified LKP10 pili with tip adhesin (47 Kd). (The tip protein does not react with the antibody); lane 4: purified LKP11pili with tip protein (47 Kd). (The tip protein does not react with the antibody); lane 5: protein molecular weight markers.
Figure 11:
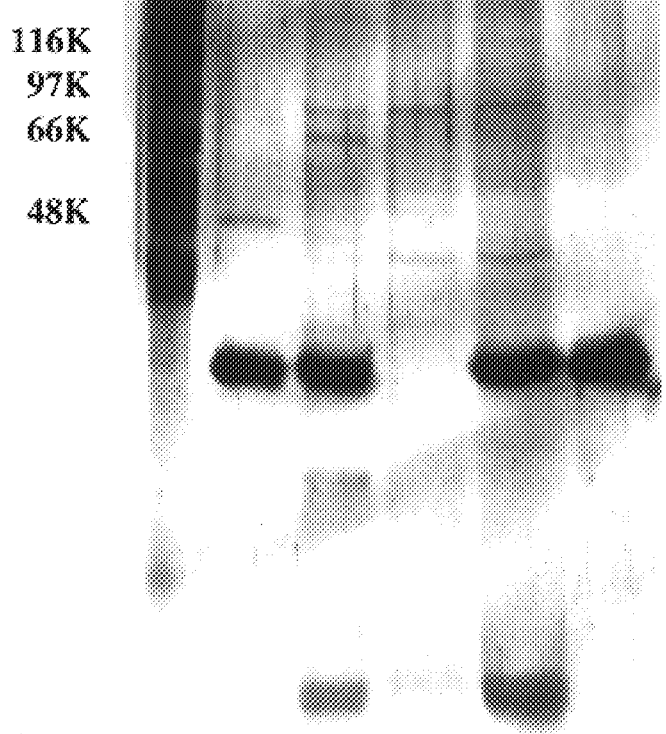
FIG. 11 is a photograph of a gel showing the binding activity of LKP1 tip adhesin to human red cell (HRC) ghosts. Lane 1: molecular weight markers; lane 2: purified LKP1 pili with tip protein; lane 3: the pili with HRC ghosts after centrifugation. Tip protein band (47 Kd) disappeared due to the binding of tip adhesin pili to ghosts pellet; lane 4: HRC ghosts after centrifugation, used as control; lane 5: purified pili without tip protein (treated with 1% SDS) was incubated with fresh ghosts, showing the same protein band pattern as the pattern of lane 3; Lane 6: purified pili without tip protein. Prior to the gel loading, pili were treated with 1% SDS, exhaustively dialyzed in 25 m Tris buffer, pH 8.0, crystallized by PEG plus NaCl and resolubilized in 25 mM Tris buffer, pH 8.0.
Figure 12:
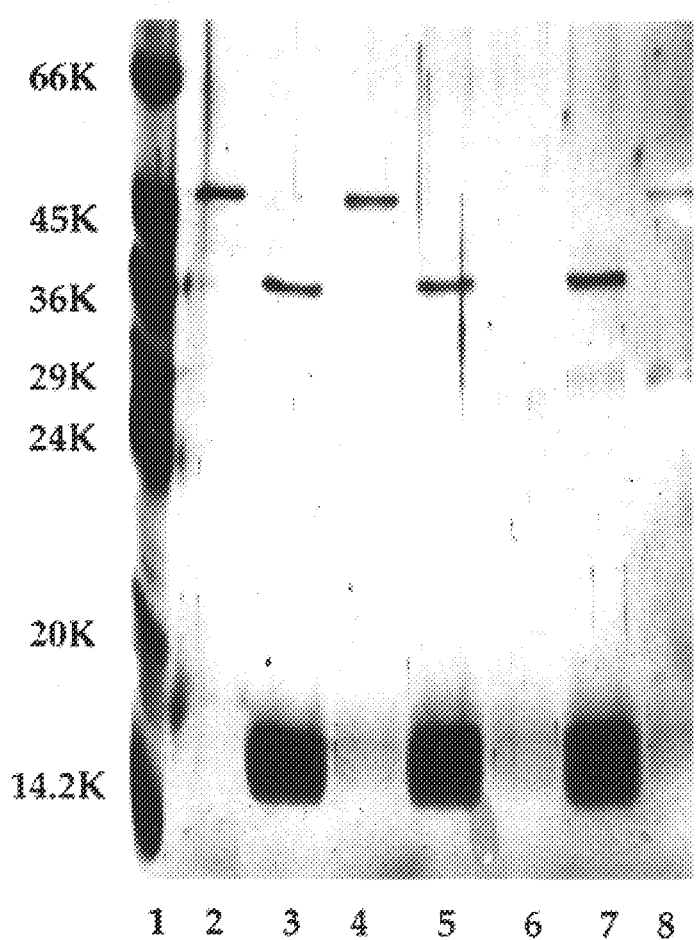
FIG. 12 is a photograph of a gel showing the binding activity of purified LKP1 tip adhesin protein to human red cell ghosts. Lane 1: molecular weight markers; lane 2: purified tip adhesin protein with a molecular weight of 47 Kd and the protein was removed by 0.1% SDS in 100 mM Glycine buffer, pH 2.0; lane 3: purified adhesin was incubated with fresh human red cell ghosts and pelleted by centrifugation prior to loading the supernatant on the gel. The tip adhesin band disappeared due to the binding to HRC ghosts; lane 4: purified adhesin was incubated with boiled HRC ghosts and pelleted by centrifugation prior to loading the supernatant on the gel. It showed adhesin band with 47 Kd, which indicates that tip adhesin protein does not bind to the ghosts pellet; lane 5: supernatant of fresh ghosts after centrifugation. It was used as a control; lane 6: supernatant of boiled HRC ghosts after centrifugation, showing a different soluble protein pattern from that of fresh HRC ghosts, used as another control; lane 7: different prep of purified tip protein incubated with fresh HRC ghosts, which showed the binding between tip protein and fresh HRC ghosts pellet; lane 8: different prep of purified tip protein incubated with boiled HRC ghosts, indicating that the tip protein does not bind the denatured ghosts. The gel was silver stained.
Figure 13:
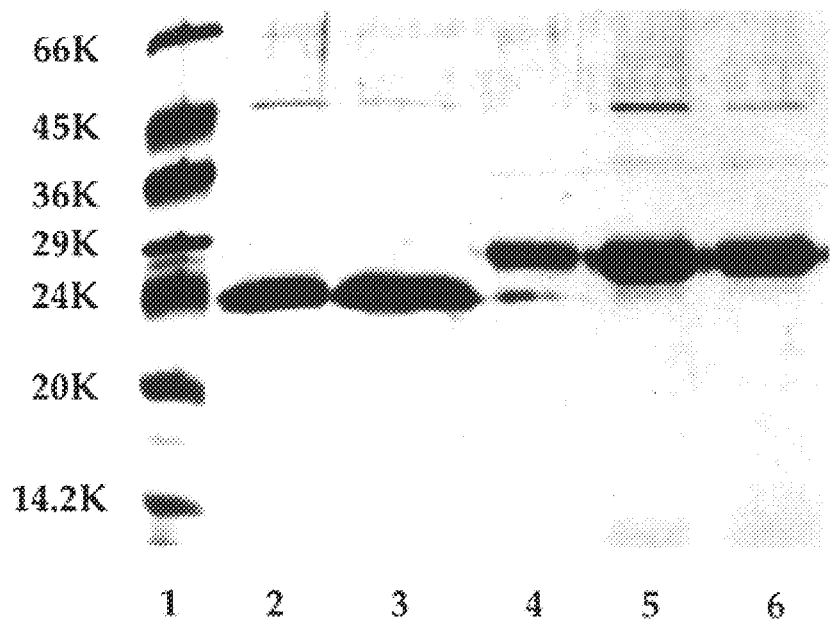
FIG. 13 is a photograph of a gel showing adhesin proteins from different LKP type pili with the same molecular weight. Lane 1: molecular weight markers; lane 2: LKP10pili; lane 3: LKP11 pili and lane 4 to 6: different purified preparation of LKP1 pili (SEQ ID NO:4) and the deduced amino acid sequence for six open reading frames (SEQ ID NOs: 5–10). Proteins were stained with silver.

Purification of tip protein
1. Mix concentrated tip protein with SDS-PAGE sample treatment buffer without the SDS and β-mercaptolethanol. The ratio is 2.5 ml of pilus prep to 0.3 ml of sample treatment buffer.
2. Load the sample to a 12% SDS-PAGE (0.1% SDS) in Prep-Cell (Bio-Rad) with the length of stacking gel of 0.8–1.0 cm and running gel of 5 cm.
3. Run the gel at 300 volt with cooling system for 6–8 hours, and monitor the elution at 280 nm.
4. Pool the fractions containing tip protein and concentrate.
5. Determine the purity of the pooled fractions by mini-SDS-PAGE. The identication of purified tip protein by anti-KLP1-MBP fusion protein is shown in FIG. 10. The binding activity of purified tip protein with human red cell ghosts is shown in FIGS. 11 and 12. FIG. 13 compares adhesin proteins from different LKP type pili by SDS/PAGE.

EXAMPLE 8

Serotype Analysis

The *Haemophilus influenzae* (Hflu) bacterioplex is a differentiated complex of bacterial phases, or cell types, socially organized to facilitate the protein appendages expressed on the surface of Hflu, and also secreted from Hflu in free form, carrying specific adhesion determinants for binding to human cell membrane receptors. Pili adapt pathogenic bacteria to life in vertebrate hosts by mimicking the functions of the host's own proteins. Pilus functions include attaching bacteria to a variety of host cells and tissues and stimulating the host's immune system in ways which benefit the bacteria and damage the host. Pili are transmission, virulence, dissemination, pathogenicity and immunity factors in most bacterial diseases.

The expression of pili is controlled by a genetic switching mechanism, phase variation, in which pilus expression and pilus type are switched on and off at probabilities which vary with and are determined by conditions and signals in the immediate environment of the bacteria. Under some conditions the switching probabilities can be very high, as high as $10^{-2}$ per bacterial cell division. Under other environmental conditions the probability of the same phase switch can be $10^{-6}$ or lower. Phase switching is accompanied by both reversible and irreversible rearrangements in the DNA of pilus operons. Phase switching during in vitro growth is frequently accompanied by deletions to pilus operon genes such that nonpiliated phases remain irreversibly in that phase.

By purifying Hflu pili from different isolates and producing antisera to the purified preparations distinct LKP pilus serotypes have so far been identified. The expression of the different serotypes is used as a marker to identify the different piliation phases of the Hflu bacterioplex.

TABLE 1

|  |  | L = 1 | L = 2 | L = 3 | D = 3 | D = 4 |
|---|---|---|---|---|---|---|
| LKP1 | N = 4 | 0 | 0 | 4 | 0 | 4 |
| LKP2 | N = 2 | 0 | 1 | 1 | 0 | 2 |
| LKP3 | N = 0 | 0 | 0 | 0 | 0 | 0 |
| LKP4 | N = 1 | 0 | 1 | 0 | 0 | 1 |
| LKP5 | N = 5 | 0 | 1 | 4 | 0 | 5 |
| LKP6 | N = 12 | 0 | 2 | 8 | 1 | 9 |
| LKP7 | N = 3 | 0 | 0 | 2 | 0 | 2 |
| LKP8 | N = 0 | 0 | 0 | 0 | 0 | 0 |
| LKP9 | N = 0 | 0 | 0 | 0 | 0 | 0 |
| LKP10 | N = 26 | 1 | 8 | 17 | 2 | 24 |
| LKP11 | N = 22 | 0 | 6 | 16 | 0 | 22 |
| LKP12 | N = 12 | 0 | 3 | 7 | 2 | 8 |
| LKP13 | N = 0 | 0 | 0 | 0 | 0 | 0 |
| LKP14 | N = 9 | 1 | 2 | 6 | 1 | 8 |
| LKP15 | N = 6 | 0 | 5 | 1 | 0 | 6 |
| LKP16 | N = 9 | 0 | 4 | 5 | 3 | 6 |
| LKP17 | N = 17 | 0 | 6 | 11 | 2 | 15 |
| LKP18 | N = 12 | 1 | 4 | 7 | 1 | 11 |
| LKP19 | N = 3 | 0 | 1 | 3 | 0 | 3 |
| LKP20 | N = 15 | 1 | 6 | 8 | 3 | 12 |
| Total Strains = 77 |  | 4 | 50 | 99 | 15 | 136 |

L = 1 is length <0.2μ
L = 2 is length <0.2μ < 0.5μ
L = 3 is length <0.5μ
D = 3 is 3 nm diameter ("thin")
D = 4 is 4 nm diameter ("thick")

The frequency of each LKP serotype was determined for all serotypable cultures and for all cultures expressing typical LKP pili. The serotype frequency was determined by counting types on both single expressors and multiple expressors. Sixteen of the 20 serotypes were found on typically LKP piliated cultures and 90% of these cultures were serotypable in the 20-type system. The frequency distribution of serotypes for these cultures is shown in Table 1.

Three different LKP pilus operon genes were selected, the pilin gene, anchor gene and adhesin gene, which had all exhibited sequence similarity among different serotypes in multiple sequence alignments, but were also characteristic of Hflu LKP pili. Sequences were selected from these genes that would serve as suitable primer sequences flanking each gene for use in a PCR reaction.

| LKP1 Pilin: | HF2 5'>AGCTGGATCCTTGTAGGGTGGGCGTAAGCC<3' (SEQ ID NO:16) |
|---|---|
|  | HF1 5'>AACGGATTCGTTTGCTGTTTATTAAGCCTT<3' (SEQ ID NO:17) |
| LKP1 Anchor: | R5 5'>GCCGCACCTTTGATGAACG>3' (SEQ ID NO:18) |
|  | R3 5'>GGCAAATACGCACCGCTAAAT>3' (SEQ ID NO:19) |
| LKP1 Adhesin: | A5 5'>CGGACGAAGATGGTACAACGA>3' (SEQ ID NO:20) |
|  | A31 5'>CCAAGCTTGGCCCGACATTATTATTGATATGACA>3' (SEQ ID NO:21) |

All three pairs of primers were synthesized and used in a PCR reaction to amplify segments of DNA extracted from Hflu isolates.

Data showing the presence of LKP pilus operons in tested *Haemophilus influenzae* strains is shown in Table 2.

TABLE 2

CORRELATION BETWEEN THE PRESENCE OF LKP PILUS OPERON GENETIC MATERIAL IN *H. INFLUENZAE* ISOLATES AND THE EXPRESSED LKP PARAMETERS OF PILIATION AND HEMAGGLUTINATION

| LKP Parameter | Total | PCR Done | PCR+ | PCR− | Fraction PCR+ | Percent PCR+ |
|---|---|---|---|---|---|---|
| Pilus Length 0 | 74 | 68 | 59 | 9 | 59/68 | 87% |
| Pilus length 3 | 101 | 93 | 82 | 11 | 82/93 | 88% |
| HA+ | 148 | 139 | 115 | 24 | 115/139 | 83% |
| HA− | 166 | 149 | 119 | 30 | 119/149 | 80% |
| Pilus Diam. 3 | 40 | 38 | 28 | 10 | 28/38 | 74% |
| Pilus diam. 4 | 172 | 159 | 136 | 23 | 136/159 | 86% |
| Serotypable | 189 | 173 | 149 | 24 | 149/173 | 86% |
| Not serotypable | 54 | 63 | 53 | 10 | 53/63 | 84% |

1. Pilus length 0 means nonpiliated.
2. length 3 means >0.5 microns (longest, typical of LKP pili).
3. HA+ means positive for hemagglutination of human red blood cells; typical of LKP pili. (These isolates are not recalcitrant by definition.)
4. HA− means negative for hemagglutination of human red blood cells; typical of SNN pili. (These isolates are recalcitrant since all isolates were hemadsorbed at least once.)
5. Pilus diameter 3 means the isolates express pili with diameters typical of SNN pili.
6. Pilus diameter 4 means the isolates express pili with diameters typical of LKP pili.
7. Serotypable means the isolates agglutinate under standard conditions with at least one of the LKP pilus typing antisera in the 1–20 system.
8. Not serotypable means the isolates do not agglutinate with any of the LKP pilus typing antisera in the 1–20 system.

EXAMPLE 9

Hybridization Assay for *Haemophilus Influenzae*
Assay Probe Construction

An approximately 1100 bp fragment from plasmid pHF1 (Karasic, R. et al., *Pediatr. Infect. Dis. J.* 8 (*Suppl.*):S62–65 (1988)) which contains the LKP1 serotype operon was amplified by PCR using primers which hybridize at the 5' and 3' ends of the hipA gene. This gene encodes the tip adhesin protein of the LKP1 pili. The PCR reaction included digoxigenin labeled dUTP along with the four dNTPs to label the PCR reaction product with digoxigenin. This probe was electrophoresed on an agarose gel and purified by cutting out the ~1.2 kb band and extracting the DNA by standard methods. The probe was redissolved in 30 µl of appropriate buffer.

Hybridization Assay

Eleven randomly chosen Haemophilus influenzae clinical isolates were grown on BHI-XV plates at 37° C. with 5% $CO_2$ and also streaked onto BHI agar. All isolates grew only on the BHI-XV plate, indicating that they were *H. influenzae*. The isolates included 2 Hib strains and 9 NTHi. The strains were inoculated onto a nylon membrane placed onto BHI-XV agar. Five clinical isolates of another respiratory pathogen, *Moraxella catarrhalis* were also spotted onto the filter. The bacteria were grown overnight at 37° C. in 5% $CO_2$. After growth, 2 *Bordetella pertussis* strains were spotted onto the filter. Filters were processed for colony hybridization according to the method of Maniatis et al. (*Molecular Cloning: A Laboratory Manual*, 1991, Cold Spring Harbor Laboratories, Cold Spring Harbor, N.Y.). Filters were blocked in pre-hybridization solution as described by Boehringer-Mannheim for the Genius™ system at 65° C. for 3 hours. Colony debris was removed by gentle rubbing with wet paper towels. The probe, 30 µl, was added to 5 ml of pre-hybridization solution and boiled for 10 minutes to denature the DNA. Probe was immediately added to the filter and allowed to hybridize overnight at 65° C. Filters were washed in 2X SSC, 0.1% SDS, 2X for 5 min/wash at room temperature followed by 2, 15 minute washes with 0.2X SSC, 0.1% SDS at 65° C. Bound probe was detected using alkaline phosphatase labeled anti-digoxigenin antibodies as described by the manufacturer. Results are shown in Table 3.

TABLE 3

HYBRIDIZATION OF dig-LABELED LKP 1 TIP PROBE TO RANDOM CLINICAL ISOLATES

| | Number of Positive Results | | | |
|---|---|---|---|---|
| Bacterial Strain | Strong Signal | Weak Signal | No Signal | # Total |
| *H. influenzae* | 4 | 4 | 3 | 11 |
| *M. catarrhalis* | 0 | 0 | 5 | 5 |
| *B. pertussis* | 0 | 0 | 0 | 2 |

The probe was specific for *H. influenzae* with no hybridization seen with either *M. catarrhalis* or *B. pertussis*.

Hybridization Assay of Nontypable Strains of *Haemophilus influenza* pili

Ten LKP pili expressing NTHi strains which express differing serotypes of LKP pili, along with Hib Eagan were grown on a nylon filter overlayed onto chocolate agar at 37° C. in 5% $CO_2$. An additional NTHi isolate was also included. After growth, two strains appeared yellow on the filter which was suggestive of non-*Haemophilus* bacteria, so they were tested by growth on BHI and BHI-XV. This experiment showed them to be contaminants and not NTHi. The filter was removed from the agar and processed as described above. The probe from the first experiment was reboiled and added to the filter as before, except that the hybridization temperature was lowered to 62° C. The filter was washed as before except that the wash temperature was also 62° C. Bound probe was detected as above. Results are shown in Table 4.

TABLE 4

HYBRIDIZATION OF dig-LABELED TKP TIP PROBE TO LKP TYPE STRAINS

| LKP Serotype | Signal with probe | No signal with probe | ID of strain |
|---|---|---|---|
| 5 | Strong | | NTHi |
| 2 | Moderate | | NTHi |
| 9 | Strong | | NTHi |
| 1 | Strong | | NTHi |
| 6 | Moderate | | NTHi |
| 13 | Strong | | NTHi |
| 4 | Strong | | NTHi |
| 7 | Moderate | | NTHi |
| | | X | Contaminant |
| | | X | Contaminant |
| 10 | Weak | | NTHi |
| 4 | Strong | | Hib |

The results set forth above establish that the DNA probes hybridized selectively to *Haemophilus influenzae*.

Equivalents

Those skilled in the art will recognize, or be able to ascertain using not more than routine experimentation, mant equivalents to the specific embodiments of the invention described herein. Such equivalents are intended to be encompassed by the following claims.

We claim:

1. An isolated nucleic acid sequence said sequence selected from the group consisting of:
   a) SEQ ID NO: 4;
   b) the fully complementary strand of SEQ ID NO: 4;
   c) DNA sequences that specifically hybridize to SEQ ID NO:4; and
   d) RNA sequences transcribed from the sequences of a), b) or c).

2. An isolated nucleic acid sequence said sequence selected from the group consisting of:
   a) nucleotides 2854 to 3630 of SEQ ID NO:4;
   b) the fully complementary strand of a);
   c) DNA sequences that specifically hybridize to the sequence of a); and
   d) RNA sequences transcribed from the sequences of a), b) or c).

3. An isolated nucleic acid sequence said sequence selected from the group consisting of:
   a) nucleotides 4016 to 6238 of SEQ ID NO:4;
   b) the fully complementary strand of a);
   c) DNA sequences that specifically hybridize to the sequence of a); and
   d) RNA sequences transcribed from the sequences of a), b), or c).

4. An isolated nucleic acid sequence said sequence selected from the group consisting of:

a) nucleotides 6259 to 6873 of SEQ ID NO:4;

b) the fully complementary strand of a);

c) DNA sequences that specifically hybridize to the sequence of a); and d) RNA sequences transcribed from the sequences of a), b), or c).

5. An isolated nontypable *Haenophilus influenzae* serotype 1 LKP periplasmic chaperone protein said protein consisting of SEQ ID NO:6, or an antigenic or biologically active fragment thereof, said biologically active fragment having an activity selected from the group consisting of:

a) mediating hemagglutination of human erythrocytes; and b) adhering to cell membrane receptors expressed on epithelial cells.

6. An isolated nontypable *Haemophilus influenzae* serotype 1 LKP membrane anchor protein, said protein consisting of SEQ ID NO:7, or an antigenic or biologically active fragment thereof, said biologically active fragment having an activity selected from the group consisting of:

a) mediating hemagglutination of human erythrocytes; and b) adhering to cell membrane receptors expressed on epithelial cells.

7. An isolated nontypable *Haemophilus influenzae* serotype 1 LKP tip associated protein, said protein consisting of SEQ ID NO:8, or an antigenic or biologically active fragment thereof, said biologically active fragment having an activity selected from the group consisting of:

a) mediating hemagglutination of human erythrocytes; and b) adhering to cell membrane receptors expressed on epithelial cells.

8. A recombinant nontypable *Haemophilus influenzae* LKP tip adhesin fusion protein comprising a fragment of serotype 1 LKP tip adhesin protein consisting of SEQ ID NO:9, and maltose binding protein or glutathione-S-transferase.

9. A recombinant nontypable *Haemophilus influenzae* serotype 1 LKP tip adhesin fusion protein consisting of SEQ ID NO:11.

10. A method of producing an antibody which binds to nontypable *Haemophilus influenzae* serotype 1 LKP tip adhesin protein comprising immunizing a mammal with a recombinant *Haemophilus influenzae* LKP tip adhesin fusion protein comprising a fragment of LKP tip adhesin protein consisting of SEQ ID NO:9 and maltose binding protein or glutathione-S-transferase.

11. The method of claim 10 wherein the LKP tip adhesion fusion protein consists of SEQ ID NO:11.

12. A DNA probe that specifically hybridizes to a DNA sequence encoding the nontypable *Haemophilus influenzae* tip adhesin protein, said sequence consisting of nucleotides 6955 to 8265 of SEQ ID NO:4.

13. A DNA probe of claim 12 which comprises about 400 nucleotides.

14. The DNA probe of claim 12 which comprises about 1000 nucleotides.

15. The DNA probe of claim 12 which comprises about 1200 nucleotides.

16. The DNA probe of claim 12 further comprising a detectable label.

17. A method of assaying for the presence of nontypable *Haemophilus influenzae* in a biological sample comprising the steps of contacting the sample with a DNA probe comprising about 400 nucleotides which specifically hybridizes to a DNA sequence encoding a tip adhesin protein, wherein the DNA sequence encoding the tip adhesin protein consists essentially of nucleotides between 6955 to 8265 of SEQ ID NO: 4, under conditions suitable for specific hybridization and detecting the presence of specifically hybridized DNA.

18. The method of claim 17 wherein the DNA sequence encoding the tip adhesin protein consisting essentially of nucleotides between about 6955 to 8265 of SEQ ID NO:4.

19. The method of claim 18 wherein the DNA probe comprises about 1000 nucleotides.

20. The method of claim 19 wherein the DNA probe further comprises a detectable label.

21. The method of claim 20 wherein the DNA probe is attached to a solid support.

22. An isolated nucleic acid sequence encoding a protein of the nontypable *Haemophilus influenzae* serotype 1 LKP operon.

23. The isolated nucleic acid sequence of claim 22 wherein said protein is periplasmic chaperone protein.

24. The isolated nucleic acid sequence of claim 22 wherein said protein is membrane anchor protein.

25. The isolated nucleic acid sequence of claim 22 wherein said protein is tip associated protein.

* * * * *